(12) United States Patent
Schobert et al.

(10) Patent No.: US 8,980,933 B2
(45) Date of Patent: Mar. 17, 2015

(54) COMBRETASTATIN ANALOGS FOR USE IN THE TREATMENT OF CANCER

(75) Inventors: Rainer Schobert, Zell (DE); Bernhard Biersack, Prebitz (DE); Thomas Müller, Halle (DE)

(73) Assignees: Universitat Bayreuth, Bayreuth (DE); Martin-Luther-Universitat Halle-Wittenberg, Halle (DE)

( * ) Notice: Subject to any disclaimer, the term of this patent is extended or adjusted under 35 U.S.C. 154(b) by 243 days.

(21) Appl. No.: 13/695,804

(22) PCT Filed: May 5, 2011

(86) PCT No.: PCT/EP2011/057234
§ 371 (c)(1),
(2), (4) Date: Jan. 8, 2013

(87) PCT Pub. No.: WO2011/138409
PCT Pub. Date: Nov. 10, 2011

(65) Prior Publication Data
US 2013/0137740 A1 May 30, 2013

(30) Foreign Application Priority Data
May 5, 2010 (EP) .................................... 10161990

(51) Int. Cl.
| | |
|---|---|
| A61K 31/4164 | (2006.01) |
| A61K 31/4178 | (2006.01) |
| A61K 31/42 | (2006.01) |
| C07D 233/64 | (2006.01) |
| C07D 263/32 | (2006.01) |
| C07D 403/04 | (2006.01) |
| A61K 45/06 | (2006.01) |
| A61N 5/10 | (2006.01) |
| C07D 233/58 | (2006.01) |
| C07D 403/10 | (2006.01) |

(52) U.S. Cl.
CPC ......... *A61K 31/4164* (2013.01); *A61K 31/4178* (2013.01); *A61K 31/42* (2013.01); *A61K 45/06* (2013.01); *C07D 233/64* (2013.01); *C07D 263/32* (2013.01); *C07D 403/04* (2013.01); *A61N 5/10* (2013.01); *C07D 233/58* (2013.01); *C07D 403/10* (2013.01)
USPC ........................................ 514/400; 548/343.5

(58) Field of Classification Search
USPC ........................................ 514/400; 548/343.5
See application file for complete search history.

(56) References Cited

FOREIGN PATENT DOCUMENTS

WO    WO 01/09103 A2    2/2001

OTHER PUBLICATIONS

Bedford et al., "Synthesis of Water-soluble Prodrugs of the Cytotoxic Agent Combretastatin A4," Bioorg. Med. Chem. Lett., 1996, pp. 157-160, vol. 6, No. 2.
Brown et al., "Synthesis of Biologically Active Heterocyclic Stilbene and Chalcone Analogs of Combretastatin," Top Heterocycl. Chem., 2006, 51 pages.
Desagher et al., "Bid-induced Conformational Change of Bax Is Responsible for Mitochondrial Cytochrome c Release during Apoptosis," J. Cell Biology, Mar. 1999, pp. 891-901, vol. 144, No. 5.
Dugan, Jr. et al., "A New Technique for Explantation and In Vitro Cultivation of Chicken Embryos," The Anatomical Records, 1991, pp. 125-128, vol. 229.
Fisher C.J., "Chick Embryos in Shell-less Culture," Chapter 8, 1993, Assoc. Biol. Lab. Education, 1993, 5, pp. 105-115.
Folkes et al., "Oxidative Metabolism of Combretastatin A-1 Produces Quinone Intermediates with the Potential To Bind to Nucleophiles and To Enhance Oxidative Stress via Free Radicals," Chem. Res. Toxicol., 2007, pp. 1885-1894, vol. 20, No. 12.
Holwell, et al., "Anti-tumor and Anti-vascular Effects of the Novel Tubulin-binding Agent Combrestastatin A-1 Phospate", AntiCancer Research, 2002, 22, pp. 3933-3940.
Jobmann, "Aus der Klinik fur Innere Medizin," Schwerpunkt Kardiologie der Phillips—Universitat Marburg, 2002, pp. 1-97.
Kiss et al., "Dicovery of a Long-Acting, Peripherally Selective Inhibitor of Catechol-O-methyltransferase," J. Med. Chem., 2010, pp. 3396-3411, vol. 53, No. 8.
Lippert J.W., III, "Vascular disrupting agents," Bioorg. & Med. Chem., 2007, pp. 605-615, vol. 15.
Mueller et al., "Failure of Activation of Caspase-9 Induces a Higher Threshold for Apoptosis and Cisplatin Resistance in Testicular Cancer," Cancer Res., Jan. 2003, pp. 513-521, vol. 63 (Announcements attachment).
Mueller et al., "Loss of Oct.-3/4 Expression in Embryonal Carcinoma Cells Is Associated with Induction of Cisplatin Resistance," Tumor Biol., 2006, pp. 71-83, vol. 27.

(Continued)

*Primary Examiner* — Rebecca Anderson
(74) *Attorney, Agent, or Firm* — Foley & Lardner LLP

(57) ABSTRACT

The present invention relates to specific analogs of combretastatin, in particular the compounds of formula (I) as described and defined herein, and pharmaceutical compositions comprising the compounds, as well as their medical use, in particular in the treatment or prevention of cancer, including multidrug-resistant cancer.

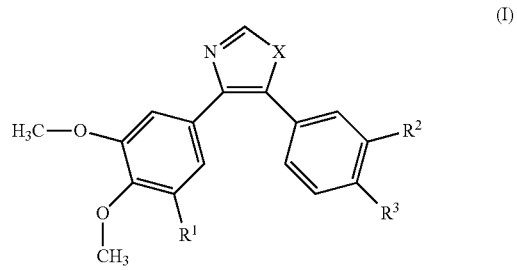

(I)

15 Claims, 19 Drawing Sheets

(56) References Cited

OTHER PUBLICATIONS

Figure 1:
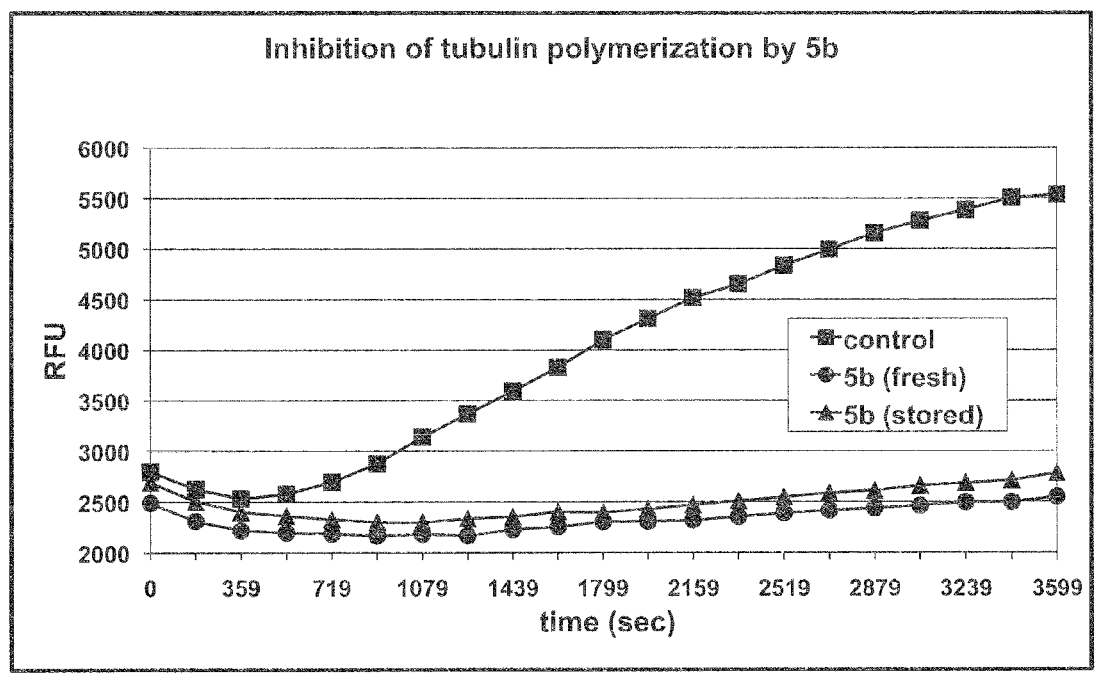

Ohsumi et al., "Syntheses and Cntitumor Activity of CIS-restricted Combretastatins: 5-membered Heterocyclic Analogues," Bioorg. Med. Chem. Lett., 1998, pp. 3153-3158, vol. 8.

Orsini, et al., "Natural Stilbenes and Analogues as Antineoplastic Agents", Atta-ur-Rahman (Ed.) Studies in Natural Products Chemistry, vol. 34, 2008. pp. 78-127.

Papazisis et al., "Optimization of the sulforhodamine B colorimetric assay," J. Immunol. Methods, 1997, pp. 151-158, vol. 208.

Pettit et al., "Antineoplastic Agents. 509. Synthesis of Fluorcombstatin Phosphate and Related 3- Halostilbenes," J. Nat. Prod., 2005, pp. 1450-1458, vol. 68, No. 10.

Rook et al., "A Simple Method for the Solubilisation of Reduced NBT, and Its Use as a Colorimetric Assay for Activation of Human Macrophages by γ-Interferon," J. Immunol. Methods, 1985, pp. 161-167, vol. 82.

Roxana et al., "Up-to-date in the hematological malignancies treatment," Medica—A Journal of Clinical Medicine, 2006, pp. 63-65, vol. 1, No, 1.

Schobert, et al., "4-(3-Halo/amino-4,5-dimethoxyphenyl)-S-aryloxazoles and -N-methylimidazoles That Are Cytotoxic against Combretastatin A Resistant Tumor Cells and Vascular Disrupting in a Cisplatin Resistant Germ Cell Tumor Model", J. Med. Chem., 2010, 53, pp. 6595-6602.

Taylor P.C., "Antibody therapy for rheumatoid arthritis," Current Opinion in Pharmacology, 2003, pp. 323-328, vol. 3.

Tron et al., "Medicinal Chemistry of Combretastatin A4: Present and Future Directions," J. Med. Chem., Jun. 2006, pp. 3033-3044, vol. 49, No. 11.

Vasilevsky et al., "Heterocyclic Analogs of Combretastatin A-4," Chem. Heterocyclic Compounds, 2008, pp. 1257-1261, vol. 44, No. 10.

Wang et al., "Potent, Orally Active Heterocycle-Based Combretastatin A-4 Analogues: Synthesis, Structure-Activity Relationship, Pharmacokinetics, and In Vivo Antitumor Activity Evaluation," J. Med. Chem., 2002, pp. 1697-1711, vol. 45, No. 8.

Wilting et al., "A modified chorioallantoic membrane (CAM) assay for qualitative and quantitative study of growth factors," Anat. Embryol., 1991, pp. 259-271, vol. 183.

(A)

(B)

(A)

(B)

(A)

(B)

1411HP germ cell tumor day 0        day 1

6b (A)

(B)

(C)

(D)

(E)

DLD1 colon carcinoma line (F)

HCT8 colon carcinoma line (A)

(B)

(C)

(D)

COMBRETASTATIN ANALOGS FOR USE IN THE TREATMENT OF CANCER

CROSS-REFERENCE TO RELATED PATENT APPLICATIONS

This application is the U.S. National Stage of International Application PCT/EP2011/057234, filed May 5, 2011, and published in English on Nov. 10, 2011 as WO 2011/138409, which claims the benefit of European Application No. 10161990.6, filed May 5, 2010.

The present invention relates to specific analogs of combretastatin, in particular the compounds of formula (I) as defined herein, and pharmaceutical compositions comprising the compounds, as well as their medical use, in particular in the treatment or prevention of cancer, including multidrug-resistant cancer.

The chemotherapy of cancer is generally limited by the high incidence of malignant tumors that display resistance to a range of chemical anti-tumor agents, either intrinsically or acquired upon repeated administration. Currently, there are no clinically established chemotherapeutical agents capable of overcoming this so-called multidrug resistance. An alternative therapy of such cases is not available, either.

A water-soluble phosphate prodrug of the angiotoxic, naturally occurring lead compound combretastatin A-4 (CA-4) has already entered clinical phase II and III trials against various incurable cancer diseases.

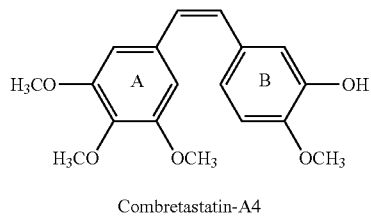

Combretastatin-A4

CA-4 and analogs thereof are strongly cytotoxic and selectively disrupt tumoral vasculature or prevent its neoformation (so-called antivascular or antiangiogenic effect, respectively). They also bind to tubulin and inhibit its polymerization thus impeding the cell proliferation (antimitotic effect). In combination, these effects lead to an inhibition of tumor cell proliferation and of the growth and spread of solid tumors (invasion, metastasis).

A drawback of CA-4 is its insufficient cytotoxicity which necessitates combination regimens with carboplatin or taxol in the therapy of solid tumors. Treatment with CA-4 alone often led to the persistence of peripheral cancer cells and hence to tumor relapses (Trop et al., *J. Med. Chem.* 2006, 49, 3033-3044; Lippert, *Bioorg. Med. Chem.* 2007, 15, 605-615). The related CA-1 and its bisphosphate prodrug OXi4503 were also impressively efficacious in certain tumor models owing to their catechole moiety. Catecholes are known to undergo redox cycling via quinoid intermediates thus mediating the generation of reactive oxygen species (ROS) and the alkylation of bionucleophiles (Holwell at al., *Anticancer Res.* 2002, 22, 3933-40; Folkes et al., *Chem. Res. Toxicol.* 2007, 20, 1885-1894).

The problem of insufficient cytotoxicity of CA-4 in vivo was overcome by developing combretastatin A-1 diphosphate which has a direct impact on cancer cells. However, like CA-4 this compound is prone to isomerization and thus deactivation. A preclinical study revealed that this isomerization can be precluded by replacing the olefin bridge by five-membered heterocycles such as oxazoles or imidazoles (Wang at al., *J. Med. Chem.* 2002, 45, 1697-1711). The resulting products are characterized by an improved water solubility and applicability in vivo without the need of prodrug formulations. In another study CA-4 analogous 3-halostilbenes were shown to have an enhanced affinity for tubulin and a more selective profile of efficacy (Pettit et al., *J. Nat. Prod.* 2005, 68, 1450-1458). Similar compounds are furthermore disclosed in: WO 01/09103; Vasilevsky et al., *Chemistry of Heterocyclic Compounds*, 2008, 44(10), 1257-1261; Orsini et al., Natural stilbenes and analoga as antineoplastic agents, in: Atta-ur-Rahman, Studies in Natural Products Chemistry, Bioactive Natural Products, Part N, 2008, Volume 34; Brown at al., *Top. Heterocycl. Chem.* 2006, 2, 1-51; Kiss L E et al., *J Med Chem*, 2010, 53(8), 3396-411; and Ohsumi K at al., *Bioorg Med Chem Lett*, 1998, 8(22), 3153-8.

Compounds resembling those prepared by Wang et al. or Pettit et al. fulfil only some rather than all of the requirements for optimum anti-tumor efficacy. Derivatives reminiscent of those described by Wang et al. feature favourable pharmacological properties yet diminished tubulin affinity and cytotoxicities (ca. 1/100 th of that of CA-4) that are insufficient to treat resistant tumors effectively. On the other hand, compounds with increased cytotoxicity showed unfavourable pharmacological properties and lacked antivascular efficacy and activity against resistant tumors. Among the 3-halocombretastatin-A derivatives disclosed by Pettit et al. there are some with distinct cytotoxic properties. However, owing to their stilbene nature and their lack of a stabilizing heterocyclic bridge, they tend to isomerize with loss of anticancer activity. In addition, their solubility in water and thus their applicability in vivo is rather limited unless converted into a phosphate ester. They were not amenable to tests with in vivo models. Moreover, the efficacy of the compounds described in Wang et al. and in Pettit et al. in the treatment of multi-resistant cancer and, in particular, in the treatment of CA-4-refractory cancer has not been examined.

Hence, there is a strong demand for improved methods for the treatment or prevention of cancer, in particular multidrug-resistant cancer.

The compounds of formula (I), (II) or (III) as defined herein below have an improved efficacy against cancer, in particular against resistant tumor cells, and sufficient solubility in water or serum. They generally have a low toxicity which avoids cumulative dose restrictions and leads to improved tolerance. Furthermore, they have an improved chemical stability and thus reduced tendency to inactivation.

Accordingly, the present invention relates to a compound of formula (I)

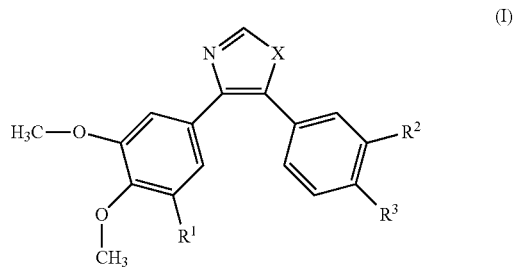

or a pharmaceutically acceptable salt, solvate, or prodrug thereof.

X is selected from O, S, N(H), or N(C$_{1-4}$alkyl). Preferably, X is selected from O or N(C$_{1-4}$ alkyl). More preferably, X is selected from O or N(CH$_3$).

R$^1$ is selected from halogen, —CN, —CF$_3$, —NH$_2$, —NH(C$_{1-4}$ alkyl), or —N(C$_{1-4}$ alkyl)(C$_{1-4}$ alkyl). Preferably, R$^1$ is selected from halogen (such as, e.g., —F, —Cl, or —Br), or —NH$_2$. More preferably, R$^1$ is selected from —Cl, —Br, or —NH$_2$. Most preferably, R$^1$ is selected from —Cl or —Br.

R$^2$ is selected from hydrogen, halogen, —CN, —CF$_3$, —OH, —O(C$_{1-4}$ alkyl), —NH$_2$, —NH(C$_{1-4}$ alkyl), or —N(C$_{1-4}$ alkyl)(C$_{1-4}$ alkyl). Preferably, R$^2$ is selected from hydrogen, halogen (such as, e.g., —F, —Cl, or —Br), —OH, or —NH$_2$. More preferably, R$^2$ is selected from —F, —OH, or —NH$_2$.

R$^3$ is selected from —OH, —O(C$_{1-4}$ alkyl), —SH, —S(C$_{1-4}$ alkyl), —NH$_2$, —NH(C$_{1-4}$ alkyl), or —N(C$_{1-4}$ alkyl)(C$_{1-4}$ alkyl). Preferably, R$^3$ is selected from —O(C$_{1-4}$ alkyl) or —N(C$_{1-4}$ alkyl)(C$_{1-4}$ alkyl). More preferably, R$^3$ is selected from —O—CH$_3$, —O—CH$_2$—CH$_3$ or —N(CH$_3$)$_2$, particularly from —O—CH$_3$ or —N(CH$_3$)$_2$.

Alternatively, R$^2$ and R$^3$ jointly form a group —C(halogen)=CH—N(CH$_3$)—, wherein the halogen is preferably selected from —F, —Cl, or —Br, and more preferably the halogen is —Cl. That is, R$^2$ and R$^3$ form a 5-membered ring together with the carbon atoms which they are attached to, wherein R$^2$ and R$^3$ together are a bivalent group —C(halogen)=CH—N(CH$_3$)— or, preferably, a group —C(Cl)=CH—N(CH$_3$)—.

Accordingly, the compound of formula (I) may have the following structure:

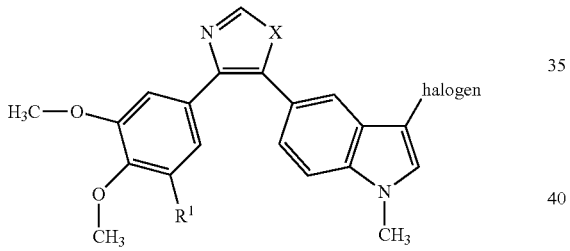

wherein the halogen may, e.g., be —F, —Cl, or —Br, and preferably is —Cl, and the other groups X and R$^1$ are as defined above.

In a preferred embodiment, R$^2$ is —NH$_2$ and R$^3$ is —O—CH$_3$. In a further preferred embodiment, X is O or N(CH$_3$), R$^1$ is —NH$_2$ or halogen (such as, e.g., —F, —Cl, or —Br), R$^2$ is —NH$_2$, and R$^3$ is —O—CH$_3$. Accordingly, a preferred compound of formula (I) is 1-methyl-5-(3-amino-4-methoxyphenyl)-4-(3-chloro-4,5-dimethoxyphenyl)-imidazole (also referred to as "5b" or "compound 5b"). Another preferred compound of formula (I) is 1-methyl-5-(3-amino-4-methoxyphenyl)-4-(3-bromo-4,5-dimethoxyphenyl)-imidazole (also referred to as "6b" or "compound 6b").

In another preferred embodiment, R$^2$ is —NH$_2$ and R$^3$ is —O—CH$_2$—CH$_3$. In a further preferred embodiment, X is O or N(CH$_3$), R$^1$ is —NH$_2$ or halogen (such as, e.g., —F, —Cl, or —Br), R$^2$ is —NH$_2$, and R$^3$ is —O—CH$_2$—CH$_3$. Particularly preferred compounds of formula (I) are, accordingly, 1-methyl-5-(3-amino-4-ethoxyphenyl)-4-(3-chloro-4,5-dimethoxyphenyl)-imidazole (i.e., 1-methyl-5-(3"-amino-4"-ethoxyphenyl)-4-(3'-chloro-4',5'-dimethoxyphenyl)-imidazole; also referred to as "5f" or "compound 5f") and 1-methyl-5-(3-amino-4-ethoxyphenyl)-4-(3-bromo-4,5-dimethoxyphenyl)-imidazole (i.e., 1-methyl-5-(3"-amino-4"-ethoxyphenyl)-4-(3'-bromo-4',5'-dimethoxyphenyl)-imidazole; also referred to as "6f" or "compound 6f").

In another preferred embodiment, R$^2$ is —F and R$^3$ is —O—CH$_3$ or —O—CH$_2$—CH$_3$. In a further preferred embodiment, X is O or N(CH$_3$), R$^1$ is —NH$_2$ or halogen (such as, e.g., —Cl, or —Br), R$^2$ is —F, and R$^3$ is —O—CH$_3$ or —O—CH$_2$—CH$_3$. Accordingly, preferred compounds of formula (I) are 1-methyl-4-(3-chloro-4,5-dimethoxyphenyl)-5-(3-fluoro-4-ethoxyphenyl)-imidazole (also referred to as "5g" or "compound 5g") and 1-methyl-4-(3-bromo-4,5-dimethoxyphenyl)-5-(3-fluoro-4-ethoxyphenyl)-imidazole (also referred to as "6g" or "compound 6g").

Further preferred compounds of formula (I) are 1-methyl-4-(3-amino-4,5-dimethoxyphenyl)-5-(N-methyl-3-chloroindol-5-yl)-imidazole (i.e., 1-methyl-4-(3'-amino-4',5'-dimethoxyphenyl)-5-(N-methyl-3"-chloroindol-5"-yl)-imidazole; also referred to as "8e" or "compound 8e"), 1-methyl-4-(3'-chloro-4',5'-dimethoxyphenyl)-5-(N-methyl-3"-chloroindol-5"-yl)-imidazole (also referred to as "5i" or "compound 5i"), and 1-methyl-4-(3'-bromo-4',5'-dimethoxyphenyl)-5-(N-methyl-3"-chloroindol-5"-yl)-imidazole (also referred to as "6i" or "compound 6i").

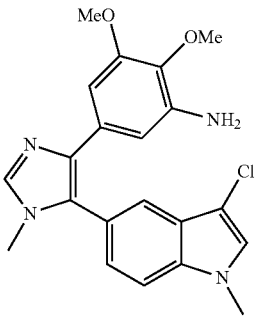

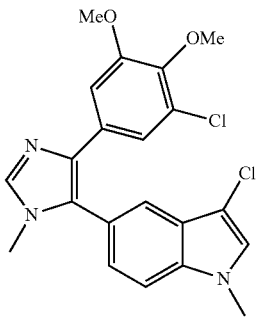

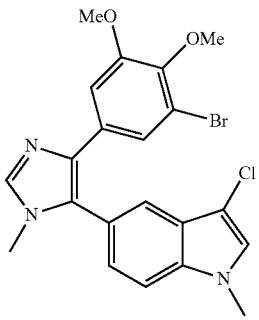

The present invention further provides a compound of formula (II)

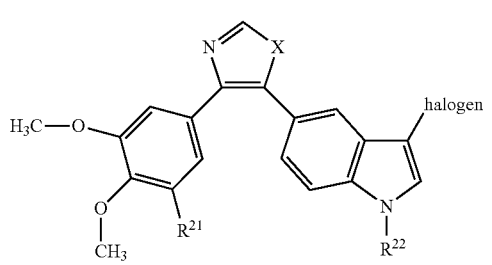

or a pharmaceutically acceptable salt, solvate, or prodrug thereof.

$X^2$ is selected from O, S, N(H), or N($C_{1-4}$ alkyl). Preferably, $X^2$ is selected from O or N($C_{1-4}$ alkyl). More preferably, $X^2$ is selected from O or N($CH_3$).

$R^{21}$ is selected from halogen, —CN, —$CF_3$, —$NH_2$, —NH($C_{1-4}$alkyl), or —N($C_{1-4}$ alkyl)($C_{1-4}$ alkyl). Preferably, $R^{21}$ is selected from halogen (such as, e.g., —F, —Cl, or —Br), or —$NH_2$. More preferably, $R^{21}$ is selected from —Cl, —Br, or —$NH_2$. Most preferably, $R^{21}$ is selected from —Cl or —Br.

$R^{22}$ is $C_{1-4}$ alkyl. Preferably, $R^{22}$ is $C_{2-4}$ alkyl. More preferably, $R^{22}$ is ethyl.

The group "halogen" comprised in the compound of formula (II) is preferably selected from —F, —Cl, or —Br, and more preferably the "halogen" is —Cl.

Preferred compounds of formula (II) are 1-methyl-4-(3-amino-4,5-dimethoxyphenyl)-5-(N-methyl-3-chloroindol-5-yl)-imidazole, 1-methyl-4-(3'-chloro-4',5'-dimethoxyphenyl)-5-(N-methyl-3''-chloroindol-5''-yl)-imidazole, and 1-methyl-4-(3'-bromo-4',5'-dimethoxyphenyl)-5-(N-methyl-3''-chloroindol-5''-yl)-imidazole. A particularly preferred compound of formula (II) is 1-methyl-4-(3'-bromo-4',5'-dimethoxyphenyl)-5-(N-ethyl-3''-chloroindol-5''-yl)-imidazole (also referred to as "6h" or "compound 6h").

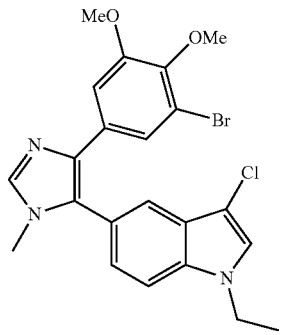

The invention also provides a compound of formula (III)

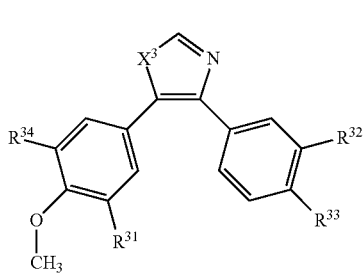

or a pharmaceutically acceptable salt, solvate, or prodrug thereof.

$X^3$ is selected from O, S, N(H), or N($C_{1-4}$ alkyl). Preferably, $X^3$ is selected from O or N($C_{1-4}$ alkyl). More preferably, $X^3$ is selected from O or N($CH_3$).

$R^{31}$ is selected from halogen (particularly —Cl, —Br or —I), —CN, —$CF_3$, —$NH_2$, —NH($C_{1-4}$alkyl), or —N($C_{1-4}$ alkyl)($C_{1-4}$ alkyl). Preferably, $R^{31}$ is selected from —Cl, —Br, —I, or —$NH_2$. More preferably, $R^{31}$ is selected from —Br, —I, or —$NH_2$. Most preferably, $R^{31}$ is selected from —Br or —I.

$R^{32}$ is selected from hydrogen, halogen, —CN, —$CF_3$, —OH, —O($C_{1-4}$ alkyl), —$NH_2$, —NH($C_{1-4}$ alkyl), or —N($C_{1-4}$ alkyl)($C_{1-4}$ alkyl). Preferably, $R^{32}$ is selected from hydrogen, halogen (such as, e.g., —F, —Cl, or —Br), —OH, or —$NH_2$. More preferably, $R^{32}$ is selected from —F, —OH, or —$NH_2$. Most preferably, $R^{32}$ is —F.

$R^{33}$ is selected from —OH, —O($C_{1-4}$ alkyl), —SH, —S($C_{1-4}$ alkyl), —$NH_2$, —NH($C_{1-4}$ alkyl), or —N($C_{1-4}$ alkyl)($C_{1-4}$ alkyl). Preferably, $R^{33}$ is selected from —O($C_{1-4}$ alkyl) or —N($C_{1-4}$ alkyl)($C_{1-4}$ alkyl). More preferably, $R^{33}$ is selected from —O—$CH_3$, —O—$CH_2$—$CH_3$ or —N($CH_3$)$_2$. Most preferably, $R^{33}$ is selected from —O—$CH_3$ or —O—$CH_2$—$CH_3$.

Alternatively, $R^{32}$ and $R^{33}$ jointly form a group —C(halogen)=CH—N($C_{1-4}$ alkyl)-. The $C_{1-4}$ alkyl comprised in that group is preferably selected from methyl or ethyl. The halogen comprised in that group is preferably selected from —F, —Cl, or —Br, and more preferably the halogen is —Cl. That is, $R^{32}$ and $R^{33}$ form a 5-membered ring together with the carbon atoms which they are attached to, wherein $R^{32}$ and $R^{33}$ together are a bivalent group —C(halogen)=CH—N($C_{1-4}$ alkyl)-. It is particularly preferred that $R^{32}$ and $R^{33}$ jointly form a group —C(halogen)=CH—N($CH_3$)— or a group —C(halogen)=CH—N($CH_2CH_3$)—, wherein in each case the halogen is preferably selected from —F, —Cl, or —Br, and more preferably the halogen is —Cl.

$R^{34}$ is selected from —OH, —O($C_{1-4}$ alkyl), —SH, —S($C_{1-4}$alkyl), halogen (particularly —Cl, —Br or —I), —CN, —$CF_3$, —$NH_2$, —NH($C_{1-4}$ alkyl), or —N($C_{1-4}$ alkyl)($C_{1-4}$ alkyl). Preferably, $R^{34}$ is selected from —O($C_{1-4}$ alkyl), —Cl, —Br, —I, or —$NH_2$. More preferably, $R^{34}$ is selected from —O—$CH_3$, —O—$CH_2$—$CH_3$, —Br, —I, or —$NH_2$. Most preferably, $R^{34}$ is selected from —O—$CH_3$, —Br or —I.

In a preferred embodiment, $R^{32}$ is —F and $R^{33}$ is —O—$CH_3$. In a further preferred embodiment, $X^3$ is N($CH_3$), $R^{31}$ is —Br or —I, $R^{32}$ is —F, $R^{33}$ is —O—$CH_3$, and $R^{34}$ is —O—$CH_3$, —Br or —I. Particularly preferred compounds of formula (III) are the following compounds 9a, 9b and 9c:

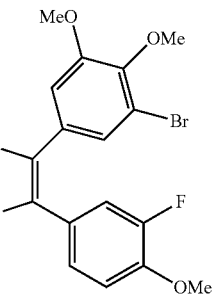

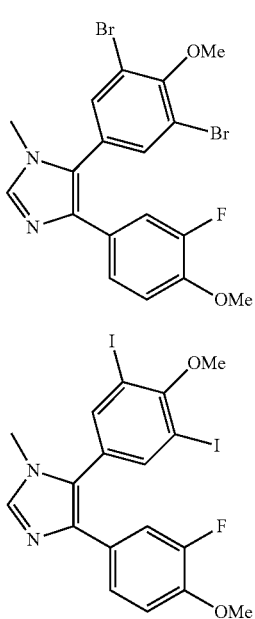

As used herein, the term "alkyl" refers to a monovalent saturated aliphatic (i.e. non-aromatic) acyclic hydrocarbon group (i.e. a group consisting of carbon atoms and hydrogen atoms) which may be linear or branched and does not comprise any carbon-to-carbon double bond or any carbon-to-carbon triple bond. Accordingly, the term "$C_{1-4}$ alkyl" refers to methyl, ethyl, propyl (e.g., n-propyl or isopropyl), or butyl (e.g., n-butyl, isobutyl, tert-butyl, or sec-butyl).

As used herein, the term "halogen" refers to —F, —Cl, —Br, or —I, and in particular to —F, —Cl, or —Br.

The present invention also relates to a pharmaceutical composition comprising a compound of formula (I), (II) or (III) as defined herein or a pharmaceutically acceptable salt, solvate, or prodrug thereof, in combination with a pharmaceutically acceptable excipient. Accordingly, the compounds of formula (I), (II) or (III) are useful as medicaments.

The present invention further relates to a compound of formula (I), (II) or (III) as defined herein, or a pharmaceutically acceptable salt, solvate, or prodrug thereof, or a pharmaceutical composition comprising any of the aforementioned entities in combination with a pharmaceutically acceptable excipient, for use in the treatment or prevention of cancer. The use of the above compound for the preparation of a medicament for the treatment or prevention of cancer is also within the scope of the invention.

Furthermore, the invention encompasses a method of treating or preventing cancer, the method comprising the administration of a compound of formula (I), (II) or (III) as defined herein, or a pharmaceutically acceptable salt, solvate, or prodrug thereof, or a pharmaceutical composition comprising any of the aforementioned entities in combination with a pharmaceutically acceptable excipient, to a subject in need of such a treatment or prevention.

The cancer to be treated or prevented with the compounds or the pharmaceutical compositions according to the present invention includes, for example, breast (mamma) cancer, genitourinary cancer (such as, e.g., prostate tumor, including a hormone-refractory prostate tumor, or germ cell cancer), lung cancer (such as, e.g., small cell or non-small cell lung tumor), gastrointestinal cancer (such as, e.g., hepatocellular carcinoma, colorectal tumor, colon cancer or gastric cancer), epidermoid cancer (such as, e.g., epidermoid head and/or neck tumor or mouth tumor), melanoma, ovarian cancer, pancreas cancer, neuroblastoma, head and/or neck cancer, bladder cancer, renal cancer, brain cancer, leukemia (such as, e.g., lymphocytic leukemia or myelogenous leukemia), or lymphoma.

It is particularly preferred that the cancer to be treated or prevented with the compounds or the pharmaceutical compositions according to the invention is a multidrug-resistant cancer. The cancer to be treated may thus be a multidrug-resistant form of the above described cancers. In a preferred embodiment of the present invention, the cancer to be treated or prevented with the compounds or the pharmaceutical compositions provided herein is resistant against combretastatin A-4 and/or cisplatin. Accordingly, in the present invention the treatment or prevention of combretastatin A-4 (CA-4)-refractory cancer or cisplatin-refractory cancer is particularly envisaged.

Figure 3:
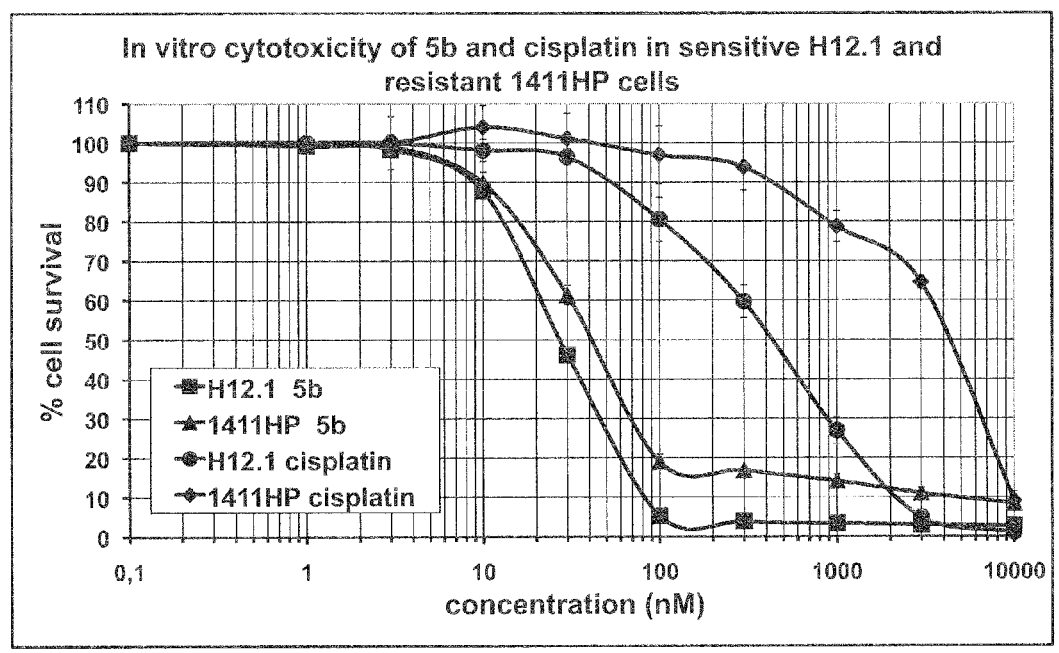
Figure 3:
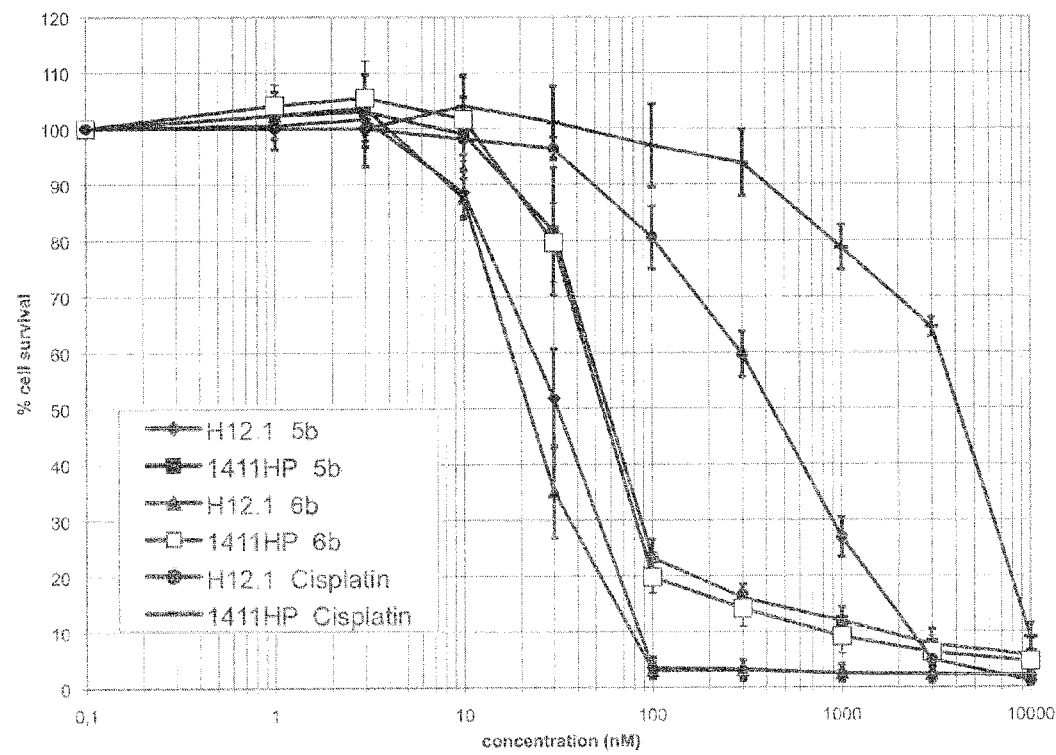
Figure 4:
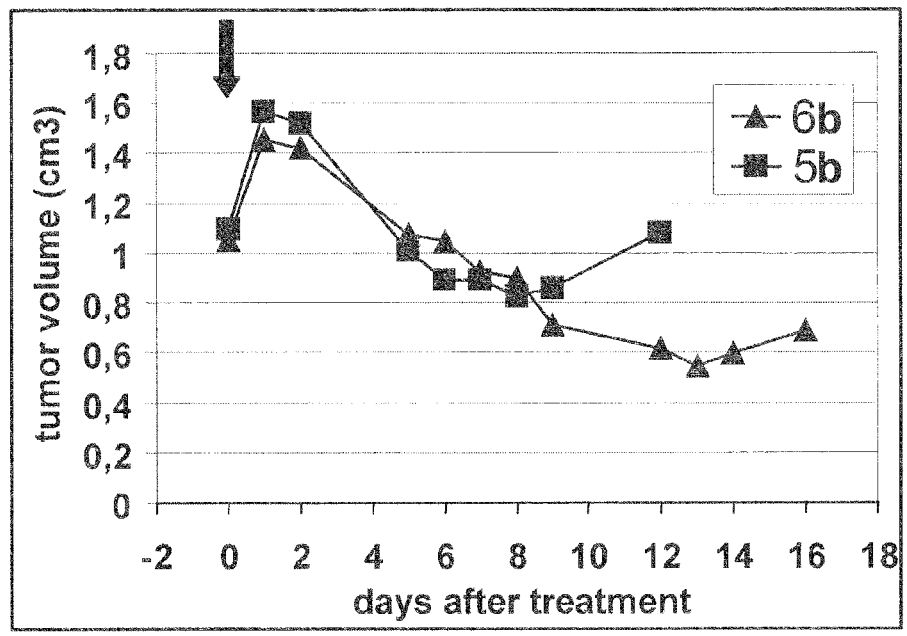
Figure 4:
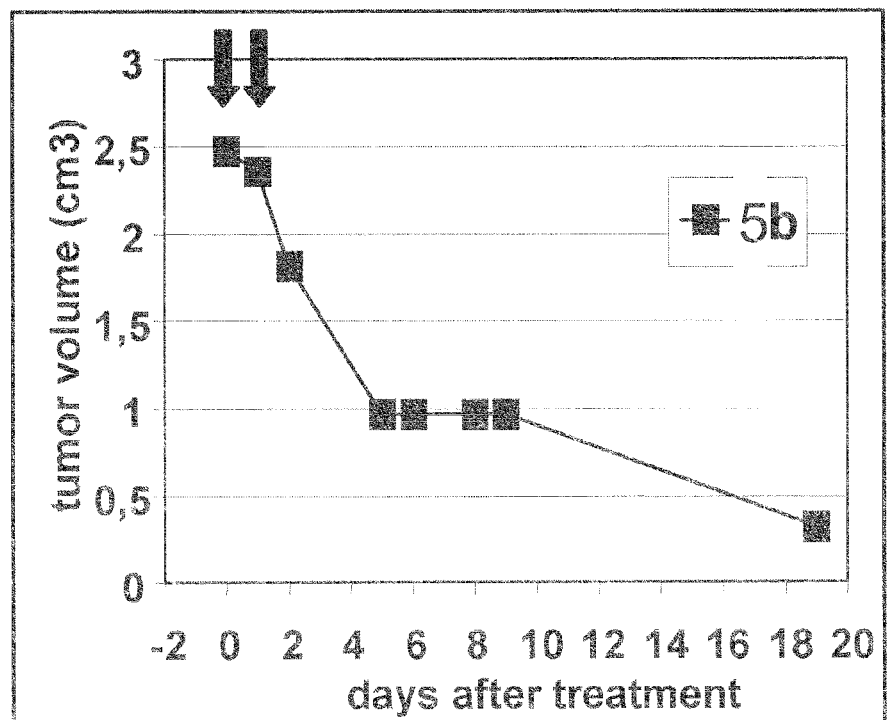
Figure 4:
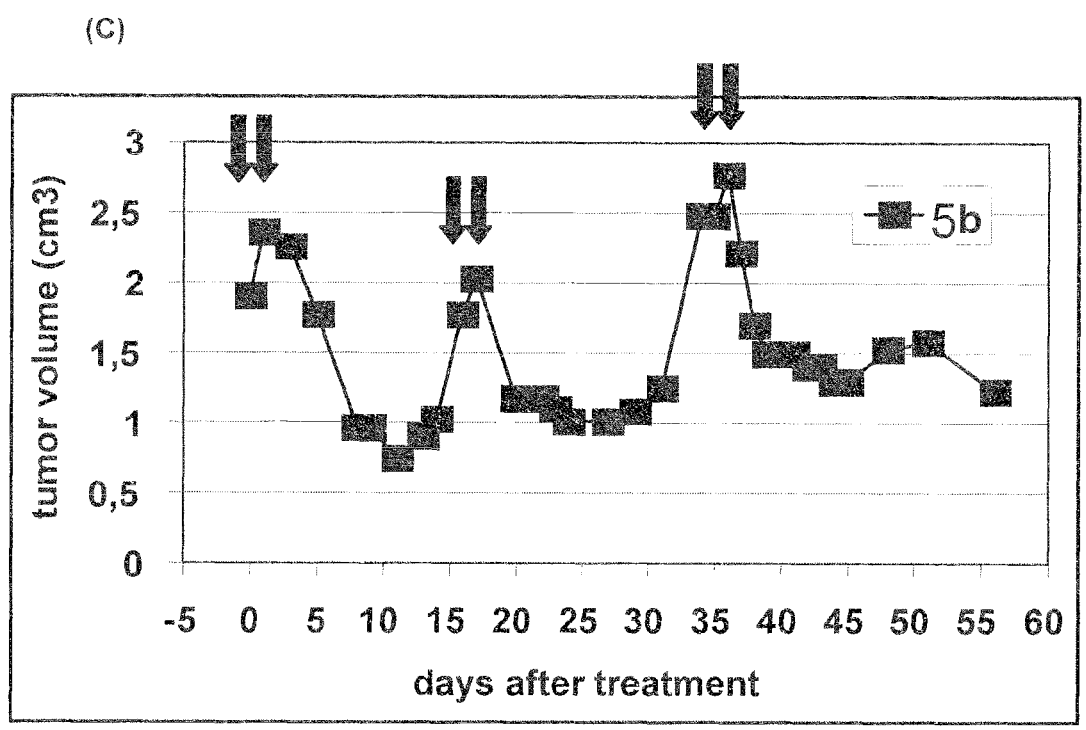
Figure 5:
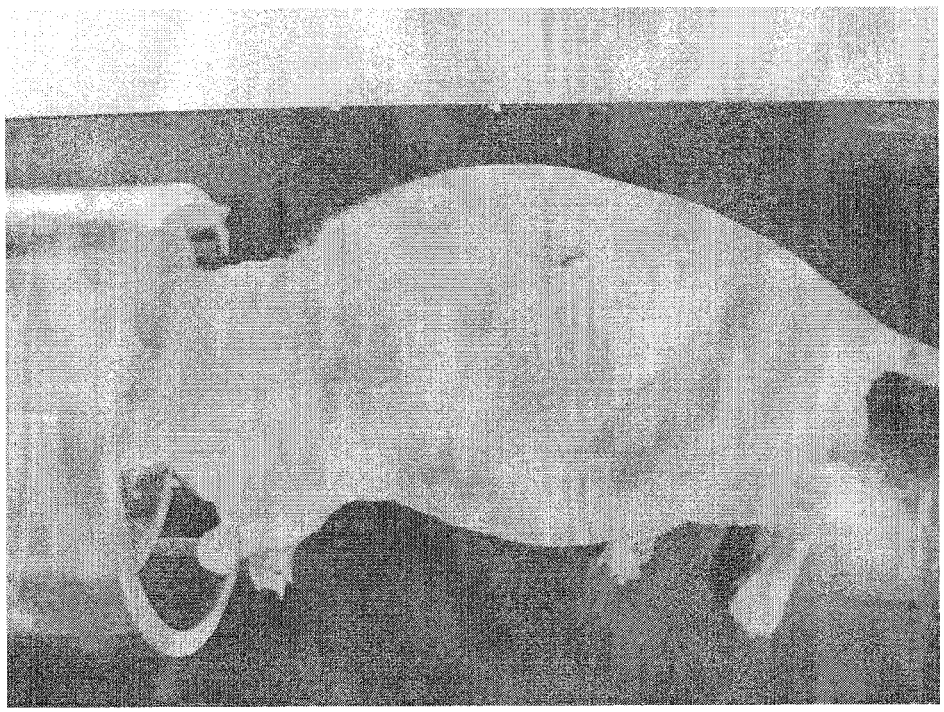
Figure 5:

The compounds according to the invention have been found to be surprisingly effective in the medical intervention of multidrug-resistant cancer and, in particular, of CA4-refractory cancer, which has been demonstrated in vitro and in vivo, including in a mouse xenograft model (cf. Example 3 and FIGS. 3, 4 and 5).

It has been demonstrated that the new compounds exhibit a distinct cytotoxic, antiangiogenic/antivascular and antimitotic effect. In addition, the imidazole/oxazole bridge in the molecular structure of the new compounds gives rise to a stable cis-configuration of the C═C-double bond between the arene rings and thus to a high chemical and pharmacological stability. Any isomerization to a trans-stilben with loss of anti-tumor activity is no longer possible. Moreover, their polar substituents render the new compounds very well soluble in water and so directly applicable without employment of a vehicle. These compounds can be administered by injection as solutions in physiological saline solution. Such solutions were shown to be stable for at least one month under ambient conditions without any noticeable loss of activity. In animal studies of a multi-resistant tumor model the new compounds were found anti-tumor active causing a dramatic regression of the tumor xenografts. The strong antivascular effect selectively affecting the tumoral vasculature was unambiguously confirmed by visible hemorrhages of the tumoral tissue. No unwanted side effects were observed when the new compounds were applied at efficacious concentrations. This underscores their high tumor selectivity and their excellent tolerance in vivo. Thus the attachment of special ring substituents at defined positions, as described herein for the compounds of formula (I), (II) and (III), results in enhanced anti-tumor activity, improved pharmacological properties as well as in superior tolerance in vivo and in the potential to overcome chemoresistance of tumors. Furthermore, the compounds of the invention have surprisingly been found to exhibit a synergistic effect resulting from the combination of a high cytotoxicity and a strong antivascular effect selectively affecting the tumoral vasculature, as also demonstrated in the Examples.

The nature of the halogen substituent in $R^1$ in formula (I) is crucial for the selectivity of the compounds according to the invention and the magnitude of their bioactivity. Unlike its chloro congener 5b (structure shown in Example 4), the bromo imidazole 6b was vascular disrupting in tumor xenografts while leaving regular vasculature in chicken embryos (CAM assay) alone. The compounds of the invention are also characterized by an outstanding tumor-selective cytotoxicity and a strong induction of cancer cell apoptosis.

Figure 2:
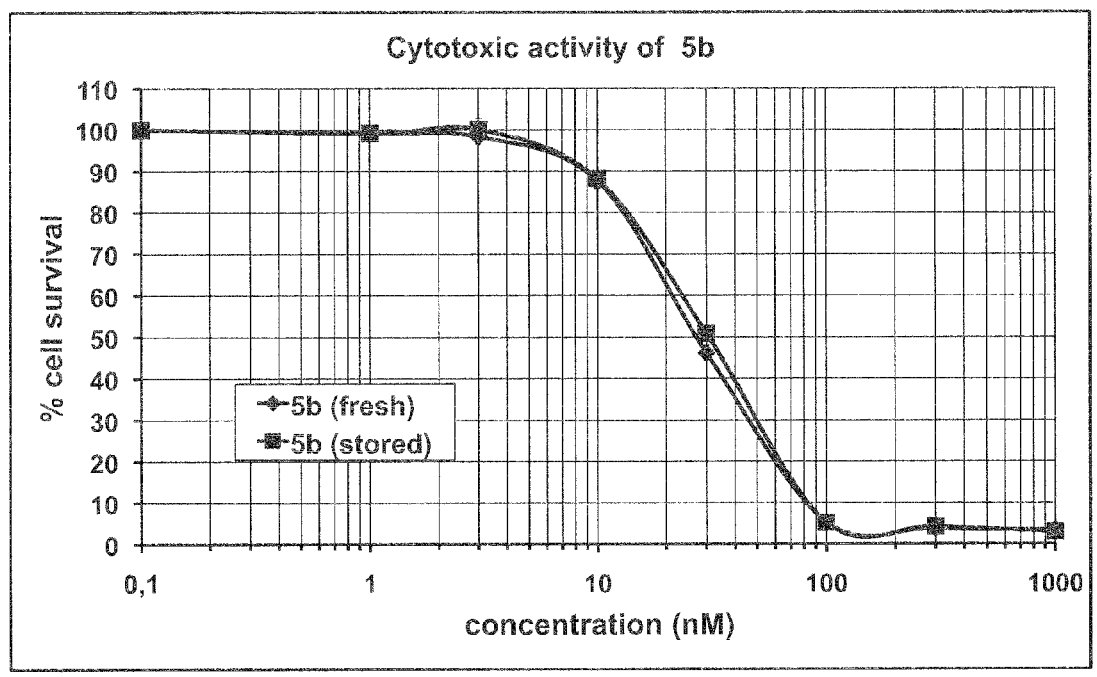

The compounds of the invention, including the compounds of formula (I), further have advantageous properties with respect to solubility in water and chemical stability in solution, as also demonstrated in Example 3 and FIGS. 1 and 2. For example, the solubility of the compounds 5b, 6b and 8a according to the present invention in water exceeded a concentration of 10 mg/mL. Thus, these compounds are even more water-soluble than the potassium salt of combretastatin A-4-phosphate (about 5 mg/mL; Bedford et al., *Bioorg. Med. Chem. Lett.* 1996, 6, 157-160). Also for this reason, the compounds of the invention, including the compounds of formula (I), are particularly suitable and effective as medicaments, including as medicaments in the treatment or prevention of cancer.

Thus, the compounds of the present invention are particularly advantageous in respect of cytotoxicity, solubility in water, and chemical stability, as has been shown in the appended examples for the compound 5b according to the invention. In particular, compound 5b is highly cytotoxic in vitro and in vivo (likewise in CA-4- and cisplatin-resistant cell lines), shows an improved water solubility compared with CA-4-phosphate and can not isomerize to inactive trans-isomers like CA-4. Compound 5b is nevertheless well tolerated and selective in mouse xenografts. The compounds of the present invention can thus be administered without the need of prodrug forms, such as phosphate prodrug forms used for combretastatin-A4. However, in one embodiment prodrugs can be used, if desired.

For a person skilled in the field of synthetic chemistry, various ways for the preparation of the compounds of the present invention, including the compounds of formula (I), (II) or (III), will be readily apparent. For example, the compounds of formula (I) can be prepared according to the following general protocol.

First, the respective para-toluenesulfonylmethylisocyanides (TosMIC derivatives) are prepared (Scheme 1). Commercially available 5-chloro- or 5-bromovanillin 1a/b were reacted with iodomethane and potassium carbonate to give the veratraldehydes 2a/b which were converted to the tosylmethylformamides 3a/b by reaction with para-toluenesulfinic acid and formamide in the presence of camphorsulfonic acid. In the same way, 5-nitrovanillin (1c) as obtained by reaction of vanillin with fuming nitric acid in acetic acid was methylated to give veratraldehyde 2c which was converted to formamide 3c. Subsequently, the formamides 3 were dehydrated to the 3-substituted TosMIC-derivatives 4 by treatment with phosphoroxychloride.

Scheme 1: Synthesis of para-toluenesulfonylmethylisocyanides 4.

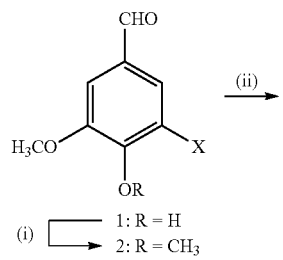

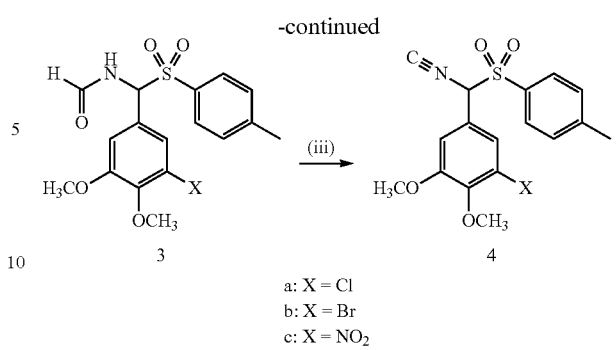

a: X = Cl
b: X = Br
c: X = NO$_2$

Reagents and conditions: (i) CH$_3$I, K$_2$CO$_3$, TBAI, DMF, 20° C., 24 h, 80-90%; (ii) HCONH$_2$, camphorsulfonic acid, para-toluenesulfinic acid, 60° C., 16 h, 51-58%; (iii) POCl$_3$, Et$_3$N, DME, -5° C., 3 h, 57-74%.

The halo-substituted TosMIC derivatives 4a/b are converted to the imidazoles 5/6 by reaction in dimethoxyethane/ethanol mixtures with aryl aldehydes or the imines generated from the latter (Scheme 2). Selective reduction of the nitro group with Zn/HCl affords the desired amines 5b or 6b, respectively. Treatment of the imidazoles 5a-d and 6b-d with 3 M HCl/dioxane yields the respective water-soluble hydrochlorides.

Scheme 2: Synthesis of N-methylimidazole-bridged combretastatin A4-analogs.

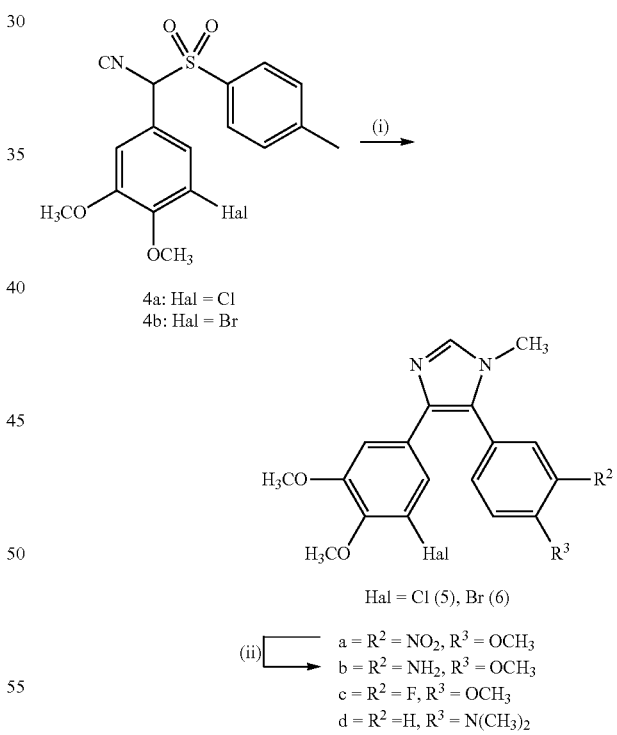

Reagent and conditions: (i) ArCHO, CH$_3$NH$_2$ (33% in ethanol), CH$_3$CO$_2$H, ethanol, reflux, 2 h; then 4a/b, K$_2$CO$_3$, dimethoxyethane/ethanol, reflux, 6 h, 52-99%; (ii) Zn, HCl, THF, 20° C., 10 min, 40-91%.

The nitro-substituted compounds 7a-e are prepared similarly to the imidazoles 5/6 from the nitro-TosMIC derivative 4c and the corresponding aldehydes and imines (Scheme 3). The amines 8a-e are obtained by Pd-catalyzed transfer hydrogenation. The 3-chloroindole 7e is reduced with Zn/HCl to amine 8e. The compounds 8 can further be converted to water-soluble hydrochlorides.

Scheme 3: Synthesis of water-soluble amino substituted oxazoles and N-methylimidazoles 8.

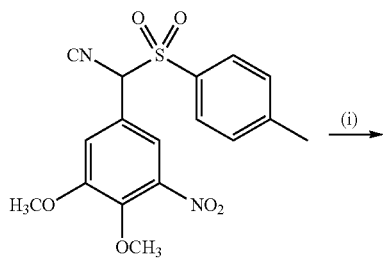

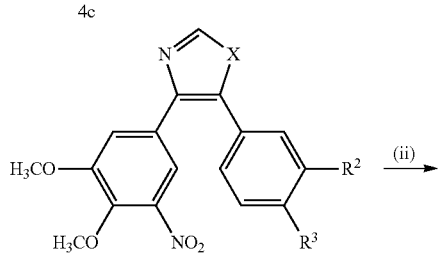

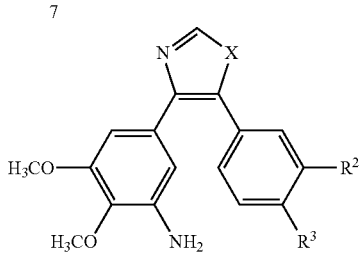

8a = X = O, R² = NH₂, R³ = OCH₃
8b = X = O, R² = H, R³ = N(CH₃)₂
8c = X = NCH₃, R² = OH, R³ = OCH₃
8d = X = NCH₃, R² = F, R³ = OCH₃
8e = X = NCH₃, R²—R³ = CCl═CH—N(CH₃)

Reagent and conditions: (i) ArCHO, K₂CO₃, dimethoxyethane/CH₃OH, reflux, 2 h, 42-86% (for X = O); ArCHO, CH₃NH₂ (33% in ethanol), CH₃CO₂H, ethanol, reflux, 2 h; then 4c, K₂CO₃ dimethoxyethane/ethanol, reflux, 6 h, 64-74% (for X = NCH₃); (ii) HCO₂NH₄, Pd/C (5%), CH₃OH, reflux, 2 h, 67-84% (for 8a-d); Zn, HCl, THF, 20° C., 10 min, 64% (for 8e).

The compounds 5e-g and 6e-g are prepared as follows (Scheme 4). 4-Ethoxy-3-nitro/fluorobenzaldehyde is treated with MeNH₂ to give imine intermediates, which are reacted with the TosMIC reagents 4a/b under basic conditions to give the N-methyl imidazoles 5e,g and 6e,g. The preparation of the amines 5f and 6f is accomplished by reduction of 5e/6e with Zn/HCl in THF. These compounds can be converted into the hydrochloride salts, e.g., by treatment with 3 M HCl/dioxane.

Scheme 4: Synthesis of compounds 5e-g and 6e-g.

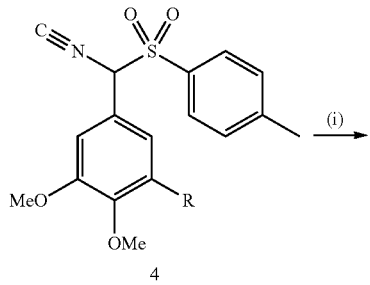

4
a: R = Cl
b: R = Br

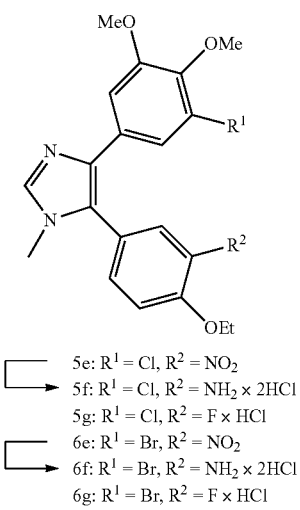

5e: R¹ = Cl, R² = NO₂
5f: R¹ = Cl, R² = NH₂ × 2HCl
5g: R¹ = Cl, R² = F × HCl
6e: R¹ = Br, R² = NO₂
6f: R¹ = Br, R² = NH₂ × 2HCl
6g: R¹ = Br, R² = F × HCl

Reagents and conditions: (i) subst. ArCHO, MeNH₂, AcOH, EtOH, reflux, 2 h, then 4a/b, K₂CO₃, EtOH, reflux, 3 h; (ii) Zn, HCl, THF, r.t., 15 min, then 3M HCl/dioxane, DCM, r.t., 15 min.

Furthermore, the compounds of formula (I) can also be prepared in analogy to the synthesis routes described in Wang et al., *J. Med. Chem.* 2002, 45, 1697-1711.

The compounds of formula (II) or (III) can be prepared in accordance with or in analogy to the syntheses described above and/or in the Examples. The compounds of formula (III), in particular, can also be prepared according to the following general protocol.

The compounds 9a-c are prepared as follows (Scheme 5). 3-Bromo-4,5-dimethoxybenzaldehyde, 3,5-dibromo-4-methoxybenzaldehyde, and 3,5-diiodo-4-methoxybenzaldehyde, respectively, are treated with MeNH₂ to give imine intermediates, which are reacted with the TosMIC reagent 4d under basic conditions to give the N-methyl imidazoles 9a-c. These compounds can be converted to the hydrochloride salts, e.g., by treatment with 3 M HCl/dioxane.

Scheme 5: Synthesis of compounds 9a-c.

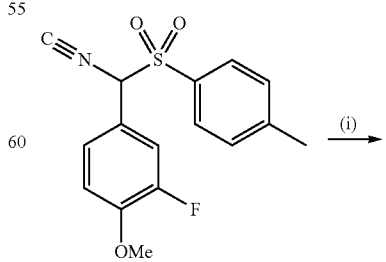

4d

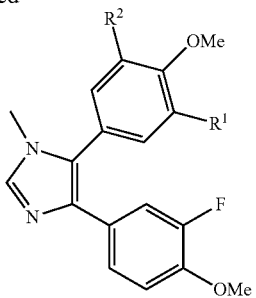

9a = R¹ = Br, R² = OMe
9b = R¹, R² = Br
9c = R¹ = R² = I

Reagent and conditions: (i) subst. ArCHO, MeNH₂, AcOH, EtOH, reflux, 2 h, then 4d, K₂CO₃, EtOH, reflux, 3h.

The scope of the invention embraces all pharmaceutically acceptable salt forms of the compounds of the present invention, in particular the compounds of formula (I), (II) or (III), which may be formed, e.g., by protonation of an atom carrying an electron lone pair which is susceptible to protonation, such as an amino group, with an inorganic or organic acid, or as a salt of a carboxylic acid group with a physiologically acceptable cation as they are well known in the art. Exemplary base addition salts comprise, for example, alkali metal salts such as sodium or potassium salts; alkaline earth metal salts such as calcium or magnesium salts; ammonium salts; aliphatic amine salts such as trimethylamine, triethylamine, dicyclohexylamine, ethanolamine, diethanolamine, triethanolamine, procaine salts, meglumine salts, diethanol amine salts or ethylenediamine salts; aralkyl amine salts such as N,N-dibenzylethylenediamine salts, benetamine salts; heterocyclic aromatic amine salts such as pyridine salts, picoline salts, quinoline salts or isoquinoline salts; quaternary ammonium salts such as tetramethylammonium salts, tetraethylammonium salts, benzyltrimethylammonium salts, benzyltriethylammonium salts, benzyltributylammonium salts, methyltrioctylammonium salts or tetrabutylammonium salts; and basic amino acid salts such as arginine salts or lysine salts. Exemplary acid addition salts comprise, for example, mineral acid salts such as hydrochloride, hydrobromide, hydroiodide, sulfate salts, nitrate salts, phosphate salts (such as, e.g., phosphate, hydrogenphosphate, or dihydrogenphosphate salts), carbonate salts, hydrogencarbonate salts or perchlorate salts; organic acid salts such as acetate, propionate, butyrate, pentanoate, hexanoate, heptanoate, octanoate, cyclopentanepropionate, undecanoate, lactate, maleate, oxalate, fumarate, tartrate, malate, citrate, nicotinate, benzoate, salicylate or ascorbate salts; sulfonate salts such as methanesulfonate, ethanesulfonate, 2-hydroxyethanesulfonate, benzenesulfonate, p-toluenesulfonate (tosylate), 2-naphthalenesulfonate, 3-phenylsulfonate, or camphorsulfonate salts; and acidic amino acid salts such as aspartate or glutamate salts.

Moreover, the scope of the invention embraces solid forms of the compounds of formula (I), (II) or (III) in any solvated form, including e.g. solvates with water, for example hydrates, or with organic solvents such as, e.g., methanol, ethanol or acetonitrile, i.e. as a methanolate, ethanolate or acetonitrilate, respectively; or in the form of any polymorph.

Furthermore, the formulas in the present application are intended to cover all possible stereoisomers, including enantiomers and diastereomers, of the indicated compounds.

Thus, all stereoisomers of the compounds of formula (I), (II) or (III) are contemplated as part of the present invention, either in admixture or in pure or substantially pure form. The scope of the compounds according to the invention embraces all the possible stereoisomers and their mixtures. It particularly embraces the racemic forms and the isolated optical isomers. The racemic forms can be resolved by physical methods, such as, e.g., fractional crystallization, separation or crystallization of diastereomeric derivatives or separation by chiral column chromatography. The individual optical isomers can be obtained from the racemates using conventional methods, such as, e.g., salt formation with an optically active acid followed by crystallization.

Pharmaceutically acceptable prodrugs of the compounds of formula (I), (II) or (III) are derivatives which have chemically or metabolically cleavable groups and become, by solvolysis or under physiological conditions, the compounds of the present invention which are pharmaceutically active in vivo. Prodrugs of the compounds of formula (I), (II) or (III) may be formed in a conventional manner with a functional group of the compounds such as with an amino or a hydroxyl group. The prodrug derivative form often offers advantages of solubility, tissue compatibility or delayed release in a mammalian organism (see, Bundgaard, H., Design of Prodrugs, pp. 7-9, 21-24, Elsevier, Amsterdam 1985). When a compound employed in the present invention has a hydroxyl group, an acyloxy derivative prepared by reacting the hydroxyl group with a suitable acylhalide or a suitable acid anhydride is exemplified as a prodrug. An especially preferred acyloxy derivative as a prodrug is —OC(=O)—CH₃, —OC(=O)—C₂H₅, —OC(=O)-(tert-Bu), —OC(=O)—C₁₅H₃₁, —OC(=O)-(m-COONa-Ph), —OC(=O)—CH₂CH₂COONa, —O(C=O)—CH(NH₂)CH₃ or —OC(=O)—CH₂—N(CH₃)₂. When a compound employed in the present invention has an amino group, an amide derivative prepared by reacting the amino group with a suitable acid halide or a suitable mixed anhydride is exemplified as a prodrug. An especially preferred amide derivative as a prodrug is —NHC(=O)—(CH₂)₂OCH₃ or —NHC(=O)—CH(NH₂)CH₃. Accordingly, the compound of formula (I) may be used as a prodrug, wherein the prodrug is a compound of formula (I), in which one or more amino groups, if present, are in the form of an amide, such as e.g. in the form of —NHC(=O)—(CH₂)₂OCH₃ or —NHC(=O)—CH(NH₂)CH₃, or in which one or more hydroxyl groups, if present, are in the form of an acyloxy, such as e.g. in the form of —OC(=O)—CH₃, —OC(=O)—C₂H₅, —OC(=O)-(tert-Bu), —OC(=O)—C₁₅H₃₁, —OC(=O)-(m-COONa-Ph), —OC(=O)—CH₂CH₂COONa, —O(C=O)—CH(NH₂)CH₃ or —OC(=O)—CH₂—N(CH₃)₂, or in the form of a phosphate, i.e. in the form of —O—P(=O)(O—)₂, or a phosphate salt (such as, e.g., the base addition salts described herein above). Thus, if R² and/or R³ in the compound of formula (I) is —OH (i.e., hydroxyl), then a corresponding prodrug may be the compound of formula (I), in which the hydroxyl group which is R² (if applicable) and/or the hydroxyl group which is R³ (if applicable) is in the form of a phosphate (i.e. in the form of —O—P(=O)(O—)₂), a phosphate salt, or an acyloxy, preferably in the form of a phosphate or a phosphate salt (e.g., with sodium, potassium, or any of the cations referred to in respect of the base addition salts described herein above). A preferred prodrug of the compounds of the present invention is a compound of formula (I), in which R² is —O—P(=O)(OH)₂ or a salt thereof (e.g., a disodium or a dipotassium salt).

The compounds described herein may be administered as compounds per se or may be formulated as medicaments. The medicaments/pharmaceutical compositions may optionally comprise one or more pharmaceutically acceptable excipients, such as carriers, diluents, fillers, disintegrants, lubricating agents, binders, colorants, pigments, stabilizers, preservatives, antioxidants, or solubility enhancers.

In particular, the pharmaceutical compositions may comprise one or more solubility enhancers, such as, e.g., poly (ethylene glycol), including poly(ethylene glycol) having a molecular weight in the range of about 200 to about 5,000 Da, ethylene glycol, propylene glycol, non-ionic surfactants, tyloxapol, polysorbate 80, macrogol-15-hydroxystearate, phospholipids, lecithin, dimyristoyl phosphatidylcholine, dipalmitoyl phosphatidylcholine, distearoyl phosphatidylcholine, cyclodextrins, hydroxyethyl-β-cyclodextrin, hydroxypropyl-β-cyclodextrin, hydroxyethyl-γ-cyclodextrin, hydroxypropyl-γ-cyclodextrin, dihydroxypropyl-β-cyclodextrin, glucosyl-α-cyclodextrin, glucosyl-β-cyclodextrin, diglucosyl-β-cyclodextrin, maltosyl-α-cyclodextrin, maltosyl-β-cyclodextrin, maltosyl-γ-cyclodextrin, maltotriosyl-β-cyclodextrin, maltotriosyl-γ-cyclodextrin, dimaltosyl-β-cyclodextrin, methyl-β-cyclodextrin, carboxyalkyl thioethers, hydroxypropyl methylcelilulose, hydroxypropylcellulose, polyvinylpyrrolidone, vinyl acetate copolymers, vinyl pyrrolidone, sodium lauryl sulfate, dioctyl sodium sulfosuccinate, or any combination thereof.

The pharmaceutical compositions can be formulated by techniques known to the person skilled in the art, such as the techniques published in Remington's Pharmaceutical Sciences, 20$^{th}$ Edition. The pharmaceutical compositions can be formulated as dosage forms for oral, parenteral, such as intramuscular, intravenous, intraperitoneal, subcutaneous, intradermal, intraarterial, rectal, nasal, topical, aerosol or vaginal administration. Dosage forms for oral administration include coated and uncoated tablets, soft gelatin capsules, hard gelatin capsules, lozenges, troches, solutions, emulsions, suspensions, syrups, elixirs, powders and granules for reconstitution, dispersible powders and granules, medicated gums, chewing tablets and effervescent tablets. Dosage forms for parenteral administration include solutions, emulsions, suspensions, dispersions and powders and granules for reconstitution. Emulsions are a preferred dosage form for parenteral administration. Dosage forms for rectal and vaginal administration include suppositories and ovula. Dosage forms for nasal administration can be administered via inhalation and insufflation, for example by a metered inhaler. Dosage forms for topical administration include creams, gels, ointments, salves, patches and transdermal delivery systems.

The compounds of formula (I), (II) or (III) or the above described pharmaceutical compositions comprising a compound of formula (I), (II) or (III) may be administered to a subject by any convenient route of administration, whether systemically/peripherally or at the site of desired action, including but not limited to one or more of: oral (e.g. as a tablet, capsule, or as an ingestible solution), topical (e.g., transdermal, intranasal, ocular, buccal, and sublingual), parenteral (e.g., using injection techniques or infusion techniques, and including, for example, by injection, e.g. subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, or intrasternal by, e.g., implant of a depot, for example, subcutaneously or intramuscularly), pulmonary (e.g., by inhalation or insufflation therapy using, e.g., an aerosol, e.g. through mouth or nose), gastrointestinal, intrauterine, intraocular, subcutaneous, ophthalmic (including intravitreal or intracameral), rectal, and vaginal. In particular, the compounds or the pharmaceutical compositions may be administered orally or by inhalation. It is particularly preferred that the compounds of the present invention are administered by pulmonary administration, in particular by inhalation, in the form of dry powder formulations as described e.g. in more detail herein below.

If the compounds or pharmaceutical compositions are administered parenterally, then examples of such administration include one or more of: intravenously, intraarterially, intraperitoneally, intrathecally, intraventricularly, intraurethrally, intrasternally, intracranially, intramuscularly or subcutaneously administering the compounds pharmaceutical compositions, and/or by using infusion techniques. For parenteral administration, the compounds are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

The compounds or pharmaceutical compositions can also be administered orally in the form of tablets, capsules, ovules, elixirs, solutions or suspensions, which may contain flavoring or coloring agents, for immediate-, delayed-, modified-, sustained-, pulsed- or controlled-release applications.

The tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycolate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included. Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavoring agents, coloring matter or dyes, with emulsifying and/or suspending agents and with diluents such as water, ethanol, propylene glycol and glycerin, and combinations thereof.

Alternatively, the compounds or pharmaceutical compositions can be administered in the form of a suppository or pessary, or it may be applied topically in the form of a gel, hydrogel, lotion, solution, cream, ointment or dusting powder. The compounds of the present invention may also be dermally or transdermally administered, for example, by the use of a skin patch.

The compounds or pharmaceutical compositions may also be administered by the pulmonary route, rectal routes, or the ocular route. For ophthalmic use, they can be formulated as micronized suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

It is furthermore envisaged to prepare dry powder formulations of the compounds of the present invention for pulmonary administration. The dry powder formulations of the compounds of the present invention may be delivered using any suitable dry powder inhaler (DPI), i.e., an inhaler device that utilizes the patient's inhaled breath as a vehicle to transport the dry powder drug to the lungs.

For topical application to the skin, the compounds or pharmaceutical compositions can be formulated as a suitable ointment containing the active compound suspended or dissolved in, for example, a mixture with one or more of the following: mineral oil, liquid petrolatum, white petrolatum, propylene glycol, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, 2-octyldodecanol, benzyl alcohol and water.

Typically, a physician will determine the actual dosage which will be most suitable for an individual subject. The specific dose level and frequency of dosage for any particular individual subject may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual subject undergoing therapy.

A proposed, yet non-limiting dose of the compounds of the invention, including the compounds of formula (I), (II) or (III), for administration to a human (of approximately 70 kg body weight) may be 0.1 µg to 10 g, preferably 0.1 mg to 1 g, and more preferably about 200 mg or more (e.g., 200 to 300 mg or 200 to 500 mg), of the active ingredient per unit dose. The unit dose may be administered, for example, 1 to 4 times per week. The dose will depend on the route of administration. It will be appreciated that it may be necessary to make routine variations to the dosage depending on the age and weight of the patient/subject as well as the severity of the condition to be treated. The precise dose and route of administration will ultimately be at the discretion of the attendant physician or veterinarian.

In one embodiment, the compounds according to the present invention can be used in combination with other therapeutic agents. When the compound is used in combination with a second therapeutic agent active against the same disease, the dose of each compound may differ from that when the compound is used alone. The combination of a compound of this invention with (an) other drug(s) may comprise the administration of the drug(s) with the compound of the invention. Such an administration may comprise simultaneous/concomitant administration. However, sequential/separate administration is also envisaged.

Preferably, the second therapeutic agent to be administered in combination with the compound of the present invention is an anticancer drug. The anticancer drug to be administered in combination with the compound of the invention may be: a tumor angiogenesis inhibitor (for example, a protease inhibitor, an epidermal growth factor receptor kinase inhibitor, or a vascular endothelial growth factor receptor kinase inhibitor); a cytotoxic drug (for example, an antimetabolite, such as purine and pyrimidine analogue antimetabolites); an antimitotic agent (for example, a microtubule stabilizing drug or an antimitotic alkaloid); a platinum coordination complex; an anti-tumor antibiotic; an alkylating agent (for example, a nitrogen mustard or a nitrosourea); an endocrine agent (for example, an adrenocorticosteroid, an androgen, an anti-androgen, an estrogen, an anti-estrogen, an aromatase inhibitor, a gonadotropin-releasing hormone agonist, or a somatostatin analogue); or a compound that targets an enzyme or receptor that is overexpressed and/or otherwise involved in a specific metabolic pathway that is misregulated in the tumor cell (for example, ATP and GTP phosphodiesterase inhibitors, histone deacetylase inhibitors, protein kinase inhibitors (such as serine, threonine and tyrosine kinase inhibitors (for example, Abelson protein tyrosine kinase)) and the various growth factors, their receptors and kinase inhibitors therefor (such as epidermal growth factor receptor kinase inhibitors, vascular endothelial growth factor receptor kinase inhibitors, fibroblast growth factor inhibitors, insulin-like growth factor receptor inhibitors and platelet-derived growth factor receptor kinase inhibitors)); methionine; aminopeptidase inhibitors; proteasome inhibitors; cyclooxygenase inhibitors (for example, cyclooxygenase-1 or cyclooxygenase-2 inhibitors); or topoisomerase inhibitors (for example, topoisomerase I inhibitors or topoisomerase II inhibitors).

An alkylating agent which can be used as an anticancer drug in combination with a compound of the present invention may be, for example, a nitrogen mustard (such as cyclophosphamide, mechlorethamine (chlormethine), uramustine, melphalan, chlorambucil, ifosfamide, bendamustine, or trofosfamide), a nitrosourea (such as carmustine, streptozocin, fotemustine, lomustine, nimustine, prednimustine, ranimustine, or semustine), an alkyl sulfonate (such as busulfan, mannosulfan, or treosulfan), an aziridine (such as hexamethylmelamine (altretamine), triethylenemelamine, ThioTEPA (N,N'N'-triethylenethiophosphoramide), carboquone, or triaziquone), a hydrazine (such as procarbazine), a triazene (such as dacarbazine), or an imidazotetrazines (such as temozolomide).

A platinum coordination complex which can be used as an anticancer drug in combination with a compound of the present invention may be, for example, cisplatin, carboplatin, nedaplatin, oxaliplatin, satraplatin, or triplatin tetranitrate.

A cytotoxic drug which can be used as an anticancer drug in combination with a compound of the present invention may be, for example, an antimetabolite, including folic acid analogue antimetabolites (such as aminopterin, methotrexate, pemetrexed, or raltitrexed), purine analogue antimetabolites (such as cladribine, clofarabine, fludarabine, 6-mercaptopurine (including its prodrug form azathioprine), pentostatin, or 6-thioguanine), and pyrimidine analogue antimetabolites (such as cytarabine, decitabine, 5-fluorouracil (including its prodrug forms capecitabine and tegafur), floxuridine, gemcitabine, enocitabine, or sapacitabine).

An antimitotic agent which can be used as an anticancer drug in combination with a compound of the present invention may be, for example, a taxane (such as docetaxel, larotaxel, ortataxel, paclitaxel/taxol, or tesetaxel), a Vinca alkaloid (such as vinblastine, vincristine, vinflunine, vindesine, or vinorelbine), an epothilone (such as epothilone A, epothilone B, epothilone C, epothilone D, epothilone E, or epothilone F) or an epothilone B analogue (such as ixabepilone/azaepothilone B).

An anti-tumor antibiotic which can be used as an anticancer drug in combination with a compound of the present invention may be, for example, an anthracycline (such as aclarubicin, daunorubicin, doxorubicin, epirubicin, idarubicin, amrubicin, pirarubicin, valrubicin, or zorubicin), an anthracenedione (such as mitoxantrone, or pixantrone) or an anti-tumor antibiotic isolated from *Streptomyces* (such as actinomycin (including actinomycin D), bleomycin, mitomycin (including mitomycin C), or plicamycin).

A tyrosine kinase inhibitor which can be used as an anticancer drug in combination with a compound of the present invention may be, for example, axitinib, bosutinib, cediranib, dasatinib, erlotinib, gefitinib, imatinib, lapatinib, lestaurtinib, nilotinib, semaxanib, sorafenib, sunitinib, or vandetanib.

A topoisomerase-inhibitor which can be used as an anticancer drug in combination with a compound of the present invention may be, for example, a topoisomerase I inhibitor (such as irinotecan, topotecan, camptothecin, belotecan, rubitecan, or lamellarin D) or a topoisomerase II inhibitor (such as amsacrine, etoposide, etoposide phosphate, teniposide, or doxorubicin).

Further anticancer drugs may be used in combination with a compound of the present invention. The anticancer drugs may comprise biological or chemical molecules, like TNF-related apoptosis-inducing ligand (TRAIL), tamoxifen, amsacrine, bexarotene, estramustine, irofulven, trabectedin, cetuximab, panitumumab, tositumomab, alemtuzumab, bevacizumab, edrecolomab, gemtuzumab, alvocidib, seliciclib, aminolevulinic acid, methyl aminolevulinate, efaproxiral, porfimer sodium, talaporfin, temoporfin, verteporfin, alitretinoin, tretinoin, anagrelide, arsenic trioxide, atrasentan, bortezomib, carmofur, celecoxib, demecolcine, elesclomol, elsamitrucin, etoglucid, lonidamine, lucanthone, masoprocol, mitobronitol, mitoguazone, mitotane, oblimersen, omacetaxine, sitimagene, ceradenovec, tegafur, testolactone, tiazofurine, tipifarnib, and vorinostat.

Also biological drugs, like antibodies, antibody fragments, antibody constructs (for example, single-chain constructs), and/or modified antibodies (like CDR-grafted antibodies, humanized antibodies, "full humanized" antibodies, etc.) directed against cancer or tumor markers/factors/cytokines involved in proliferative diseases can be employed in co-therapy approaches with the compounds of the invention. Examples of such biological molecules are anti-HER2 antibodies (e.g. trastuzumab, Herceptin®), anti-CD20 antibodies (e.g. Rituximab, Rituxan®, MabThera®, Reditux®), anti-CD19/CD3 constructs (see, e.g., EP-A-1 071 752) and anti-TNF antibodies (see, e.g., Taylor et al., Antibody therapy for rheumatoid arthritis, *Curr Opin Pharmacol,* 2003, 3(3), 323-328). Further antibodies, antibody fragments, antibody constructs and/or modified antibodies to be used in co-therapy approaches with the compounds of the invention can be found in: Taylor et al., Antibody therapy for rheumatoid arthritis, *Curr Opin Pharmacol,* 2003, 3(3), 323-328; or Roxana et al., *Maedica,* 2006, 1(1), 63-65.

The combinations referred to above may conveniently be presented for use in the form of a pharmaceutical formulation. The individual components of such combinations may be administered either sequentially or simultaneously/concomitantly in separate or combined pharmaceutical formulations by any convenient route. When administration is sequential, either the present compound or the second therapeutic agent may be administered first. When administration is simultaneous, the combination may be administered either in the same or different pharmaceutical composition. When combined in the same formulation it will be appreciated that the two compounds must be stable and compatible with each other and the other components of the formulation. When formulated separately they may be provided in any convenient formulation, conveniently in such manner as are known for such compounds in the art.

In another embodiment, the compounds of the present invention are administered in combination with physical therapy, such as radiotherapy. Radiotherapy may commence before, after, or simultaneously with administration of the compounds. For example, radiotherapy may commence 1 to 10 minutes, 1 to 10 hours or 24 to 72 hours after administration of the compounds. Yet, these time frames are not to be construed as limiting. The subject is exposed to radiation, preferably gamma radiation, whereby the radiation may be provided in a single dose or in multiple doses that are administered over several hours, days and/or weeks. Gamma radiation may be delivered according to standard radiotherapeutic protocols using standard dosages and regimens. Without being bound by theory, the compounds of the present invention may be used to render cells, in particular undesired proliferative/hyperproliferative cells like cancer or tumor cells, more susceptible to such a physical therapy, e.g. radiotherapy.

Accordingly, the present invention relates to a compounds of formula (I), (II) or (III) or a pharmaceutically acceptable salt, solvate, or prodrug thereof, or a pharmaceutical composition comprising any of the aforementioned entities in combination with a pharmaceutically acceptable excipient, for use in the treatment or prevention of cancer, whereby the compound or the pharmaceutical composition is to be administered in combination with an anti-proliferative drug, an anticancer drug, a cytostatic drug, a cytotoxic drug and/or radiotherapy.

Furthermore, it is particularly envisaged to use the combination therapy as described herein above for the treatment or prevention of multidrug-resistant cancer, including the specific multidrug-resistant cancers described above.

The subject or patient, such as the subject in need of treatment or prevention, may be an animal, a vertebrate animal, a mammal, a rodent (e.g. a guinea pig, a hamster, a rat, a mouse), a murine (e.g. a mouse), a canine (e.g. a dog), a feline (e.g. a cat), an equine (e.g. a horse), a primate, a simian (e.g. a monkey or ape), a monkey (e.g. a marmoset, a baboon), an ape (e.g. gorilla, chimpanzee, orangutang, gibbon), or a human. The meaning of the terms "animal", "mammal", etc. is well known in the art and can, for example, be deduced from Wehner und Gehring (1995; Thieme Verlag). In the context of this invention, it is particularly envisaged that animals are to be treated which are economically, agronomically or scientifically important. Scientifically important organisms include, but are not limited to, mice, rats, rabbits, fruit flies like *Drosophila melagonaster* and nematodes like *Caenorhabditis elegans*. Non-limiting examples of agronomically important animals are sheep, cattle and pig, while, for example, cats and dogs may be considered as economically important animals. Preferably, the subject/patient is a mammal. More preferably, the subject/patient is a human.

The term "treatment of a disorder or disease" as used herein, e.g., in the case of the treatment of cancer, is well known in the art. "Treatment of a disorder or disease" implies that a disorder or disease has been diagnosed in a patient/subject. A patient/subject suspected of suffering from a disorder or disease typically shows specific clinical and/or pathological symptoms which a skilled person can easily attribute to a specific pathological condition (i.e. make a diagnosis of a disorder or disease).

"Treatment of a disorder or disease" may, for example, lead to a halt in the progression of the disorder or disease (e.g., no deterioration of symptoms) or a delay in the progression of the disorder or disease (in case the halt in progression is of a transient nature only). "Treatment of a disorder or disease" may also lead to a partial response (e.g., amelioration of symptoms) or complete response (e.g., disappearance of symptoms) of the subject/patient suffering from the disorder or disease. "Amelioration" of a disorder or disease may, for example, lead to a halt in the progression of the disorder or disease or a delay in the progression of the disorder or disease. Such a partial or complete response may be followed by a relapse. It is to be understood that a subject/patient may experience a broad range of responses to a treatment (e.g., the exemplary responses as described herein above).

Treatment of a disorder or disease may, inter alia, comprise curative treatment (preferably leading to a complete response and eventually to healing of the disorder or disease) and palliative treatment (including symptomatic relief).

Also the term "prevention of a disorder or disease" as used herein, e.g., in the case of the prevention of cancer, is well known in the art. For example, a patient/subject suspected of being prone to suffer from a disorder or disease as defined herein may, in particular, benefit from a prevention of the disorder or disease. The subject/patient may have a susceptibility or predisposition for a disorder or disease, including but not limited to hereditary predisposition. Such a predisposition can be determined by standard assays, using, for example, genetic markers or phenotypic indicators. It is to be understood that a disorder or disease to be prevented in accordance with the present invention has not been diagnosed or cannot be diagnosed in the patient/subject (for example, the patient/subject does not show any clinical or pathological symptoms). Thus, the term "prevention" comprises the use of compounds of the present invention before any clinical and/or pathological symptoms are diagnosed or determined or can be diagnosed or determined by the attending physician.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

The invention is also illustrated by the following illustrative figures. The appended figures show:

FIG. 1: Inhibition of tubulin polymerization by 5b (freshly prepared solution vs solution having been stored for one month). Compound 5b effectively inhibits the polymerization of tubulin. No loss of activity is observed over time. (Test: Tubulin-Polymerization assay).

FIG. 2: Cytotoxic activity of 5b (freshly prepared solution vs solution having been stored for one month). The persistence of efficacy is proof of the chemical stability of 5b when dissolved (Test: SRB-cytotoxicity assay).

FIG. 3: Comparison of the in vitro cytotoxicities of 5b and cisplatin (A) or of 5b, 6b and cisplatin (B). Treatment with 5b or 6b results in a breach of the multi-drug resistance of 1411HP cells (Test: SRB-cytotoxicity assay).

FIG. 4: In vivo anti-tumor activity of compounds 5b and 6b in mouse xenografts of multi-resistant germ cell tumor cell line 1411HP. The tumor response following single-dose (A) and dual-dose (B) applications of test compounds, and the tumor response to repeated applications (C) are shown. Arrows indicate the administration of test compounds.

FIG. 5: Vascular disrupting effect of 5b. The distinct vascular disrupting effect selectively affecting the tumoral vasculature is apparent from hemorrhages leading to red-blue to brown coloring of the entire tumor (A: before treatment; B: 24 hours after start of treatment) (Test: subcutaneous tumor xenografts in a nude mouse model; mice were anesthesized for the imaging).

Figure 6:
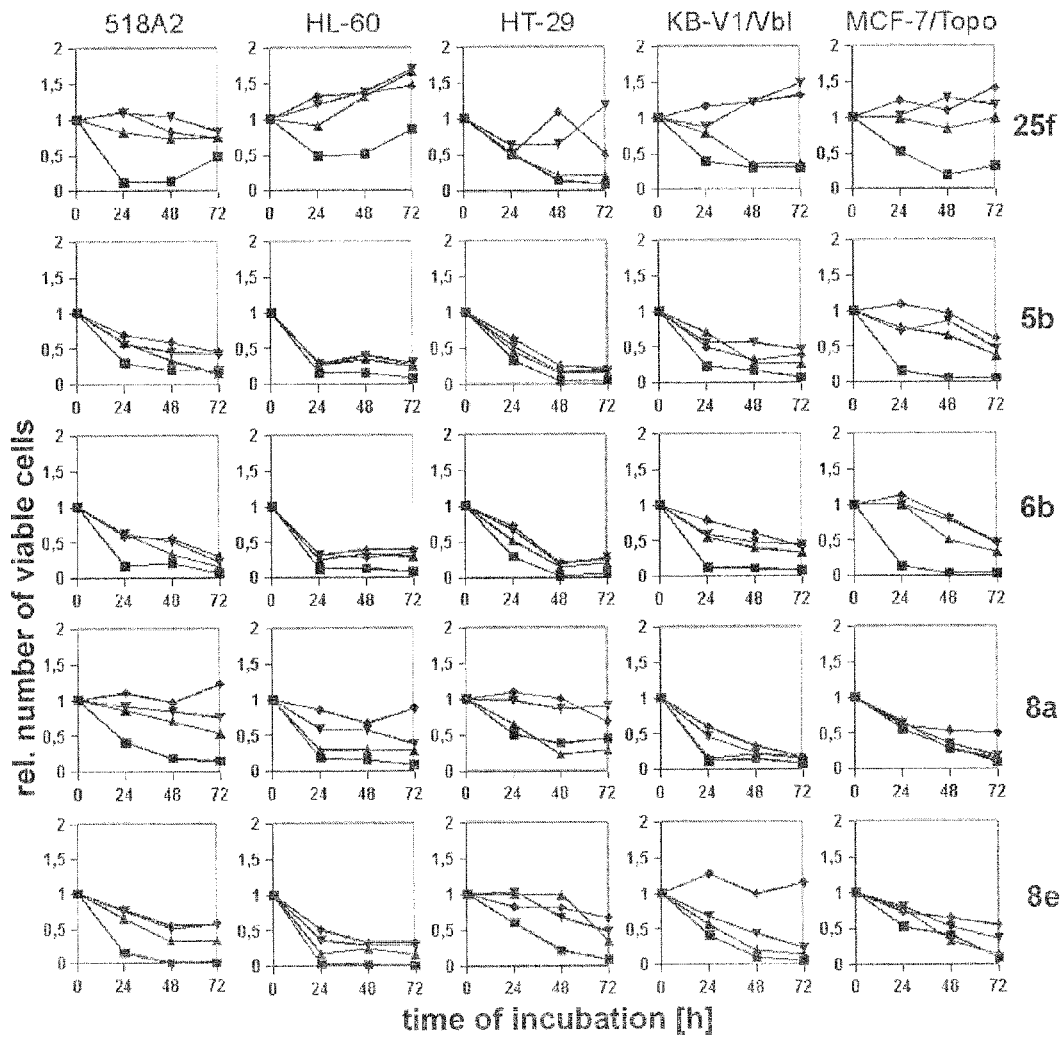
Figure 6:
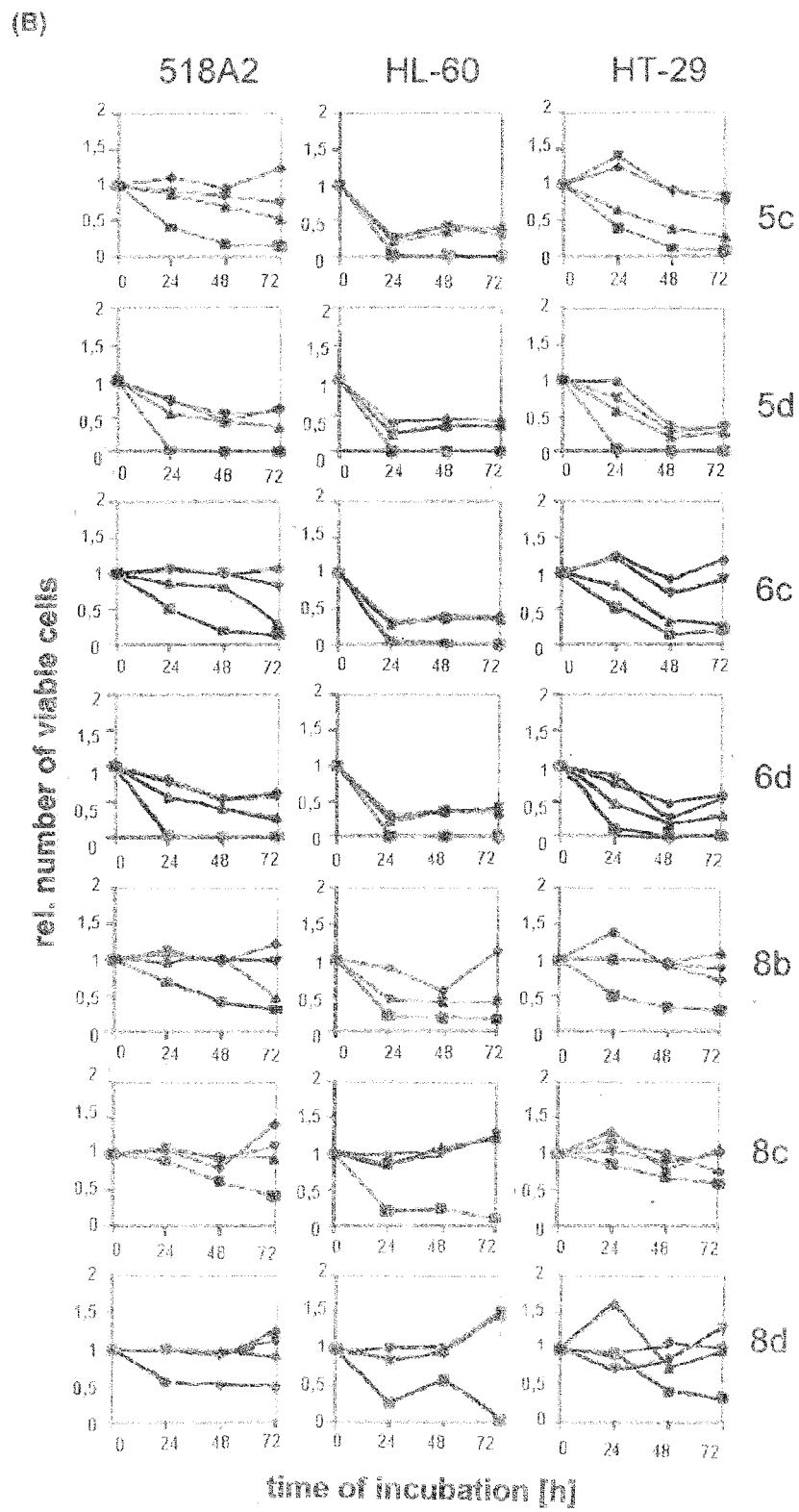

FIG. 6: Cell growth inhibition by reference compound 25f and the compounds 5b, 6b, 8a and 8e or 5c, 5d, 6c, 6d, 8b, 8c and 8d according to the invention (structures are indicated in Example 2 or 4) at various concentrations (■: 100 µM; ▲: 1 µM; ▼: 0.01 µM; ♦: 0.001 µM) in cells of human 518A2 melanoma, HL-60 leukemia, HT-29 colon adenocarcinoma, KB-V1/Vbl cervix carcinoma and MCF-7/Topo breast adenocarcinoma (A) or in cells of human 518A2 melanoma, HL-60 leukemia and HT-29 colon adenocarcinoma (B) upon incubation for 24-72 h (x-axis). Y-axis shows number of viable cells relative to untreated controls (1) as ascertained by the MTT assay.

Figure 7:
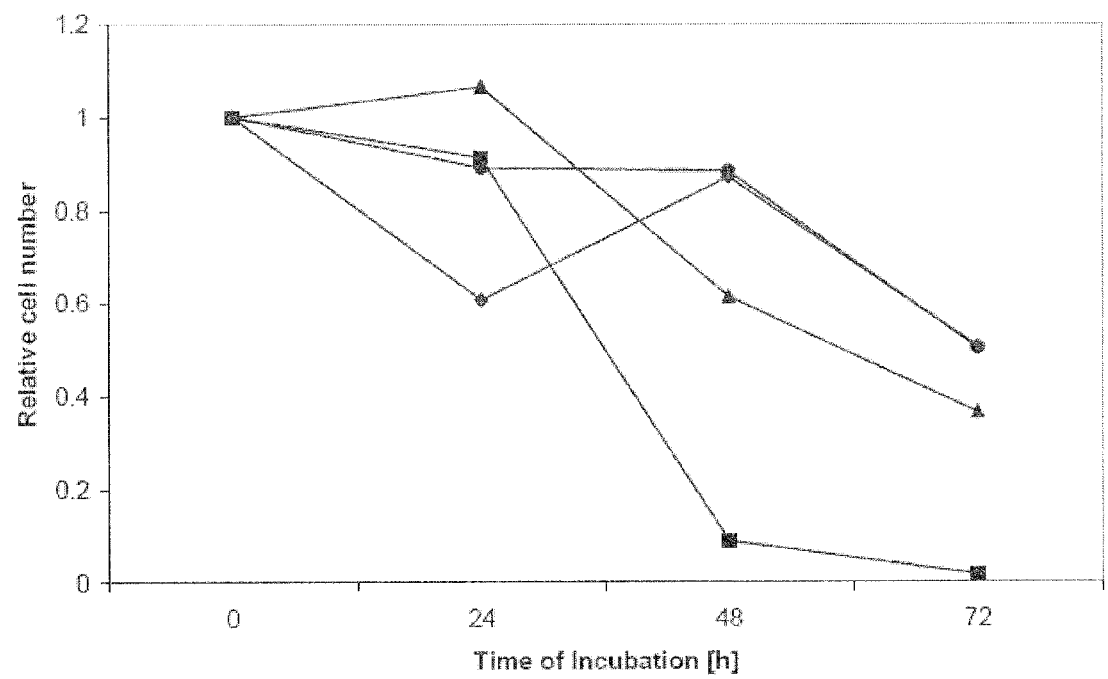

FIG. 7: Cell growth inhibition by combretastatin A-4 at various concentrations (■: 100 µM; ▲: 1 µM; ●: 0.01 µM; ♦: 0.001 µM) in cells of human HT-29 colon adenocarcinoma, incubation for 24-72 h (x-axis). Y-axis shows number of viable cells relative to untreated controls as ascertained by the MTT assay.

Figure 8:
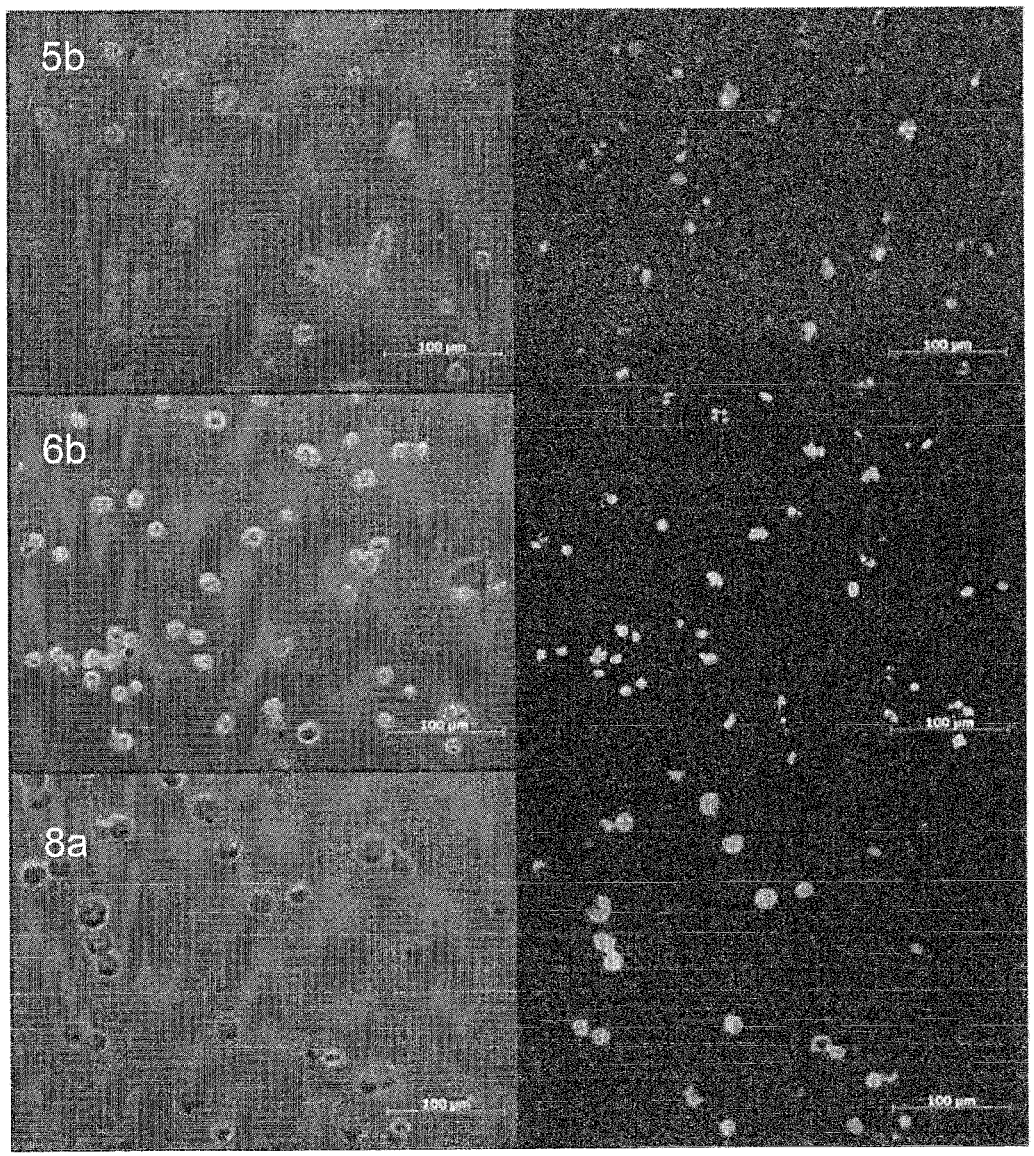

FIG. 8: Microscopic images of HL-60 cells tested in TUNEL assays after 16 h incubation with 10 µM of the compound 5b, 6b or 8a. The brightfield pictures (left) show all the cells in the focus, the pictures of the green fluorescent channel (right) just the apoptotic cells, represented as bright dots.

Figure 9:
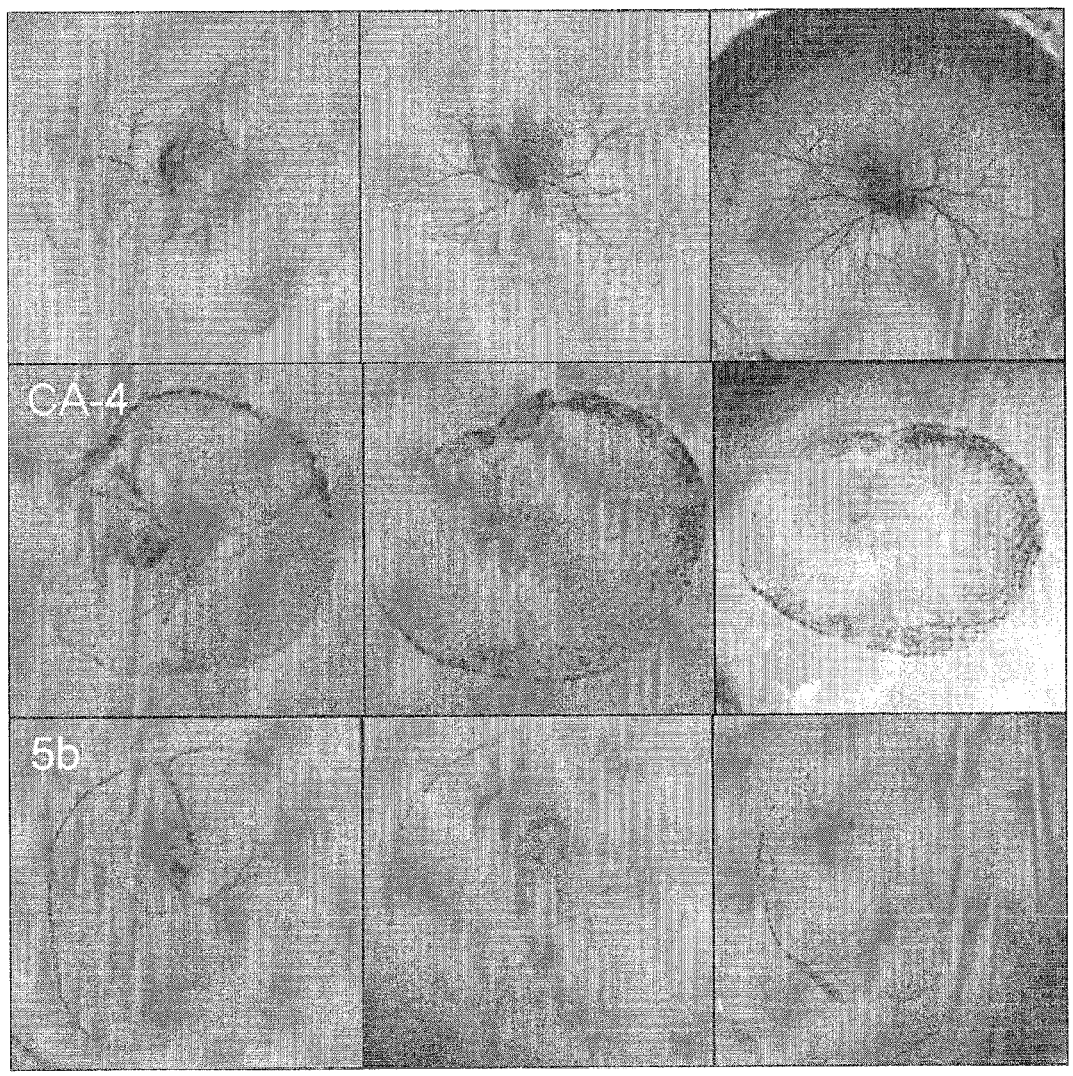

FIG. 9: Chicken embryos with surrounding blood vessels immediately after adding the test compounds CA-4 or 5b (left), after one day (middle) and after three days (right) are shown. The top row shows a negative control. Pictures are representative of at least two independent runs.

Figure 10:
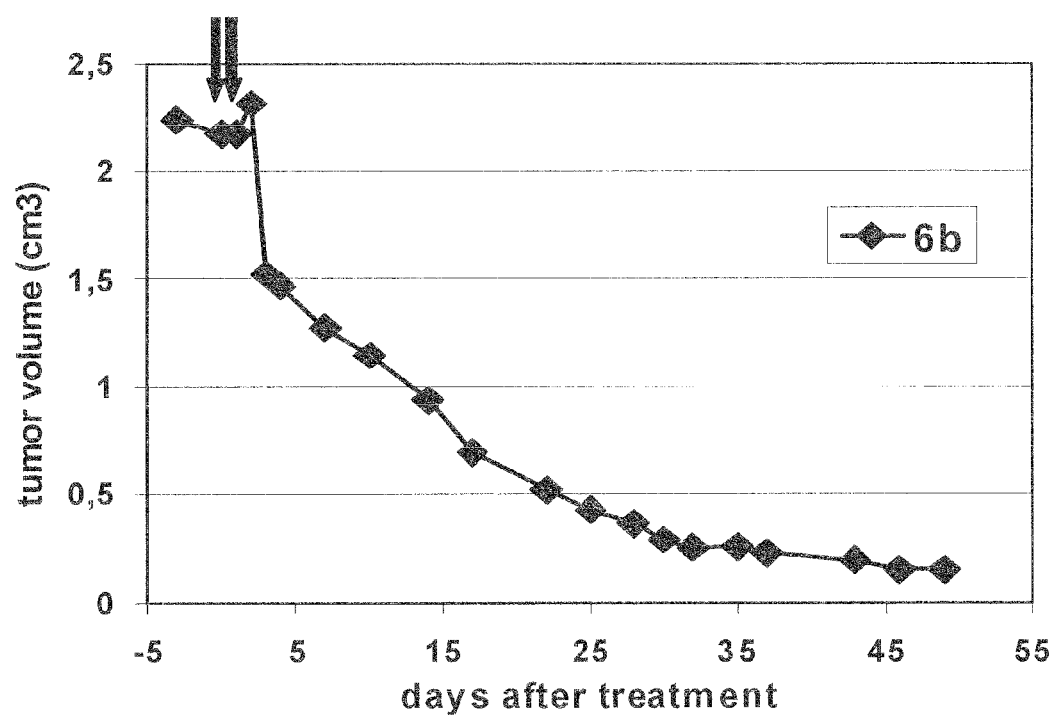

FIG. 10: In vivo anti-tumor activity of compound 6b in mouse xenograft of multi-resistant germ cell tumor cell line 1411HP. The tumor response following dual-dose application is shown. Arrows indicate the administration of test compound.

Figure 11:
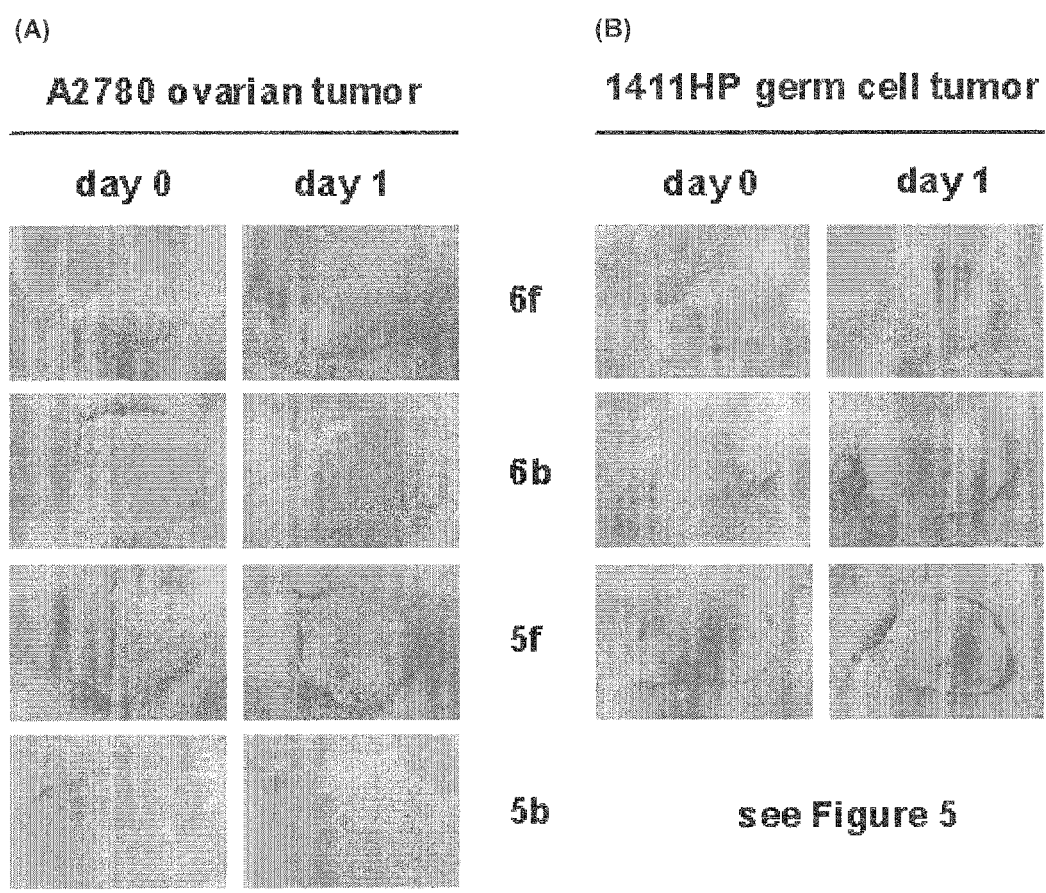

FIG. 11: Vascular disrupting effect of compounds 5b, 6b, 5f and 6f in A2780 ovarian carcinoma xenograft tumors (A) and 1411HP germ cell tumor xenografts (B). The distinct vascular disrupting effect selectively affecting the tumoral vasculature is apparent from hemorrhages leading to red-blue to brown coloring of the entire tumor (day 0: before treatment; day 1: 24 hours after start of treatment) (Test: subcutaneous tumor xenografts in a nude mouse model; mice were anesthesized for the imaging).

Figure 12:
Figure 12:
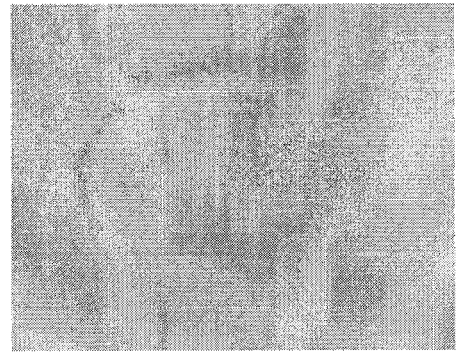

FIG. 12: Vascular disrupting effect in 1411HP germ cell tumor xenograft after oral administration of 6b. The distinct vascular disrupting effect selectively affecting the tumoral vasculature is apparent from hemorrhages leading to red-blue to brown coloring of the entire tumor (day 0: before treatment; day 1: 24 hours after start of treatment) (Test: subcutaneous tumor xenografts in a nude mouse model; mice were anesthesized for the imaging).

Figure 13:
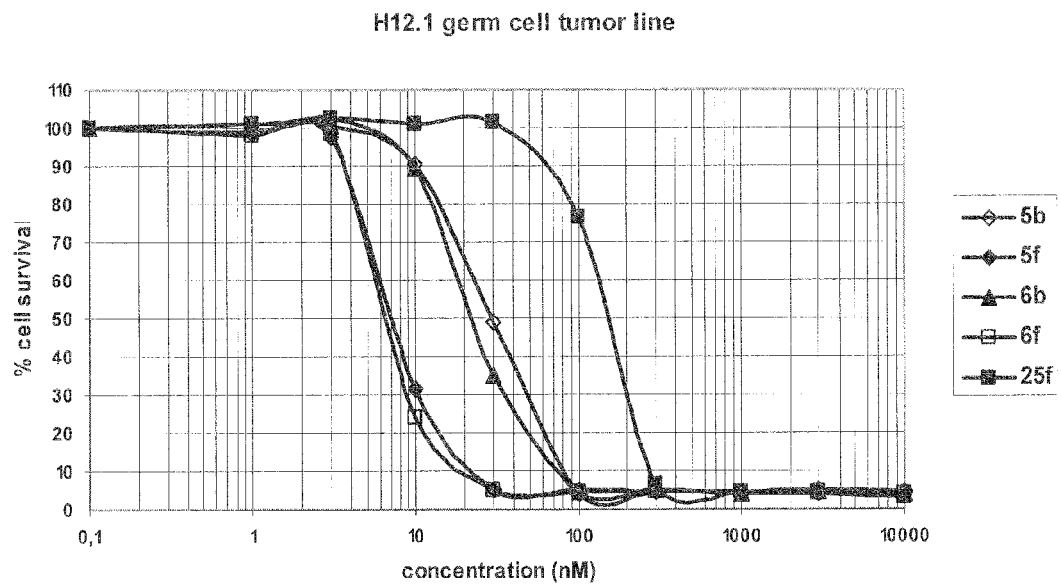
Figure 13:
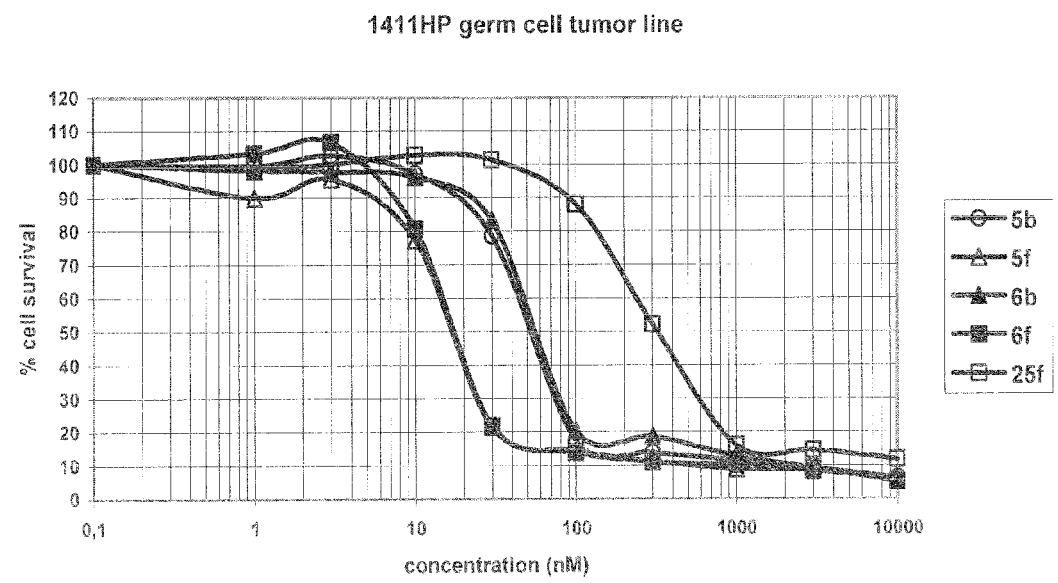
Figure 13:
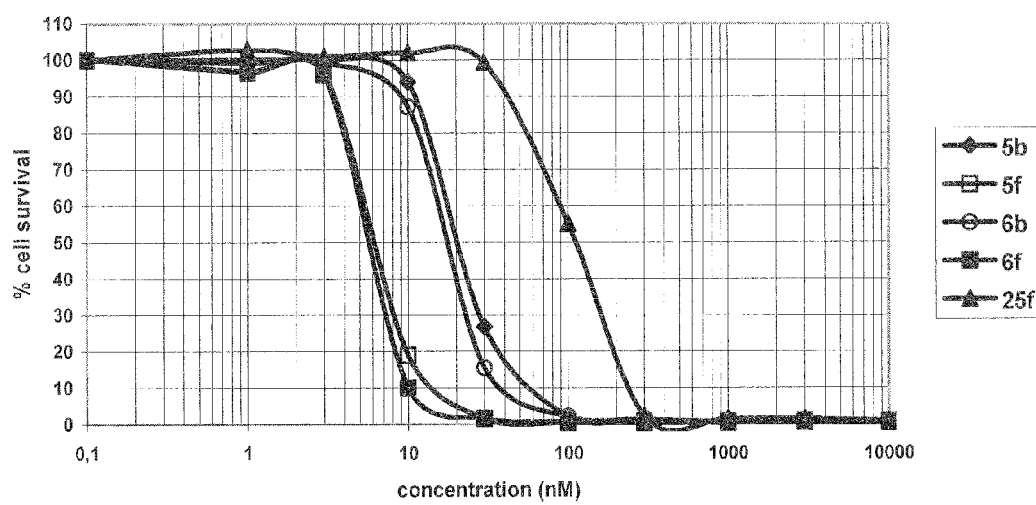
Figure 13:
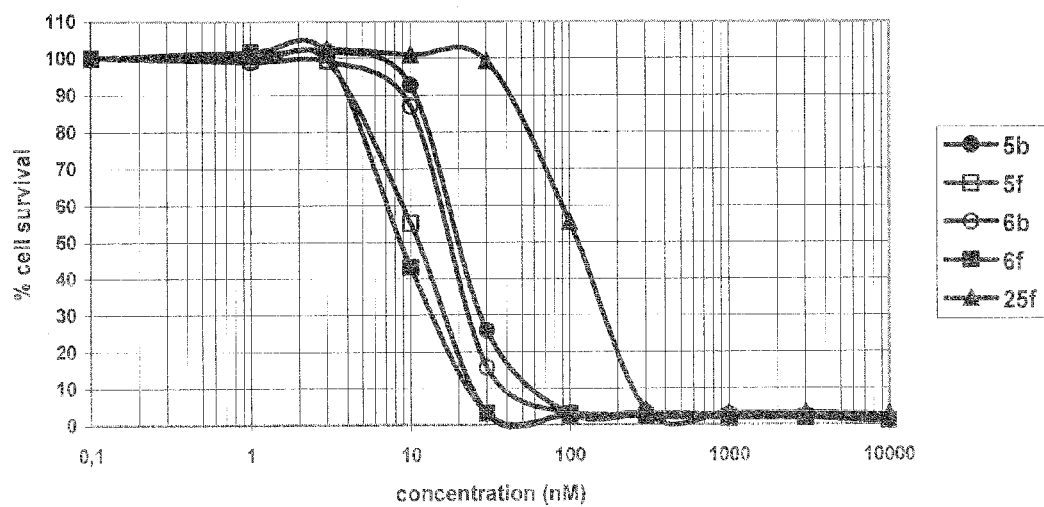
Figure 13:
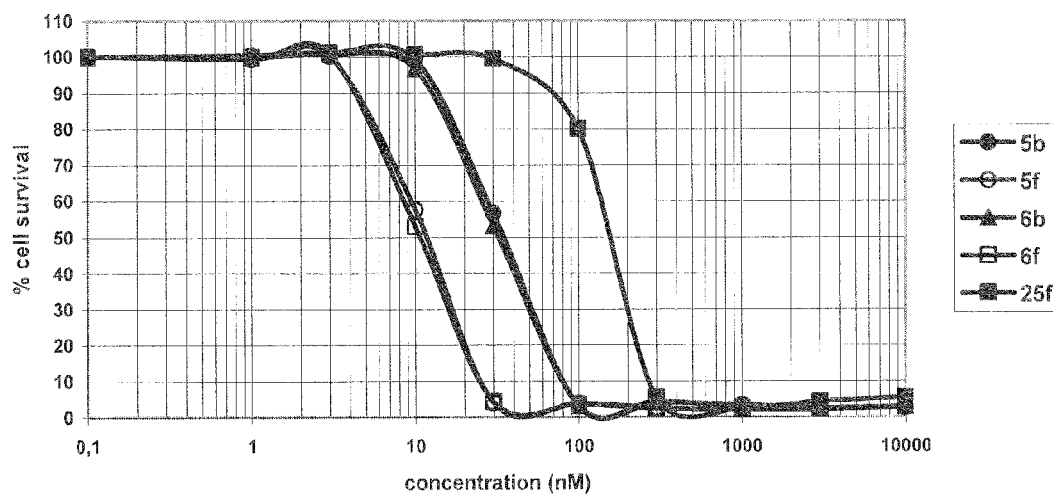
Figure 13:
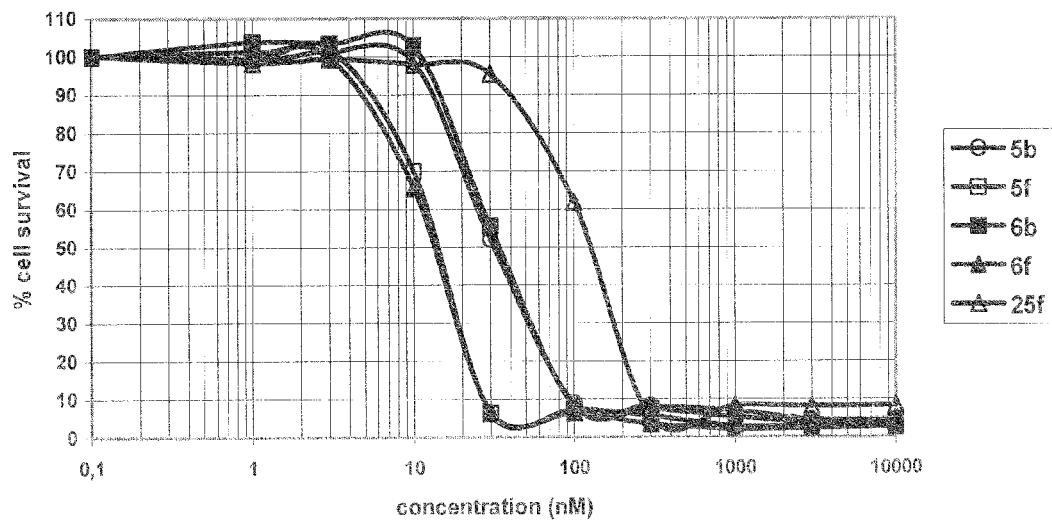

FIG. 13: Comparison of the in vitro cytotoxicities of compounds 5b, 6b, 5f and 6f compared to 25f in H12.1 germ cell tumor (A), 1411HP germ cell tumor (B), A2780 ovarian carcinoma (C), HT29 colon carcinoma (D), DLD1 colon carcinoma (E) and HCT8 colon carcinoma (F) cell lines (Test: SRB-cytotoxicity assay).

Figure 14:
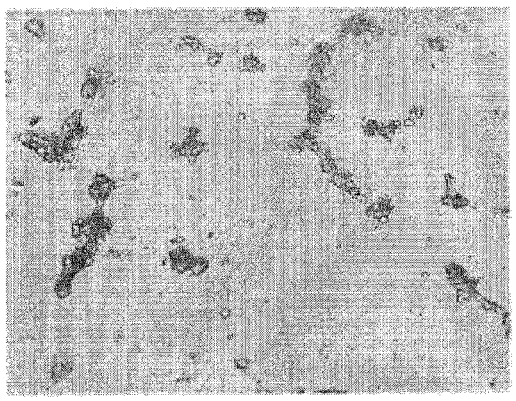
Figure 14:
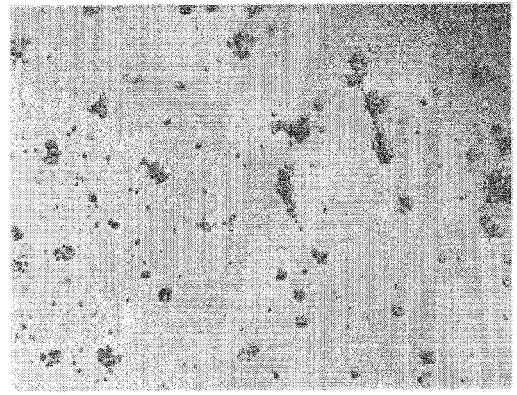
Figure 14:
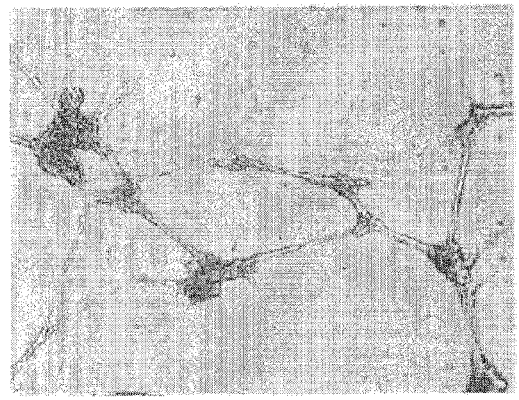
Figure 14:
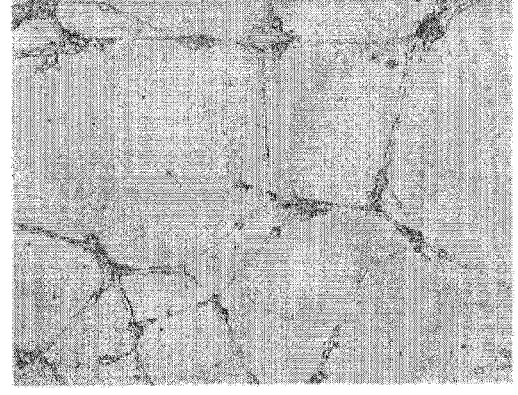

FIG. 14: Tube formation assay with HUVEC cells after treatment with compound 8a (A), 6b (B) or 5b (C) at concentrations of 7.72 ng/mL or control (methanol) (D).

Figure 15:
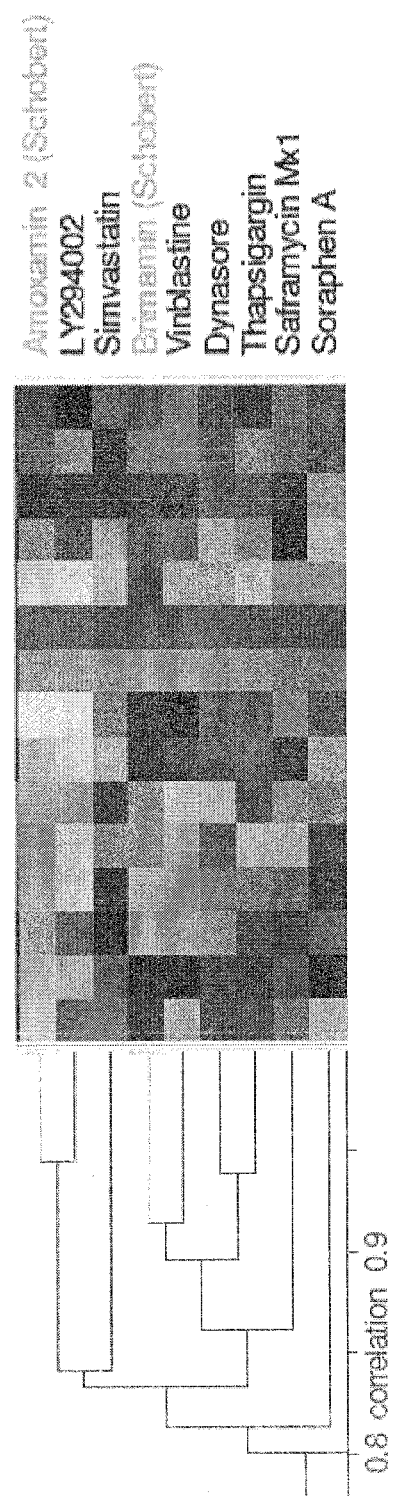

FIG. 15: High-content analysis of compound 6b (denoted as "Brimamin (Schobert)") and compound 8a (denoted as "Amoxamin_2 (Schobert)") in PtK-2 cells.

The invention will now be described by reference to the following examples which are merely illustrative and are not to be construed as a limitation of the scope of the present invention.

EXAMPLES

General Remarks

Melting points were recorded on a GALLENKAMP apparatus and are uncorrected. IR spectra were recorded on a PERKIN-ELMER Spectrum One FT-IR spectrophotometer with ATR sampling unit. Nuclear magnetic resonance (NMR) spectra were recorded under conditions as indicated on a BRUKER Avance 300 spectrometer. Chemical shifts are given in parts per million (δ) downfield from tetramethyl

Example 1

Synthesis of 1-methyl-5-(3-amino-4-methoxyphenyl)-4-(3-chloro-4,5-dimethoxyphenyl)-imidazole bis(hydrochloride) (5b×2 HCl)

1) N-[(Toluene-4-sulfonyl)-(3-chloro-4,5-dimethoxyphenyl)methyl]formamide 3a 5-Chloroveratraldehyde (5.7 g, 23.4 mmol), para-toluenesulfinic acid (3.0 g, 19.3 mmol) and camphorsulfonic acid (110 mg, 0.47 mmol) were treated with formamide (10 mL). Upon heating to 65° C. the reaction mixture turned into a solution and after two hours the product began to precipitate. After stirring for 16 h the precipitate was filtered, washed with methanol and dried in vacuum.

Yield: 4.57 g (11.92 mmol, 51%); colorless solid of mp 157-158° C.; $v_{max}$ (ATR)/cm$^{-1}$: 3190, 3107, 2947, 1690, 1593, 1576, 1484, 1470, 1423, 1403, 1308, 1283, 1250, 1215, 1143, 1121, 1078, 1053, 999, 860, 822, 788, 769, 659, 689; $^{1}$H-NMR (300 MHz, DMSO-d$_6$): δ 2.41 (3H, s, CH$_3$), 3.76 (3H, s, OCH$_3$), 3.79 (3H, s, OCH$_3$), 6.45 (1H, d, $^3$J 10.7 Hz, CH), 7.24 (1H, d, $^4$J 1.9 Hz, 2-H), 7.30 (1H, d, $^4$J 1.9 Hz, 6-H), 7.43 (1H, d, $^3$J 8.4 Hz, Tosyl-3-H/5-H), 7.72 (2H, d, $^3$J 8.4 Hz, Tosyl-2-H/6-H), 7.98 (1H, s, HCONH), 9.74 (1H, d, $^3$J 10.7 Hz, NH); $^{13}$C-NMR (75.5 MHz, DMSO-d$_6$): δ 21.1 (CH$_3$), 56.3 (5-OCH$_3$), 60.3 (4-OCH$_3$), 69.5 (CH), 113.5 (C-6), 122.4 (C-2), 126.7 (C-3), 127.1 (C-1), 129.2 (Tosyl-C-3/C-5), 129.6 (Tosyl-C-2/C-6), 133.2 (Tosyl-C-1), 144.9 (C-4), 145.4 (Tosyl-C-4), 153.1 (C-5), 160.2 (CO); m/z (%) 382 (4), 278 (6), 227 (89), 192 (76), 156 (57), 113 (55), 91 (100), 77 (67), 63 (92).

2) 3-Chloro-4,5-dimethoxyphenyl(tosyl)methyl isocyanide 4a

Compound 3a (4.57 g, 11.92 mmol) was suspended in dry dimethoxyethane (100 mL) and cooled to −10° C. POCl$_3$ (3.4 mL, 36.1 mmol) was added and a mixture of triethylamine (8.3 mL, 59.5 mmol) in dimethoxyethane (10 mL) was dropped slowly to the reaction mixture. After stirring for 2 h at −5° C., the reaction mixture was poured into ice water. The aqueous phase was extracted with ethyl acetate, the organic phase was washed with saturated aqueous NaHCO$_3$ and brine, dried over Na$_2$SO$_4$, filtered and concentrated in vacuum. Upon refrigeration (4° C.) over night a yellow solid crystallized, which was collected and dried in vacuum.

Yield: 2.48 g (6.79 mmol, 57%); yellow solid of mp 115° C.; $v_{max}$ (ATR)/cm$^{-1}$: 2920, 2136, 1593, 1577, 1492, 1452, 1423, 1325, 1294, 1276, 1238, 1199, 1137, 1082, 1053, 1002, 862, 826, 759, 705, 683; $^{1}$H-NMR (300 MHz, CDCl$_3$): δ 2.45 (3H, s, CH$_3$), 3.79 (3H, s, 5-OCH$_3$), 3.87 (3H, s, 4-OCH$_3$), 5.49 (1H, s, CH), 6.76 (1H, d, $^4$J 2.1 Hz, 6-H), 6.88 (1H, d, $^4$J 2.1 Hz, 2-H), 7.34 (2H, d, $^3$J 8.5 Hz, Tosyl-3-H/5-H), 7.64 (2H, d, $^3$J 8.5 Hz, Tosyl-2-H/6-H); $^{13}$C-NMR (75.5 MHz, CDCl$_3$): δ 21.7 (CH$_3$), 56.2 (5-OCH$_3$), 60.8 (4-OCH$_3$), 75.6 (CH), 110.8 (C-6), 122.2 (C-2), 122.6 (C-1), 128.6 (C-3), 129.9 (Tosyl-C-3/C-5), 130.0 (Tosyl-C-4), 130.4 (Tosyl-C-2/C-6), 146.9 (Tosyl-C-1), 147.4 (C-4), 153.8 (C-5), 166.6 (CN); m/z (%) 365 (2) [M$^+$], 278 (7), 246 (10), 210 (100), 155 (23), 91 (54), 66 (20).

3) 1-Methyl-4-(3-chloro-4,5-dimethoxyphenyl)-5-(4-methoxy-3-nitrophenyl)imidazole 5a A mixture of 4-methoxy-3-nitrobenzaldehyde (76 mg, 0.42 mmol) and 33% MeNH$_2$/ethanol (260 μL, 2.10 mmol) in ethanol (15 mL) was treated with acetic acid (150 μL) and refluxed for 2 h. After cooling to room temperature, compound 4a (153 mg, 0.42 mmol) dissolved in dimethoxyethane (10 mL) and K$_2$CO$_3$ (500 mg, 3.62 mmol) was added and the reaction mixture was refluxed for another 3 h. The solvent was evaporated, the residue diluted with ethyl acetate, washed with water and brine, dried over Na$_2$SO$_4$, filtered and concentrated in vacuum. The residue was purified by column chromatography (silica gel 60).

Yield: 110 mg (0.26 mmol, 62%); yellow oil; R$_f$=0.24 (ethyl acetate/methanol 95:5); $v_{max}$ (ATR)/cm$^{-1}$: 2939, 1623, 1600, 1566, 1524, 1505, 1483, 1461, 1396, 1342, 1325, 1263, 1230, 1189, 1167, 1112, 1086, 1047, 994, 889, 873, 863, 828, 816, 762, 737, 698, 675; $^{1}$H-NMR (300 MHz, CDCl$_3$): δ 3.44 (3H, s, NCH$_3$), 3.64 (3H, s, 5-OCH$_3$), 3.75 (3H, s, 4-OCH$_3$), 3.95 (3H, s, 4-OCH$_3$), 6.9-7.0 (2H, m, 2-H, 6-H), 7.15 (1H, d, $^3$J 8.7 Hz, 5-H), 7.45 (1H, dd, $^3$J 8.7 Hz, $^4$J 2.2 Hz, 6-H), 7.50 (1H, s, 2-H), 7.78 (1H, d, $^3$J 2.2 Hz, 2-H); $^{13}$C-NMR (75.5 MHz, CDCl$_3$): δ 32.1 (NCH$_3$), 55.7 (5-OCH$_3$), 56.6 (4-OCH$_3$), 60.5 (4-OCH$_3$), 109.2 (C-6), 114.2 (C-5), 119.7 (C-2), 122.2 (C-1), 126.0 (C-3), 127.3 (C-2), 127.9 (C-5), 130.6 (C-1), 136.4 (C-6), 137.5 (C-4), 137.8 (C-2), 139.7 (C-3), 144.0 (C-4), 152.9 (C-4), 153.4 (C-5); m/z (%) 407 (42), 406 (46), 405 (87) [M$^+$], 404 (77), 403 (100) [M$^+$], 391 (23), 390 (71), 389 (62), 388 (87), 341 (58), 313 (58), 206 (33), 164 (26).

4) 1-Methyl-5-(3-amino-4-methoxyphenyl)-4-(3-chloro-4,5-dimethoxyphenyl)-imidazole bis(hydrochloride) 5b×2 HCl Compound 5a (109 mg, 0.27 mmol) was dissolved in tetrahydrofuran (7.5 mL). Zn powder (107 mg, 1.36 mmol) was added followed by a mixture of conc. HCl (230 μL) in tetrahydrofuran (1 mL). After stirring for 15 min at room temperature the reaction mixture was poured into water and treated with aqueous NaHCO$_3$ to adopt pH 8. The water phase was extracted with ethyl acetate and the organic phase was dried over Na$_2$SO$_4$, filtered and the filtrate was concentrated in vacuum. The residue thus obtained was purified by column chromatography (silica gel 60, 5% methanol/ethyl acetate, R$_f$=0.66) giving crude 5b. This crude product was dissolved in dichloromethane (5 mL) and treated with 3M HCl/dioxane (1 mL). After stirring for 15 min the volatiles were removed and the oily residue was recrystallised from an ethanol/n-hexane mixture to leave the bis(hydrochloride) salt of 5b.

Yield: 42 mg (0.095 mmol, 40%); colorless solid of mp 180-183° C.; UV (MeOH) λ$_{max}$ (λ) 255 (14940); $v_{max}$ (ATR)/cm$^{-1}$: 3009, 2781, 2578, 1635, 1552, 1517, 1497, 1445, 1409, 1304, 1271, 1147, 1113, 1047, 1025, 998, 830, 762, 739, 721; $^{1}$H-NMR (300 MHz, DMSO-d$_6$): δ 3.63 (3H, s, NMe), 3.69 (3H, s, 5-OMe), 3.75 (3H, s, 4-OMe), 3.92 (3H, s, 4-OMe), 7.08 (1H, d, $^4$J 2.1 Hz, 6-H), 7.16 (1H, d, $^4$J 2.1 Hz, 2-H), 9.36 (1H, s, 2-H); $^{13}$C-NMR (75.5 MHz, DMSO-d$_6$): δ 33.9 (NMe), 56.1 (5-OMe), 56.2 (4-OMe), 60.4 (4-OMe), 110.7 (C-6), 112.4 (C-5), 117.6 (C-1), 119.6 (C-2), 123.6 (C-3), 127.3 (C-3), 127.6 (C-5), 129.7 (C-1), 135.7 (C-2), 145.0

(C-4), 153.5 (C-5); m/z (%) 375 (20) [M⁺], 374 (15), 373 (54) [M⁺], 358 (25), 296 (15), 252 (25), 237 (16), 70 (14), 61 (23), 43 (100).

Example 2

Synthesis of Further Compounds According to the Invention

1) N-[(toluene-4-sulfonyl)-(3-bromo-4,5-dimethoxyphenyl)methyl]formamide 3b

Analogously to the synthesis of 3a, compound 3b (4.78 g, 10.81 mmol, 56%) was obtained from 5-bromoveratraldehyde (5.67 g, 23.14 mmol), para-toluenesulfinic acid (3 g, 19.29 mmol), camphorsulfonic acid (110 mg, 0.47 mmol) and formamide (10 mL); colorless solid of mp 162-163° C.; $v_{max}$ (ATR)/cm⁻¹ 3197, 3104, 2945, 1688, 1595, 1569, 1490, 1470, 1422, 1403, 1308, 1301, 1290, 1279, 1250, 1229, 1207, 1144, 1121, 1078, 1049, 998, 832, 769, 705, 688; ¹H NMR (300 MHz, CDCl₃) δ 2.41 (3H, s), 3.82 (6H, s), 6.17 (1H, s), 6.99 (1H, d, J=2.1 Hz), 7.17 (1H, d, J=2.1 Hz), 7.31 (1H, d, J=8.5 Hz), 7.67 (2H, d, J=8.5 Hz), 7.97 (1H, s); ¹³C NMR (75.5 MHz, CDCl₃) δ 21.9, 56.4, 61.0, 70.7, 113.3, 118.0, 125.9, 127.3, 129.9, 130.2, 133.1, 146.2, 147.9, 154.0, 161.3; m/z (EI) 274 (28), 273 (45), 272 (37), 271 (40), 242 (27), 192 (100), 156 (30), 92 (56), 91 (55), 65 (36).

2) N-[(Toluene-4-sulfonyl)-(3,4-dimethoxy-5 nitrophenyl)methyl]formamide 3c

Analogously to the synthesis of 3a, compound 3c (2.63 g, 6.68 mmol, 35%) was obtained from 5-nitroveratraldehyde (4.85 g, 22.99 mmol), para-toluenesulfinic acid (2.96 g, 19.03 mmol), camphorsulfonic acid (110 mg, 0.47 mmol) and formamide (10 mL); colorless solid of mp 133° C.; $v_{max}$ (ATR)/cm⁻¹ 3194, 2888, 1662, 1539, 1518, 1389, 1354, 1319, 1302, 1291, 1212, 1271, 1084, 1074, 1053, 991, 922, 858, 819; ¹H NMR (300 MHz, CDCl₃) δ 2.41 (3H, s), 3.87 (3H, s), 3.95 (3H, s), 6.33 (1H, d, J=10.6 Hz), 7.26 (1H, d, J=2.1 Hz), 7.31 (1H, d, J=8.5 Hz), 7.43 (1H, d, J=2.1 Hz), 7.70 (2H, d, J=8.5 Hz), 8.06 (1H, s), 8.9-9.0 (1H, m); ¹³C NMR (75.5 MHz, CDCl₃) δ 21.7, 56.5, 62.0, 69.9, 116.4, 117.2, 125.8, 129.4, 130.1, 132.3, 143.9, 144.5, 146.1, 154.1, 160.3; m/z (EI) 196 (7), 155 (9), 91 (100), 65 (58).

3) 3-Bromo-4,5-dimethoxyphenyl(tosyl)methyl isocyanide 4b

Compound 3b (4.75 g, 10.75 mmol) was suspended in dry DME (100 mL) and cooled to −10° C. POCl₃ (3.1 mL, 33.1 mol) was added and a mixture of Et₃N (7.5 mL, 53.8 mmol) in DME (10 mL) was dropped slowly to the reaction mixture. After stirring for 2 h at −5° C., the reaction mixture was poured into ice water. The water phase was extracted with ethyl acetate, the organic phase was washed with saturated aqueous NaHCO₃ and brine, dried over Na₂SO₄, filtered and concentrated in vacuum. By refrigeration over night a brown solid crystallized from the residue, which was collected and dried in vacuum. Yield: 2.75 g (6.71 mmol, 62%); brown solid of mp 109-110° C.; $v_{max}$ (ATR)/cm⁻¹ 2915, 2135, 1593, 1569, 1489, 1452, 1420, 1325, 1295, 1275, 1238, 1199, 1136, 1081, 1048, 1003, 862, 826, 759, 705, 670; ¹H NMR (300 MHz, CDCl₃) δ 2.47 (3H, s), 3.81 (3H, s), 3.86 (3H, s), 5.46 (1H, s), 6.81 (1H, d, J=2.2 Hz), 7.01 (1H, d, J=2.2 Hz), 7.35 (2H, d, J=8.3 Hz), 7.64 (2H, d, J=8.3 Hz); ¹³C NMR (75.5 MHz, CDCl₃) δ 321.8, 56.2, 60.7, 75.5, 111.5, 117.8, 123.2, 125.0, 129.9, 130.0, 130.5, 146.9, 148.5, 153.6, 166.6; m/z (EI) 256 (52), 254 (45), 244 (78), 242 (100), 200 (30), 123 (48), 91 (31).

4) 3,4,-Dimethoxy-5-nitrophenyl(tosyl)methyl isocyanide 4c

Compound 3c (2.63 g, 6.68 mmol) was suspended in dry DME (100 mL) and cooled to −10° C. POCl₃ (3.78 mL, 40.4 mol) was added and a mixture of Et₃N (7.5 mL, 66.6 mmol) in DME (10 mL) was dropped slowly to the reaction mixture. After stirring for 2 h at −5° C., the reaction mixture was poured into ice water. The water phase was extracted with ethyl acetate, the organic phase was washed with saturated aqueous NaHCO₃ and brine, dried over Na₂SO₄, filtered and concentrated in vacuum. By refrigeration over night a yellow solid crystallized from the residue, which was collected and dried in vacuum. Yield: 520 mg (1.51 mmol, 23%); yellow solid of mp 134° C. (dec.); $v_{max}$ (ATR)/cm⁻¹ 2949, 2140, 1593, 1538, 1494, 1453, 1360, 1337, 1315, 1285, 1248, 1184, 1156, 1145, 1082, 1065, 988, 921, 819, 784, 701, 667; ¹H NMR (300 MHz, CDCl₃) δ 2.48 (3H, s), 3.91 (3H, s), 4.00 (3H, s), 5.53 (1H, s), 7.12 (1H, d, J=2.2 Hz), 7.18 (1H, d, J=2.2 Hz), 7.38 (2H, d, J=8.4 Hz), 7.67 (2H, d, J=8.4 Hz); ¹³C NMR (75.5 MHz, CDCl₃) 821.9, 56.7, 62.3, 75.3, 115.3, 116.3, 122.3, 129.7, 129.8, 130.4, 144.6, 144.8, 147.4, 154.4, 167.5; m/z (EI) 375 (6) [M⁺-1], 344 (12), 278 (23), 262 (22), 221 (100), 211 (47), 155 (32), 139 (38).

5) 1-Methyl-4-(3'-chloro-4',5'-dimethoxyphenyl)-5-(3''-fluoro-4-methoxyphenyl)-imidazole 5c Analogously to the synthesis of compound 5a, compound 5c was prepared from 3-fluoro-4-methoxybenzaldehyde (65 mg, 0.42 mmol), 33% MeNH₂/ethanol (260 µL, 2.10 mmol) and acetic acid (150 µL) in boiling ethanol (15 mL) giving the imine intermediate, which was treated with compound 4a (153 mg, 0.42 mmol), dissolved in DME (10 mL), and K₂CO₃ (500 mg, 3.62 mmol). After workup, the residue was purified by column chromatography (silica gel 60). Yield: 150 mg (0.38 mmol, 91%); colorless gum; $R_f$=0.27 (ethyl acetate/methanol 95:5); $v_{max}$ (ATR)/cm⁻¹ 2937, 2837, 1601, 1553, 1512, 1487, 1462, 1419, 1301, 1067, 1233, 1166, 1131, 1046, 1022, 999, 896, 873, 829, 815, 761, 734, 719, 656; ¹H NMR (300 MHz, CDCl₃) δ 3.39 (3H, s), 3.61 (3H, s), 3.75 (3H, s), 3.87 (3H, s), 6.9-7.0 (5H, m), 7.45 (1H, s); ¹³C NMR (75.5 MHz, CDCl₃) δ 31.9, 55.6, 56.1, 60.5, 109.0, 113.7, 118.0, 118.2, 119.4, 122.4, 122.5, 126.9, 127.5, 127.8, 131.0, 136.7, 137.2, 143.6, 148.0, 148.1, 150.5, 153.2, 153.8; m/z (EI) 379 (15), 378 (65) [M⁺], 377 (41), 376 (100) [M⁺], 363 (26), 361 (67).

6) 1-Methyl-4-(3'-chloro-4',5'-dimethoxyphenyl)-5-(3''-fluoro-4''-methoxyphenyl)-imidazole hydrochloride 5c×HCl Compound 5c (150 mg, 0.38 mmol) was dissolved in DCM (5 mL) and treated with 3M HCl/dioxane (1 mL). After stirring for 15 min the solvent was removed and the oily residue was recrystallised from an DCM/n-hexane mixture giving the hydrochloride salt of 5c. Yield: 106 mg (0.25 mmol, 66%); colorless solid of mp 185-187° C.; UV (MeOH) $\lambda_{max}$ (ε) 264 (10380); $v_{max}$ (ATR)/cm⁻¹ 3387, 2941, 2840, 2605, 1623, 1553, 1523, 1498, 1464, 1456, 1422, 1303, 1272, 1232, 1134, 1117, 1048, 1019, 997, 872, 844, 817, 760; ¹H NMR (300 MHz, DMSO-d₆) δ 3.63 (3H, s), 3.70 (3H, s), 3.75 (3H, s), 3.92 (3H, s), 7.02 (1H, d, J=2.1 Hz), 7.17 (1H, d, J=2.1 Hz), 7.2-7.3 (1H, m), 7.39 (1H, t, J=17.2 Hz), 7.51 (1H, dd, J=12.0 Hz, J=2.0 Hz), 9.29 (1H, s); $^{13}$C NMR (75.5 MHz, DMSO-d$_6$): δ 33.8, 56.0, 56.2, 60.3, 110.8, 114.6, 117.9, 118.0, 118.3, 118.5, 119.6, 124.0, 127.2, 128.1, 128.5, 128.8, 135.8, 144.9, 148.7, 148.9, 149.8, 153.0, 153.5.

7) 1-Methyl-4-(3'-chloro-4',5'-dimethoxyphenyl)-5-(4"-N,N-dimethylaminophenyl)-imidazole 5d Analogously to the synthesis of compound 5a, compound 5d was prepared from 4-N,N-dimethylaminobenzaldehyde (63 mg, 0.42 mmol), 33% MeNH$_2$/ethanol (260 μL, 2.10 mmol) and acetic acid (150 μL) in boiling ethanol (15 mL) giving the imine intermediate, which was treated with compound 4a (153 mg, 0.42 mmol), dissolved in DME (10 mL), and K$_2$CO$_3$ (500 mg, 3.62 mmol). After workup, the residue was purified by column chromatography (silica gel 60). Yield: 140 mg (0.38 mmol, 91%); colorless oil; R$_f$=0.67 (ethyl acetate/methanol 95:5); ν$_{max}$ (ATR)/cm$^{-1}$ 2935, 2825, 1612, 1552, 1516, 1485, 1397, 1357, 1316, 1261, 1228, 1187, 1165, 1108, 1047, 1000, 944, 881, 857, 818, 762, 721, 660; $^1$H NMR (300 MHz, CDCl$_3$) δ 2.96 (6H, s), 3.39 (3H, s), 3.59 (3H, s), 3.76 (3H, s), 6.72 (2H, d, J=8.9 Hz), 7.00 (1H, d, J=1.9 Hz), 7.11 (2H, d, J=8.9 Hz), 7.16 (1H, d, J=1.9 Hz), 7.46 (1H, s); $^{13}$C NMR (75.5 MHz, CDCl$_3$) δ 31.8, 40.2, 55.5, 60.5, 108.8, 112.3, 116.8, 119.2, 127.7, 129.7, 131.3, 131.6, 135.9, 136.7, 143.2, 150.5, 153.0; m/z (EI) 373 (36) [M$^+$], 371 (100) [M$^+$], 356 (42), 281 (10), 72 (19), 59 (34).

8) 1-Methyl-4-(3'-chloro-4',5'-dimethoxyphenyl)-5-(4"-N,N-dimethylaminophenyl)-imidazole bis(hydrochloride) 5d×2 HCl Compound 5d (140 mg, 0.38 mmol) was dissolved in DCM (5 mL) and treated with 3M HCl/dioxane (1 mL). After stirring for 10 min the solvent was evaporated and the residue crystallized from ethanol/n-hexane. Yield: 77 mg (0.17 mmol, 46%); colorless solid of mp 189-193° C. (dec.); UV (MeOH) λ$_{max}$ (ε) 265 (20800); ν$_{max}$ (ATR)/cm$^{-1}$ 3356, 3022, 2956, 2835, 2452, 1620, 1595, 1551, 1499, 1470, 1422, 1319, 1279, 1231, 1190, 1160, 1129, 1052, 1020, 989, 897, 859, 842, 756, 696; $^1$H NMR (300 MHz, DMSO-d$_6$) δ 3.00 (6H, s), 3.62 (3H, s), 3.69 (3H, s), 3.74 (3H, s), 6.98 (2H, d, J=8.8 Hz), 7.07 (1H, d, J=2.1 Hz), 7.21 (1H, d, J=2.1 Hz), 7.33 (2H, d, J=8.8 Hz), 9.37 (1H, s); $^{13}$C NMR (75.5 MHz, DMSO-d$_6$) δ 33.9, 40.2, 56.1, 60.4, 107.8, 113.2, 119.5, 123.8, 127.0, 127.2, 130.8, 131.6, 135.4, 144.9, 150.8, 153.5.

9) 1-Methyl-4-(3'-chloro-4',5'-dimethoxyphenyl)-5-(4"-ethoxy-3"-nitrophenyl)-imidazole 5e A mixture of 4-ethoxy-3-nitrobenzaldehyde (82 mg, 0.42 mmol) and 33% MeNH$_2$/ethanol (260 μL, 2.10 mmol) in ethanol (15 mL) was treated with AcOH (150 μL, 2.63 mmol) and refluxed for 2 h. After cooling down to room temperature, 4a (153 mg, 0.42 mmol) and K$_2$CO$_3$ (500 mg, 3.62 mmol) were added and the reaction mixture was refluxed for 5 h. The solvent was evaporated, the residue diluted with ethyl acetate, washed with water and brine, dried over Na$_2$SO$_4$, filtered and concentrated in vacuum. The residue was purified by column chromatography (silica gel 60, ethyl acetate/methanol 9:1) giving the product as an orange oil. Yield: 170 mg (0.34 mmol, 81%); ν$_{max}$ (ATR)/cm$^{-1}$: 2938, 1622, 1600, 1553, 1527, 1506, 1484, 1353, 1286, 1263, 1110, 1045, 998, 870, 829, 817, 762, 739, 656, 635; $^1$H NMR (300 MHz, CDCl$_3$): δ 1.43 (3H, t, $^3$J 7.0 Hz, Me), 3.44 (3H, s, NMe), 3.63 (3H, s, 4'-OMe), 3.75 (3H, s, 5'-OMe), 4.18 (2H, q, $^3$J 7.0 Hz, OCH$_2$), 6.9-7.0 (2H, m, 2'-H, 6'-H), 7.12 (1H, d, $^3$J 8.7 Hz, 5"-H), 7.41 (1H, dd, $^3$J 8.7 Hz, $^4$J 2.2 Hz, 6"-H), 7.49 (1H, s, 2-H), 7.75 (1H, d, $^4$J 2.2 Hz, 2"-H); $^{13}$C NMR (75.5 MHz, CDCl$_3$): δ 14.3 (Me), 32.1 (NMe), 55.7 (5'-OMe), 60.5 (4'-OMe), 65.5 (OCH$_2$), 109.1 (C-6'), 115.0 (C-5"), 119.6 (C-2'), 121.9 (C-1"), 126.1 (C-5), 127.2 (C-6"), 127.9 (C-3'), 130.6 (C-1'), 136.2 (C-2"), 137.4 (C-4), 137.8 (C-2), 139.9 (C-3"), 143.9 (C-4'), 152.2 (C-5'), 153.3 (C-4"); m/z (%) 419 (36) [M$^+$], 417 (100) [M$^+$], 402 (53).

10) 1-Methyl-5-(3"-amino-4"ethoxyphenyl)-4-(3'-chloro-4-4',5'-dimethoxyphenyl)-imidazole 5f×2 HCl Compound 5e (140 mg, 0.34 mmol) was dissolved in THF (7.5 mL). Zn powder (110 mg, 1.68 mmol) was added followed by a mixture of conc. HCl (243 μL) in THF (1 mL). After stirring for 15 min at room temperature the reaction mixture was poured onto water and basified with aqueous NaHCO$_3$ to ca. pH 8. The water phase was extracted with ethyl acetate and the organic phase was dried over Na$_2$SO$_4$, filtered and the filtrate was concentrated in vacuum. The residue was purified by column chromatography (silica gel 60, 10% methanol/ethyl acetate, R$_f$=0.63) giving the aniline intermediate. This compound was dissolved in DCM (5 mL) and treated with 3M HCl/dioxane (1 mL). After stirring for 15 min the solvent was removed and the residue was recrystallized from a DCM/n-hexane mixture. Yield: 97 mg (0.21 mmol, 62%); colorless solid of m.p.>150° C. (dec.); ν$_{max}$ (ATR)/cm$^{-1}$: 3392, 2976, 2833, 2538, 1631, 1550, 1514, 1495, 1466, 1396, 1302, 1268, 1237, 1142, 1115, 1044, 996, 850, 816, 762, 722; $^1$H NMR (300 MHz, DMSO-d$_6$): δ 1.40 (3H, t, $^3$J 6.9 Hz, Me), 3.63 (3H, s, NMe), 3.70 (3H, s, 4'-OMe), 3.75 (3H, s, 5'-OMe), 4.21 (2H, q, $^3$J 6.9 Hz, OCH$_2$), 7.07 (1H, d, $^4$J 2.1 Hz, 6'-H), 7.19 (1H, d, $^4$J 2.1 Hz, 2'-H), 7.3-7.4 (2H, m, 5"-H, 6"H), 7.45 (1H, s, 2"-H), 9.41 (1H, s, 2-H); $^{13}$C NMR (75.5 MHz, DMSO-d$_6$): δ 14.4 (Me), 34.0 (NMe), 56.2 (5'-OMe), 60.4 (4'-OMe), 64.6 (OCH$_2$), 110.8 (C-6'), 113.7 (C-5"), 117.5 (C-1"), 119.6 (C-2'), 123.5 (C-5), 127.3 (C-3'), 127.7 (C-1'), 129.3 (C-4), 135.8 (C-2), 145.0 (C-4'), 151.7 (C-5'), 153.5 (C-4"); m/z (%) 388 (35) [M$^+$], 386 (100) [M$^+$], 371 (36), 36 (98).

11) 1-Methyl-4-(3'-chloro-4',5'-dimethoxyphenyl)-5-(3"-fluoro-4"-ethoxyphenyl)-imidazole 5g×HCl A mixture of 3-fluoro-4-ethoxybenzaldehyde (124 mg, 0.74 mmol) and 33% MeNH$_2$/ethanol (460 μL, 3.76 mmol) in ethanol (15 mL) was treated with AcOH (260 μL, 4.63 mmol) and refluxed for 2 h. After cooling down to room temperature, 4a (270 mg, 0.74 mmol) and K$_2$CO$_3$ (500 mg, 3.62 mmol) were added and the reaction mixture was refluxed for 5 h. The solvent was evaporated, the residue diluted with ethyl acetate, washed with water, dried over Na$_2$SO$_4$, filtered and concentrated in vacuum. The residue was purified by column chromatography (silica gel 60, ethyl acetate/methanol 95:5) giving the imidazole as a colorless oil. This oil was dissolved in DCM (5 mL) and treated with 3 M HCl in dioxane (1 mL). After stirring for 5 min the solvent was evaporated and the residue crystallised from DCM/n-hexane. Yield: 210 mg (0.49 mmol, 66%), colorless solid; ν$_{max}$ (ATR)/cm$^{-1}$: 3391, 3166, 2946, 2841, 2727, 1627, 1554, 1523, 1499, 1477, 1423, 1395, 1302, 1269, 1230, 1193, 1136, 1117, 1050, 998, 888, 844, 814, 778, 753; $^1$H NMR (300 MHz, acetone-d$_6$): δ 1.44 (3H, t, $^3$J 7.0 Hz), 3.75 (3H, s), 3.77 (3H, s), 3.88 (3H, s), 4.25 (2H, q, 3J 7.0 Hz), 7.01 (1H, d, $^4$J 2.1 Hz), 7.35 (1H, t, $^3$J$_{HF}$ 18.0 Hz), 7.56 (1H, dd, $^3$J 11.7 Hz, 4J 1.9 Hz), 9.71 (1H, s); $^{13}$C NMR (75.5 MHz, acetone-d): δ 15.0, 34.9, 57.1, 60.8, 65.7, 111.8, 113.8, 116.3, 119.2, 119.3, 119.6, 119.9, 120.6, 122.4, 124.4, 124.5, 128.6, 129.2, 130.1, 134.6, 136.6, 146.4, 149.8, 149.9, 151.7, 154.8, 155.0; m/z (%) 392 (37) [M$^+$], 390 (100) [M$^+$], 377 (21), 375 (65).

12) 1-Methyl-4-(3'-chloro-4',5'-dimethoxyphenyl)-5-(N-methyl-3"-chloroindol-5"-yl)-imidazole 5i Analogously to the synthesis of 5a, compound 5i was obtained from the imine of N-methyl-3-chloroindol-5-carboxaldehyde (81 mg, 0.42 mmol), 33% MeNH$_2$/ethanol (260 µL, 2.10 mmol) and acetic acid (150 µL) in boiling ethanol (15 mL), which was treated with 4a (153 mg, 0.42 mmol) and K$_2$CO$_3$ (500 mg, 3.62 mmol). Yield: 160 mg (0.39 mmol, 93%); colorless oil; R$_f$=0.62 (ethyl actetate/methanol 95:5); ν$_{max}$ (ATR)/cm$^{-1}$: 2937, 2830, 1600, 1565, 1504, 1476, 1463, 1397, 1314, 1261, 1240, 1166, 1109, 1047, 999, 972, 907, 883, 856, 831, 803, 727, 700, 686, 656; $^1$H-NMR (300 MHz, CDCl$_3$): δ 3.41 (3H, s, 1-NMe), 3.52 (3H, s, 5'-OMe), 3.75 (6H, s, 1"-NMe, 4'-OMe), 7.02 (1H, d, $^4$J 2.0 Hz, 6'-H), 7.06 (1H, s, 2"-H), 7.09 (1H, d, $^4$J 2.0 Hz, 2'-H), 7.14 (1H, dd, $^3$J 8.5 Hz, $^4$J 1.5 Hz, 6"-H), 7.35 (1H, d, $^3$J 8.5 Hz, 7"-H), 7.52 (1H, s, 2-H), 7.57 (1H, d, $^4$J 1.5 Hz, 4"-H); $^{13}$C-NMR (75.5 MHz, CDCl$_3$): δ 32.0 (1-NMe), 33.0 (1"-NMe), 55.6 (5"-OMe), 60.5 (4'-OMe), 104.6 (C-3"), 109.0 (C-6'), 110.3 (C-7"), 119.4 (C-2'), 120.5 (C-4"), 121.5 (C-5"), 125.1 (C-6"), 126.0, 126.3 (C-2"), 127.7 (C-3'), 129.8 (C-5), 131.5 (C-1'), 135.7 (C-7a"), 136.3 (C-4), 136.9 (C-2), 143.5 (C-4'), 153.1 (C-5'); m/z (EI) 417 (72) [M], 415 (100) [M], 402 (43), 400 (55).

13) 1-Methyl-4-(3'-chloro-4',5'-dimethoxyphenyl)-5-(N-methyl-3"-chloroindol-5"-yl)-imidazole-hydrochloride 5i×HCl Compound 5i (160 mg, 0.39 mmol) was dissolved in DCM (5 mL) and treated with 3M HCl/dioxane (1 mL). After stirring at room temperature for 10 min the solvent was evaporated in vacuum and the residue was recrystallised from DCM/n-hexane. Yield: 98 mg (0.20 mmol, 51%); colorless solid; mp. 198° C.; UV (MeOH) λ$_{max}$ (ε) 230 (30800); ν$_{max}$ (ATR)/cm$^{-1}$: 3392, 2941, 2845, 2602, 1622, 1565, 1542, 1493, 1464, 1456, 1318, 1239, 1115, 1046, 996, 971, 871, 852, 803; $^1$H-NMR (300 MHz, DMSO-d$_6$): δ 3.61 (6H, s, 1-NMe, 5'-OMe), 3.72 (3H, s, 4'-OMe), 3.86 (3H, s, 1"-NMe), 6.99 (1H, d, $^4$J 2.1 Hz, 6'-H), 7.20 (1H, d, $^4$J 2.1 Hz, 2'-H), 7.34 (1H, dd, $^3$J 9.4 Hz, $^4$J 1.6 Hz, 6"-H), 7.7-7.8 (3H, m, 2"-H, 4"-H, 7"-H), 9.32 (1H, s, 2-H); $^{13}$C-NMR (75.5 MHz, DMSO-d$_6$): δ 33.0 (1-NMe), 33.9 (1"-NMe), 56.0 (5"-OMe), 60.3 (4'-OMe), 102.7 (C-3"), 110.8 (C-6'), 111.8 (C-7"), 117.0 (C-5"), 119.5 (C-2'), 120.4 (C-4"), 124.1 (C-3a"), 124.5 (C-6"), 125.1 (C-7a"), 127.2 (C-3'), 127.9 (C-5), 128.3 (C-2"), 130.9 (C-1'), 135.6 (C-2), 136.0 (C-4), 144.8 (C-4'), 153.4 (C-5'); m/z (EI) 417 (100) [M$^+$-2 HCl], 415 (68) [M$^+$-2 HCl], 402 (66), 400 (96).

14) 1-Methyl-4-(3'-bromo-4',5'-dimethoxyphenyl)-5-(4"-methoxy-3"-nitrophenyl)-imidazole 6a A mixture of 4-methoxy-3-nitrobenzaldehyde (76 mg, 0.42 mmol) and 33% MeNH$_2$/ethanol (260 µL, 2.10 mmol) in ethanol (15 mL) was treated with AcOH (150 µL) and refluxed for 2 h. After cooling down to room temperature, compound 4b (172 mg, 0.42 mmol) dissolved in DME (10 mL) and K$_2$CO$_3$ (500 mg, 3.62 mmol) was added and the reaction mixture was refluxed for 3 h. The solvent was evaporated, the residue diluted with ethyl acetate, washed with water and brine, dried over Na$_2$SO$_4$, filtered and concentrated in vacuum. The residue was purified by column chromatography (silica gel 60; elution with ethyl acetate to 5% methanol/ethyl acetate). Yield: 100 mg (0.22 mmol, 52%); yellow oil; R$_f$=0.36 (ethyl acetate); ν$_{max}$ (ATR)/cm$^{-1}$ 2937, 2832, 1622, 1599, 1548, 1526, 1506, 1480, 1462, 1351, 1263, 1231, 1185, 1165, 1110, 1092, 1042, 998, 909, 889, 868, 824, 808, 760, 728; $^1$H NMR (300 MHz, CDCl$_3$) δ 3.46 (3H, s), 3.64 (3H, s)), 3.75 (3H, s), 3.97 (3H, s), 6.97 (1H, s), 7.12 (1H, s), 7.16 (1H, d, J=8.7 Hz), 7.46 (1H, d, J=8.7 Hz), 7.51 (1H, s), 7.80 (1H, s); $^{13}$C NMR (75.5 MHz, CDCl$_3$) δ 32.2, 55.7, 56.7, 60.4, 110.0, 114.2, 117.4, 122.2, 122.5, 126.1, 127.4, 131.2, 136.5, 137.5, 137.9, 139.7, 145.0, 152.9, 153.3; m/z (EI) 448 (100) [M$^+$], 446 (97) [M$^+$], 433 (37), 431 (41), 206 (27), 164 (23).

15) 1-Methyl-5-(3"-amino-4"-methoxyphenyl)-4-(3'-bromo-4',5'-dimethoxyphenyl)-imidazole 6b Analogously to 5b, compound 6a (100 mg, 0.22 mmol) was reduced by Zn powder (72 mg, 1.11 mmol) and conc. HCl (160 µL) in THF (8.5 mL). After workup the residue was purified by column chromatography (silica gel 60; ethyl acetate/methanol 95:5). Yield: 83 mg (0.20 mmol, 91%); colorless solid of mp 166-169° C.; R$_f$=0.48 (ethyl acetate); UV (MeOH) λ$_{max}$ (ε) 274 (12760); ν$_{max}$ (ATR)/cm$^{-1}$ 3458, 3365, 3192, 2935, 2833, 1616, 1597, 1546, 1510, 1483, 1462, 1420, 1372, 1318, 1279, 1245, 1223, 1174, 1109, 1040, 1024, 997, 868, 804, 759, 658; $^1$H NMR (300 MHz, DMSO-d$_6$) δ 3.41 (3H, s), 3.57 (3H, s), 3.67 (3H, s), 3.82 (3H, s), 4.91 (2H, s), 6.55 (1H, d, J=8.2 Hz), 6.61 (1H, s), 6.94 (1H, d, J=8.2 Hz), 7.09 (1H, s), 7.26 (1H, s), 7.71 (1H, s); $^{13}$C NMR (75.5 MHz, DMSO-d$_6$) δ 31.6, 55.4, 60.0, 109.4, 110.9, 115.3, 116.4, 118.2, 120.8, 122.2, 129.8, 132.7, 134.2, 138.3, 143.5, 146.7, 152.8; m/z (EI) 418 (100) [M$^+$], 416 (96) [M$^+$], 403 (78), 401 (85), 307 (17), 169 (22).

16) 1-Methyl-5-(3"-amino-4"-methoxyphenyl)-4-(3'-bromo-4',5'-dimethoxyphenyl)-imidazole bis(hydrochloride) 6b×2 HCl Compound 6b (61 mg, 0.15 mmol) was dissolved in DCM and treated with 3M HCl/dioxane (1 mL). After stirring for 15 min at room temperature the solvent was removed and the residue recrystallized from an ethanol/n-hexane mixture. Yield: 72 mg (0.15 mmol, 100%); colorless solid of mp 198-200° C.; ν$_{max}$ (ATR)/cm$^{-1}$ 3011, 2801, 2567, 1633, 1549, 1515, 1494, 1446, 1405, 1305, 1272, 1145, 1113, 1041, 1022, 994, 867, 852, 829, 718; $^1$H NMR (300 MHz, DMSO-d$_6$): δ 3.63 (3H, s), 3.69 (3H, s), 3.73 (3H, s), 3.93 (3H, s), 7.18 (1H, d, J=2.0 Hz), 7.22 (1H, d, J=2.0 Hz), 7.3-7.4 (3H, m), 9.37 (1H, s); $^{13}$C NMR (75.5 MHz, DMSO-d$_6$) δ 33.9, 56.1, 60.2, 111.3, 112.5, 117.0, 117.6, 122.4, 124.2, 127.5, 129.6, 135.8, 146.0, 151.6, 153.3.

17) 1-Methyl-4-(3'-bromo-4',5'-dimethoxyphenyl)-5-(3"-fluoro-4"-methoxyphenyl)-imidazole 6c Analogously to the synthesis of 5a, compound 6c was prepared from 3-fluoro-4-methoxybenzaldehyde (65 mg, 0.42 mmol), 33% MeNH$_2$/ethanol (260 µL, 2.10 mmol) and acetic acid (150 µL) in boiling ethanol (15 mL) giving the imine intermediate, which was treated with compound 4b (172 mg, 0.42 mmol), dissolved in DME (10 mL), and K$_2$CO$_3$ (500 mg, 3.62 mmol). After workup, the residue was purified by column chromatography (silica gel 60; elution with ethyl acetate to 5% methanol/ethyl acetate). Yield: 135 mg (0.32 mmol, 76%); colorless gum; R$_f$=0.67 (ethyl acetate); UV (MeOH) λ$_{max}$ (ε) 275 (12280); ν$_{max}$ (ATR)/cm$^{-1}$ 2934, 2832, 1598, 1548, 1511, 1483, 1462, 1418, 1300, 1265, 1233, 1214, 1166, 1131, 1109, 1041, 1022, 997, 895, 865, 816, 807, 760, 656; $^1$H NMR (300 MHz, CDCl$_3$) δ 3.45 (3H, s), 3.58 (3H, m), 3.68 (3H, s), 3.90 (3H, s), 7.01 (1H, s), 7.16 (1H, s), 7.2-7.4 (3H, m), 7.78 (1H, s); $^{13}$C NMR (75.5 MHz, CDCl$_3$) δ 31.8, 55.4, 56.1, 60.1, 109.6, 114.3, 116.5, 117.9, 118.2, 121.1, 122.3, 122.4, 127.5, 127.6, 127.7, 132.3, 135.2, 138.1, 143.8, 147.5, 147.7, 149.8, 153.0, 153.1; m/z (EI) 421 (51) [M$^+$], 419 (49) [M$^+$], 406 (23), 404 (22), 233 (11), 175 (31), 117 (75), 59 (100).

18) 1-Methyl-4-(3'-bromo-4',5'-dimethoxyphenyl)-5-(3"-fluoro-4"-methoxyphenyl)-imidazole hydrochloride 6c×HCl Compound 6c (135 mg, 0.32 mmol) was dissolved in DCM (5 mL) and treated with 3M HCl/dioxane (1 mL). After stirring for 15 min the solvent was removed and the oily residue was recrystallised from an DCM/n-hexane mixture giving the hydrochloride salt. Yield: 91 mg (0.20 mmol, 63%); colorless solid of mp 103-106° C. (dec.); UV (MeOH) λ$_{max}$ (ε) 270 (11680); ν$_{max}$ (ATR)/cm$^{-1}$ 3413, 3012, 2936, 2841, 2626, 1625, 1547, 1523, 1493, 1463, 1421, 1304, 1271, 1234, 1203, 1134, 1116, 1041, 994, 869, 849, 818, 760; $^1$H NMR (300 MHz, DMSO-d$_6$) 53.64 (3H, s), 3.68 (3H, s), 3.73 (3H, s), 3.92 (3H, s), 7.16 (1H, d, J=2.0 Hz), 7.19 (1H, d, J=2.0 Hz), 7.3-7.4 (1H, m), 7.39 (1H, t, J=17.2 Hz), 7.51 (1H, dd, J=12.0 Hz, J=2.0 Hz), 9.28 (1H, s); $^{13}$C NMR (75.5 MHz, CDCl$_3$) δ 34.3, 56.5, 56.7, 60.7, 111.9, 115.1, 117.4, 118.3, 118.4, 118.8, 119.0, 123.0, 125.1, 128.6, 128.8, 129.3, 136.3, 146.4, 149.2, 149.3, 150.2, 153.5, 153.8.

19) 1-Methyl-4-(3'-bromo-4',5'-dimethoxyphenyl)-5-(4"-N,N-dimethylaminophenyl)-imidazole 6d Analogously to the synthesis of 5a, compound 6d was prepared from 4-N,N-dimethylaminobenzaldehyde (63 mg, 0.42 mmol), 33% MeNH$_2$/ethanol (260 μL, 2.10 mmol) and acetic acid (150 μL) in boiling ethanol (15 mL) giving the imine intermediate, which was treated with compound 4b (172 mg, 0.42 mmol), dissolved in DME (10 mL), and K$_2$CO$_3$ (500 mg, 3.62 mmol). After workup, the residue was purified by column chromatography (silica gel 60). Yield: 140 mg (0.34 mmol, 81%); colorless gum; R$_f$=0.65 (ethyl acetate/methanol 95:5); ν$_{max}$ (ATR)/cm$^{-1}$ 2933, 2828, 1612, 1546, 1515, 1481, 1462, 1357, 1314, 1258, 1228, 1187, 1164, 1108, 1039, 999, 944, 873, 859, 821, 806, 758, 738, 717, 659; $^1$H NMR (300 MHz, CDCl$_3$) δ 2.94 (6H, s), 3.39 (3H, s), 3.56 (3H, s), 3.74 (3H, s), 6.72 (2H, d, J=8.9 Hz), 7.00 (1H, d, J=1.9 Hz), 7.10 (2H, d, J=8.9 Hz), 7.35 (1H, d, J=1.9 Hz), 7.46 (1H, s); $^{13}$C NMR (75.5 MHz, CDCl$_3$) δ 31.8, 40.2, 55.5, 60.3, 109.5, 112.3, 116.8, 117.2, 122.1, 129.7, 131.3, 132.3, 135.8, 136.7, 144.2, 150.5, 152.9; m/z (EI) 417 (54), 415 (68), 402 (28), 400 (26), 278 (54), 250 (58), 234 (63), 206 (83), 145 (84), 125 (87), 42 (100).

20) 1-Methyl-4-(3'-bromo-4',5'-dimethoxyphenyl)-5-(4"-N,N-dimethylaminophenyl)-imidazole bis(hydrochloride) 6d×2 HCl Compound 6d (140 mg, 0.34 mmol) was dissolved in DCM and treated with 3M HCl/dioxane (1 mL). After stirring for 15 min at room temperature the solvent was removed and the residue recrystallized from an ethanol/n-hexane mixture. Yield: 68 mg (0.14 mmol, 41%); colorless solid of mp 189-193° C. (dec.); UV (MeOH) λ$_{max}$ (ε) 265 (21220); ν$_{max}$ (ATR)/cm$^{-1}$ 3357, 2541, 2451, 1593, 1546, 1497, 1470, 1421, 1316, 1277, 1230, 1190, 1159, 1129, 1046, 987, 843; $^1$H NMR (300 MHz, DMSO-d$_6$) δ 2.99 (6H, s), 3.63 (3H, s), 3.68 (3H, s), 3.73 (3H, s), 6.94 (2H, d, J=8.9 Hz), 7.21 (2H, s), 7.32 (2H, d, J=8.9 Hz), 9.35 (1H, s); $^{13}$C NMR (75.5 MHz, DMSO-d$_6$) δ 33.9, 56.1, 60.2, 111.3, 112.9, 116.9, 122.3, 124.4, 126.9, 130.8, 131.5, 135.3, 145.9, 150.9, 153.3.

21) 1-Methyl-4-(3'-bromo-4',5'-dimethoxyphenyl)-5-(4"-ethoxy-3"-nitrophenyl)-imidazole 6e A mixture of 4-ethoxy-3-nitrobenzaldehyde (82 mg, 0.42 mmol) and 33% MeNH$_2$/ethanol (260 μL, 2.10 mmol) in ethanol (15 mL) was treated with AcOH (150 μL, 2.63 mmol) and refluxed for 2 h. After cooling down to room temperature, 4b (172 mg, 0.42 mmol) and K$_2$CO$_3$ (500 mg, 3.62 mmol) were added and the reaction mixture was refluxed for 5 h. The solvent was evaporated, the residue diluted with ethyl acetate, washed with water and brine, dried over Na$_2$SO$_4$, filtered and concentrated in vacuum. The residue was purified by column chromatography (silica gel 60, ethyl acetate/methanol 9:1) giving the product as an orange oil. Yield: 170 mg (0.37 mmol, 88%); ν$_{max}$ (ATR)/cm$^{-1}$: 2983, 2936, 1622, 1599, 1547, 1527, 1505, 1472, 1353, 1247, 1110, 1039, 997, 865, 808, 759, 739, 655, 634; $^1$H NMR (300 MHz, CDCl$_3$): δ 1.41 (3H, t, $^3$J 7.0 Hz, Me), 3.42 (3H, s, NMe), 3.60 (3H, s, 4'-OMe), 3.72 (3H, s, 5'-OMe), 4.16 (2H, q, $^3$J 7.0 Hz, OCH$_2$), 6.92 (1H, d, $^4$J 2.0 Hz, 6'-H), 7.0-7.1 (2H, m, 2'-H, 5"-H), 7.40 (1H, dd, $^3$J 8.7 Hz, $^4$J 2.3 Hz, 6"-H), 7.47 (1H, s, 2-H), 7.73 (1H, d, $^4$J 2.3 Hz, 2"-H); $^{13}$C NMR (75.5 MHz, CDCl$_3$): δ 14.2 (Me), 32.1 (NMe), 55.6 (5'-OMe), 60.3 (4'-OMe), 65.5 (OCH$_2$), 109.8 (C-6'), 115.0 (C-5"), 117.2 (C-3'), 121.8 (C-1"), 122.3 (C-2'), 126.1 (C-5), 127.1 (C-6"), 131.2 (C-1'), 136.2 (C-2"), 137.2 (C-4), 137.7 (C-2), 139.9 (C-3"), 144.8 (C-4'), 152.1 (C-5'), 153.1 (C-4"); m/z (%) 463 (99) [M$^+$], 461 (100) [M$^+$], 447 (46), 445 (45).

22) 1-Methyl-5-(3"-amino-4"-ethoxyphenyl)-4-(3'-bromo-4',5'-dimethoxyphenyl)-imidazole 6f×2 HCl Compound 6e (170 mg, 0.37 mmol) was dissolved in THF (7.5 mL). Zn powder (120 mg, 1.83 mmol) was added followed by a mixture of conc. HCl (264 μL) in THF (1 mL). After stirring for 15 min at room temperature the reaction mixture was poured onto water and basified with aqueous NaHCO$_3$ to ca. pH 8. The water phase was extracted with ethyl acetate and the organic phase was dried over Na$_2$SO$_4$, filtered and the filtrate was concentrated in vacuum. The residue was purified by column chromatography (silica gel 60, 10% methanol/ethyl acetate, R$_f$=0.64) giving the aniline intermediate. This compound was dissolved in DCM (5 mL) and treated with 3M HCl/dioxane (1 mL). After stirring for 15 min the solvent was removed and the residue was recrystallized from a DCM/n-hexane mixture. Yield: 121 mg (0.22 mmol, 65%); colorless solid of m.p.>160° C. (dec.); ν$_{max}$ (ATR)/cm$^{-1}$: 3369, 2936, 2829, 2540, 1632, 1547, 1492, 1411, 1395, 1303, 1270, 1235, 1141, 1114, 1038, 993, 862, 818, 720; $^1$H NMR (300 MHz, DMSO-d$_6$): δ 1.40 (3H, t, $^3$J 6.9 Hz, Me), 3.63 (3H, s, NMe), 3.70 (3H, s, 4'-OMe), 3.72 (3H, s, 5'-OMe), 4.19 (2H, q, $^3$J 6.9 Hz, OCH$_2$), 7.1-7.3 (4H, m, 2'-H, 6'-H, 5"-H, 6"H), 7.45 (1H, s, 2"-H), 9.41 (1H, s, 2-H); $^{13}$C NMR (75.5 MHz, DMSO-d$_6$): δ 14.4 (Me), 34.0 (NMe), 56.2 (5'-OMe), 60.2 (4'-OMe), 64.6 (OCH$_2$), 111.4 (C-6'), 113.7 (C-5"), 117.0 (C-3'), 117.5 (C-1"), 122.4 (C-2'), 124.2 (C-5), 127.6 (C-1'), 129.3 (C-4), 135.8 (C-2), 146.0

(C-4'), 151.7 (C-5'), 153.3 (C-4"); m/z (%) 433 (100) [M], 431 (100) [M+], 416 (31), 404 (16), 402 (15), 36 (69).

23) 1-Methyl-4-(3'-bromo-4',5'-dimethoxyphenyl)-5-(3"-fluoro-4"-ethoxyphenyl)-imidazole 6g×HCl A mixture of 3-fluoro-4-ethoxybenzaldehyde (71 mg, 0.42 mmol) and 33% MeNH$_2$/ethanol (260 µL, 2.10 mmol) in ethanol (15 mL) was treated with AcOH (150 µL, 2.63 mmol) and refluxed for 2 h. After cooling down to room temperature, 4b (172 mg, 0.42 mmol) and K$_2$CO$_3$ (500 mg, 3.62 mmol) were added and the reaction mixture was refluxed for 5 h. The solvent was evaporated, the residue diluted with ethyl acetate, washed with water and brine, dried over Na$_2$SO$_4$, filtered and concentrated in vacuum. The residue was purified by column chromatography (silica gel 60, ethyl acetate/methanol 9:1). The resulting colorless oil was dissolved in DCM (5 mL) and treated with 3M HCl/dioxane. The reaction mixture was stirred at room temperature for 10 min, and the solvent was evaporated. The residue was recrystallised from DCM/n-hexane. Yield: 160 mg (0.34 mmol, 81%); colorless solid of mp 90° C.; $\nu_{max}$(ATR)/cm$^-$: 3391, 3111, 2976, 2939, 2884, 2833, 2620, 1626, 1547, 1523, 1494, 1474, 1421, 1397, 1304, 1270, 1233, 1115, 1039, 995, 927, 885, 851, 809, 778, 756; $^1$H NMR (300 MHz, DMSO-d$_6$): δ 1.37 (3H, t, $^3$J 6.9 Hz), 3.71 (3H, s), 3.73 (3H, s), 4.19 (2H, q, $^3$J 6.9 Hz), 7.14 (1H, d, $^4$J 2.0 Hz), 7.26 (1H, d, $^4$J 2.0 Hz), 7.2-7.3 (2H, m), 7.37 (1H, t, $^3$J 17.1 Hz), 7.51 (1H, dd, $^3$J 11.9 Hz, $^4$J 1.9 Hz), 9.37 (1H, s); $^{13}$C NMR (75.5 MHz, DMSO-d$_6$): δ 14.4, 33.9, 56.1, 60.2, 64.6, 111.5, 115.5, 116.9, 118.6, 122.5, 124.3, 128.2, 128.9, 135.7, 146.1, 148.2, 153.3; m/z (%) 436 (100) [M+], 434 (100) [M+], 421 (96), 419 (95), 340 (12), 36 (15).

24) 1-Methyl-4-(3'-bromo-4',5'-dimethoxyphenyl)-5-(N-methyl-3"-chloroindol-5"-yl)-imidazole 6i Analogously to the synthesis of 5a, compound 6i was obtained from the imine of N-methyl-3-chloroindol-5-carboxaldehyde (81 mg, 0.42 mmol), 33% MeNH$_2$/ethanol (260 µL, 2.10 mmol) and acetic acid (150 µL) in boiling ethanol (15 mL), which was treated with 4b (170 mg, 0.42 mmol) and K$_2$CO$_3$ (500 mg, 3.62 mmol). After workup the residue was purified by column chromatography (silica gel 60). Yield: 130 mg (0.28 mmol, 67%); colorless oil; R$_f$=0.63 (ethyl acetate/methanol 95:5); $\nu_{max}$ (ATR)/cm$^{-1}$: 3113, 2835, 2825, 1597, 1561, 1504, 1474, 1461, 1418, 1396, 1373, 1312, 1256, 1240, 1164, 1109, 1042, 997, 971, 907, 875, 854, 808, 728; $^1$H-NMR (300 MHz, CDCl$_3$): δ 3.41 (3H, s, 1-NMe), 3.48 (3H, s, 5'-OMe), 3.73 (3H, s, 4'-OMe), 3.75 (3H, s, 1"-NMe), 7.01 (1H, d, $^4$J 1.9 Hz, 6'-H), 7.05 (1H, s, 2"-H), 7.14 (1H, dd, $^3$J 8.6 Hz, $^4$J 1.6 Hz, 6"-H), 7.30 (1H, d, $^4$J 1.9 Hz, 2'-H), 7.35 (1H, d, $^4$J 8.6 Hz, 7"-H), 7.52 (1H, s, 2-H), 7.56 (1H, d, $^4$J 1.6 Hz, 4"-H); $^{13}$C-NMR (75.5 MHz, CDCl$_3$): δ 32.0 (1-NMe), 33.0 (1"-NMe), 55.5 (5'-OMe), 60.4 (4'-OMe), 104.6 (C-3"), 109.7 (C-6'), 110.2 (C-7"), 117.2 (C-3'), 120.5 (C-4"), 121.4 (C-5"), 122.2 (C-2'), 125.1 (C-6"), 126.0 (C-3a"), 126.3 (C-2"), 129.8 (C-5), 132.1 (C-1'), 135.7 (C-7a"), 136.2 (C-4), 136.9 (C-2), 144.4 (C-4'), 152.9 (C-5'); m/z (EI) 461 (100) [M+], 459 (82) [M+], 446 (59), 444 (57).

25) 1-Methyl-4-(3'-bromo-4',5'-dimethoxyphenyl)-5-(N-methyl-3"-chloroindol-5"-yl)-imidazole-hydrochloride 6i×HCl Compound 6i (130 mg, 0.28 mmol) was dissolved in DCM (5 mL) and treated with 3M HCl/dioxane (1 mL). After stirring at room temperature for 15 min the solvent was evaporated in vacuum and the residue was recrystallised from ethanol/n-hexane. Yield: 109 mg (0.20 mmol, 73%); colorless solid; mp. 146° C.; UV (MeOH) $\lambda_{max}$ (ε) 230 (34040); $\nu_{max}$ (ATR)/cm$^{-1}$: 3392, 2941, 2591, 1622, 1592, 1544, 1490, 1464, 1406, 1317, 1263, 1239, 1146, 1115, 1042, 995, 973, 874, 853, 809; $^1$H-NMR (300 MHz, DMSO-d$_6$): δ 3.61 (6H, s, 1-NMe, 5'-OMe), 3.70 (3H, s, 4'-OMe), 3.86 (3H, s, 1"-NMe), 7.14 (1H, d, $^4$J 2.1 Hz, 6'-H), 7.26 (1H, d, $^4$J 2.1 Hz, 2'-H), 7.34 (1H, dd, $^3$J 8.5 Hz, $^4$J 1.6 Hz, 6"-H), 7.7-7.8 (3H, m, 2"-H, 4"-H, 7"-H), 9.36 (1H, s, 2-H); $^{13}$C-NMR (75.5 MHz, DMSO-d$_6$): δ 33.0 (1-NMe), 33.9 (1"-NMe), 56.0 (5'-OMe), 60.2 (4'-OMe), 102.7 (C-3"), 111.4 (C-6'), 111.8 (C-7"), 116.9 (C-5"), 117.0 (C-3'), 120.4 (C-4"), 122.3 (C-2'), 124.5 (C-6"), 124.7 (C-3a"), 125.1 (C-7a"), 127.7 (C-5), 128.3 (C-2"), 130.9 (C-1'), 135.5 (C-2), 136.0 (C-4), 145.9 (C-4'), 153.2 (C-5'); m/z (EI) 461 (100) [M+-2 HCl], 459 (82) [M+-2 HCl], 446 (59), 444 (57).

26) 4-(3',4'-dimethoxy-5'-nitrophenyl)-5-(4"-methoxy-3"-nitrophenyl)-oxazole 7a Compound 4c (170 mg, 0.45 mmol), 4-methoxy-3-nitrobenzaldehyde (82 mg 0.74 mmol) and anhydrous K$_2$CO$_3$ (590 mg, 4.3 mmol) were dissolved in DME/methanol (1:3, 20 mL) and stirred for 2 h. The solution was concentrated in vacuum, taken up in ethyl acetate, washed with water and brine, dried over Na$_2$SO$_4$, filtered and the filtrate was concentrated in vacuum. The residue was purified by column chromatography (silica gel 60). Yield: 140 mg (0.35 mmol, 78%); yellow solid of mp 155° C.; R$_f$=0.30 (ethyl acetate/n-hexane 1:1); $\nu_{max}$ (ATR)/cm$^{-1}$ 3147, 2945, 2846, 1625, 1564, 1522, 1482, 1456, 1441, 1342, 1278, 1267, 1256, 1184, 1162, 1126, 1111, 1058, 1005, 985, 849, 832; $^1$H NMR (300 MHz, CDCl$_3$) δ 3.84 (3H, s), 3.96 (3H, s), 3.97 (3H, s), 7.13 (1H, d, J=8.9 Hz), 7.38 (1H, d, J=2.0 Hz), 7.54 (1H, d, J=2.0 Hz), 7.74 (1H, dd, J=8.9 Hz, J=2.3 Hz), 7.93 (1H, s), 8.07 (1H, d, J=2.3 Hz); $^{13}$C NMR (75.5 MHz, CDCl$_3$) δ 56.4, 56.7, 62.0, 114.1, 114.8, 120.4, 124.0, 127.3, 132.2, 132.9, 139.7, 142.7, 144.0, 144.9, 150.1, 153.2, 154.3; m/z (EI) 401 (34) [M+], 400 (100), 385 (12), 339 (7).

27) 4-(3',4'-dimethoxy-5'-nitrophenyl)-5-(4"-N,N-dimethylaminophenyl)-oxazole 7b Compound 4c (170 mg, 0.45 mmol), 4-N,N-dimethylaminobenzaldehyde (67 mg 0.45 mmol) and anhydrous K$_2$CO$_3$ (590 mg, 4.3 mmol) were dissolved in DME/methanol (1:3, 20 mL) and stirred for 2 h. The solution was concentrated in vacuum, taken up in ethyl acetate, washed with water and brine, dried over Na$_2$SO$_4$, filtered and the filtrate was concentrated in vacuum. The residue was purified by column chromatography (silica gel 60). Yield: 70 mg (0.19 mmol, 42%); yellow oil; R$_f$=0.30 (ethyl acetate/n-hexane 1:2); $\nu_{max}$ (ATR)/cm$^{-1}$ 2941, 2886, 1611, 1532, 1518, 1445, 1352, 1264, 1230, 1190, 1167, 1104, 1053, 992, 944, 920, 870, 854, 818, 784, 771, 733, 697; $^1$H NMR (300 MHz, CDCl$_3$) δ 2.99 (6H, s), 3.84 (3H, s), 3.97 (3H, s), 6.69 (2H, d, J=9.1 Hz), 7.44 (2H, d, J=9.1 Hz), 7.48 (1H, d, J=2.0 Hz), 7.65 (1H, d, J=2.0 Hz), 7.86 (1H, s); $^{13}$C NMR (75.5 MHz, CDCl$_3$) δ 40.1, 56.4, 62.0, 111.9, 114.5, 114.8, 115.0, 128.2, 128.8, 130.1, 141.8, 145.0, 147.8, 149.1, 150.9, 153.9; m/z (EI) 369 (100) [M+], 308 (7), 132 (12).

28) 1-Methyl-5-(3"-benzyloxy-4"-methoxyphenyl)-4-(3',4'-dimethoxy-5'-nitrophenyl)imidazole 7c A mixture of 3-benzoxy-4-methoxybenzaldehyde (102 mg, 0.42 mmol) and 33% MeNH$_2$/ethanol (260 µL, 2.10 mmol) in ethanol (15 mL) was treated with AcOH (150 µL, 2.63 mmol) and refluxed for 2 h. After cooling down to room temperature, compound 4c (158 mg, 0.42 mmol) dissolved in DME (5 mL) and $K_2CO_3$ (500 mg, 3.62 mmol) were added and the reaction mixture was refluxed for 3 h. The solvent was evaporated, the residue diluted with ethyl acetate, washed with water and brine, dried over $Na_2SO_4$, filtered and concentrated in vacuum. The residue was purified by column chromatography (silica gel 60). Yield: 130 mg (0.27 mmol, 64%); red oil; $R_f$=0.58 (ethyl acetate/methanol 95:5); $v_{max}$ (ATR)/cm$^{-1}$ 2939, 2837, 1529, 1509, 1454, 1358, 1248, 1169, 1136, 1110, 1060, 1021, 993, 919, 858, 814, 764, 729, 696; $^1$H NMR (300 MHz, CDCl$_3$) δ 3.25 (3H, s), 3.61 (3H, s), 3.86 (3H, s), 3.89 (3H, s), 5.09 (2H, s), 6.74 (1H, d, J=2.0 Hz), 6.85 (1H, dd, J=8.2 Hz, J=1.9 Hz), 6.95 (1H, d, J=1.9 Hz), 7.1-7.3 (6H, m), 7.36 (1H, d, J=2.0 Hz), 7.45 (1H, s); $^{13}$C NMR (75.5 MHz, CDCl$_3$) δ 31.7, 55.8, 55.9, 61.7, 71.0, 112.1, 113.0, 113.4, 116.3, 121.6, 123.7, 127.0, 127.8, 128.4, 129.4, 130.9, 135.4, 136.4, 137.2, 140.5, 144.6, 148.2, 150.4, 153.3; m/z (EI) 475 (62), 458 (26), 384 (21), 337 (22), 91 (100), 65 (36).

29) 1-Methyl-4-(3',4'-dimethoxy-5'-nitrophenyl)-5-(3"-fluoro-4"-methoxyphenyl)-imidazole 7d A mixture of 3-fluoro-4-methoxybenzaldehyde (77 mg, 0.42 mmol) and 33% MeNH$_2$/ethanol (260 µL, 2.10 mmol) in ethanol (15 mL) was treated with AcOH (150 µL, 2.63 mmol) and refluxed for 2 h. After cooling down to room temperature, compound 4c (158 mg, 0.42 mmol) dissolved in DME (5 mL) and $K_2CO_3$ (500 mg, 3.62 mmol) were added and the reaction mixture was refluxed for 3 h. The solvent was evaporated, the residue diluted with ethyl acetate, washed with water and brine, dried over $Na_2SO_4$, filtered and concentrated in vacuum. The residue was purified by column chromatography (silica gel 60). Yield: 120 mg (0.31 mmol, 74%); red oil; $R_f$=0.45 (ethyl acetate/methanol 95:5); $v_{max}$ (ATR)/cm$^{-1}$ 2941, 2841, 1530, 1511, 1462, 1357, 1300, 1267, 1238, 1131, 1110, 1021, 993, 920, 867, 855, 817, 761, 730, 657; $^1$H NMR (300 MHz, CDCl$_3$) δ 3.43 (3H, s), 3.69 (3H, s), 3.86 (3H, s), 3.89 (3H, s), 7.0-7.1 (3H, m), 7.29 (1H, d, J=2.0 Hz), 7.30 (1H, d, J=2.0 Hz), 7.50 (1H, s); $^{13}$C NMR (75.5 MHz, CDCl$_3$) δ 32.0, 56.0, 56.1, 61.8, 113.2, 113.7, 113.9, 117.9, 118.2, 121.9, 122.0, 126.9, 128.2, 130.7, 135.9, 137.5, 140.7, 144.7, 148.3, 148.5, 150.7, 153.5, 154.0; m/z (EI) 387 (100) [M$^+$], 372 (34), 212 (20).

30) N-Methyl-3-chloroindol-5-carbaldehyde 7e'

N-Methylindol-5-carbaldehyde (400 mg, 2.5 mmol) was dissolved in dry acetonitrile (10 mL) and treated with N-chlorosuccinimide (400 mg, 3.02 mmol), whereupon the solution turned red. The reaction mixture was stirred at room temperature for 20 h. The solvent was removed in vacuum and the residue was purified by column chromatography (silica gel 60). Yield: 300 mg (1.55 mmol, 62%); colorless solid of mp 109° C.; $R_f$=0.27 (ethyl acetate/n-hexane 1:4); $v_{max}$ (ATR)/cm$^{-1}$ 3103, 2845, 2751, 1680, 1602, 1454, 1414, 1362, 1343, 1274, 1238, 1196, 1160, 1134, 1111, 981, 894, 796, 717; $^1$H NMR (300 MHz, CDCl$_3$) δ 3.75 (3H, s), 7.07 (1H, s), 7.32 (1H, d, J=8.6 Hz), 7.76 (1H, dd, J=8.6 Hz, J=1.5 Hz), 8.07 (1H, d, J=1.5 Hz), 10.01 (1H, s); $^{13}$C NMR (75.5 MHz, CDCl$_3$) δ 32.0, 106.3, 109.9, 122.0, 123.3, 125.2, 126.9, 129.2, 138.5, 191.7; m/z (EI) 193 (100) [M$^+$], 164 (57), 128 (43), 101 (48), 87 (28).

31) 1-Methyl-4-(3',4'-dimethoxy-5'-nitrophenyl)-5-(N-methyl-3"-chloroindol-5"-yl)-imidazole 7e A mixture of N-methyl-5-chloroindol-3-carbaldehyde (81 mg, 0.42 mmol) and 33% MeNH$_2$/ethanol (260 µL, 2.10 mmol) in ethanol (15 mL) was treated with AcOH (150 µL, 2.63 mmol) and refluxed for 2 h. After cooling down to room temperature, compound 4c (170 mg, 0.43 mmol) and $K_2CO_3$ (500 mg, 3.62 mmol) were added and the reaction mixture was refluxed for 3 h. The solvent was evaporated, the residue diluted with ethyl acetate, washed with water and brine, dried over $Na_2SO_4$, filtered and concentrated in vacuum. The residue was purified by column chromatography (silica gel 60). Yield: 120 mg (0.28 mmol, 67%); red oil; $R_f$=0.52 (ethyl acetate/methanol 95:5); $v_{max}$ (ATR)/cm$^{-1}$ 3118, 2940, 2830, 1528, 1507, 1478, 1357, 1263, 1239, 1111, 1060, 993, 863, 804, 730; $^1$H NMR (300 MHz, CDCl$_3$) δ 3.42 (3H, s), 3.57 (3H, s), 3.76 (3H, s), 3.84 (3H, s), 7.07 (1H, s), 7.14 (1H, dd, J=8.5 Hz, J=1.6 Hz), 7.3-7.4 (3H, m), 7.54 (1H, s), 7.55 (1H, d, J=1.6 Hz); $^{13}$C NMR (75.5 MHz, CDCl$_3$) 832.0, 33.0, 55.9, 61.7, 104.6, 110.5, 113.0, 113.5, 120.4, 120.9, 124.8, 126.1, 126.5, 130.5, 131.2, 135.5, 135.8, 137.1, 140.4, 144.6, 153.3; m/z (EI) 428 (38) [M$^+$], 426 (100) [M$^+$], 411 (26).

32) 4-(3'-Amino-4',5'-dimethoxyphenyl)-5-(3"-amino-4"-methoxyphenyl)-oxazole 8a Compound 7a (120 mg, 0.30 mmol) was suspended in methanol (20 mL) and treated with ammonium formate (590 mg, 9.37 mmol) and Pd/C (5%, 180 mg). The suspension was refluxed for 2 h and after cooling to room temperature the mixture was filtered over celite, the filtrate was concentrated in vacuum and the residue was purified by column chromatography (silica gel 60). Yield: 70 mg (0.21 mmol, 70%); light brown solid of mp 63° C.; $R_f$=0.55 (ethyl acetate); UV (MeOH) $\lambda_{max}$ (ε) 285 (7720); $v_{max}$ (ATR)/cm$^{-1}$ 3457, 3361, 2935, 2834, 1613, 1587, 1515, 1428, 1378, 1222, 1175, 1137, 1105, 999, 843, 802, 760; $^1$H NMR (300 MHz, CDCl$_3$) δ 3.73 (3H, s), 3.80 (3H, s), 3.82 (3H, s), 3.9-4.0 (4H, broad s), 6.6-6.8 (3H, m), 6.9-7.0 (2H, m), 7.83 (1H, s); $^{13}$C NMR (75.5 MHz, CDCl$_3$) δ 55.4, 55.6, 59.8, 102.1, 108.2, 110.1, 113.2, 117.6, 121.5, 128.1, 133.2, 135.6, 136.1, 140.4, 145.7, 147.6, 148.9, 152.7; m/z (EI) 343 (45), 341 (66) [M$^+$], 326 (46), 298 (22), 197 (63), 91 (100), 57 (75).

33) 4-(3'-Amino-4',5'-dimethoxyphenyl)-5-(3"-amino-4"-methoxyphenyl)-oxazole bis(hydrochloride) 8a×2 HCl Compound 8a (60 mg, 0.18 mmol) was dissolved in DCM (5 mL) and treated with 3M HCl/dioxane (1 mL). The reaction mixture was stirred at room temperature for 15 min and the formed colorless precipitate was collected, washed with DCM and dried in vacuum. Yield: 28 mg (0.07 mmol, 39%); colorless solid of mp 227° C.; UV (MeOH) $\lambda_{max}$ (ε) 292 (11960); $v_{max}$ (ATR)/cm$^{-1}$ 2837, 2553, 1633, 1567, 1518, 1495, 1376, 1270, 1142, 1102, 1052, 996, 934, 869, 839, 817, 760, 722; $^1$H NMR (300 MHz, DMSO-d$_6$) δ 3.74 (3H, s), 3.85 (3H, s), 3.92 (3H, s), 7.10 (1H, s), 7.19 (1H, s), 7.25 (1H, d, J=8.7 Hz), 7.4-7.5 (1H, m), 7.56 (1H, d, J=2.1 Hz), 8.52 (1H, s); $^{13}$C NMR (75.5 MHz, DMSO-d$_6$) δ 55.9, 56.2, 60.7, 108.9, 112.6, 113.1, 120.2, 120.6, 124.8, 125.4, 127.5, 128.9, 132.4, 140.3, 144.3, 151.2, 151.6, 152.7; m/z (EI) 341 (100) [M$^+$2 HCl], 376 (72), 298 (25), 255 (12), 212 (7), 184 (7), 135 (8), 78 (11), 65 (6).

34) 4-(3'-Amino-4',5'-dimethoxyphenyl)-5-(4"-N,N-dimethylaminophenyl)-oxazole 8b Compound 7b (100 mg, 0.27 mmol) was suspended in methanol (20 mL) and treated with ammonium formate (590 mg, 9.37 mmol) and Pd/C (5%, 180 mg). The suspension was refluxed for 2 h and after cooling to room temperature the mixture was filtered over celite, the filtrate was concentrated in vacuum and the residue was purified by column chromatography (silica gel 60). Yield: 60 mg (0.18 mmol, 67%); colorless oil; $R_f$=0.77 (ethyl acetate/methanol 95:5); $v_{max}$ (ATR)/cm$^{-1}$ 3427, 3295, 3189, 2927, 2820, 1617, 1583, 1523, 1512, 1445, 1426, 1382, 1363, 1327, 1278, 1227, 1190, 1146, 1105, 1057, 1005, 949, 842, 817; $^1$H NMR (300 MHz, CDCl$_3$) δ 2.96 (6H, s), 3.76 (3H, s), 3.82 (3H, s), 6.6-6.8 (4H, m), 7.49 (2H, d, J=9.1 Hz), 7.82 (1H, s); $^{13}$C NMR (75.5 MHz, CDCl$_3$) δ 40.1, 55.7, 59.9, 102.0, 108.0, 111.8, 116.4, 128.0, 128.5, 132.2, 135.5, 140.4, 146.3, 148.6, 150.4, 152.8; m/z (EI) 339 (82) [M$^+$], 324 (70), 296 (25), 253 (44), 159 (41), 148 (100), 133 (59), 119 (84), 78 (67), 42 (54).

35) 4-(3'-Amino-4',5'-dimethoxyphenyl)-5-(4"-N,N-dimethylaminophenyl)-oxazole bis(hydrochloride) 8b×2 HCl Compound 8b (58 mg, 0.17 mmol) was dissolved in DCM (5 mL) and treated with 3M HCl/dioxane (1 mL). The reaction mixture was stirred at room temperature for 15 min, the solvent was removed and the formed colorless solid was recrystallized from DCM/n-hexane. Yield: 70 mg (0.17 mmol, 100%); yellow solid of mp 74° C.; UV (MeOH) $\lambda_{max}$ (ε) 327 (18200), 259 (16360); $v_{max}$ (ATR)/cm$^{-1}$ 3382, 2941, 2840, 2548, 1572, 1541, 1512, 1496, 1418, 1378, 1276, 1251, 1104, 1062, 991, 935, 870, 850; $^1$H NMR (300 MHz, DMSO-d$_6$) δ 2.99 (6H, s), 3.74 (3H, s), 3.87 (3H, s), 6.9-7.1 (2H, m), 7.22 (1H, d, J=1.9 Hz), 7.28 (1H, d, J=1.9 Hz), 7.49 (2H, d, J=8.9 Hz), 8.46 (1H, s); $^{13}$C NMR (75.5 MHz, DMSO-d$_6$) δ 40.7, 55.9, 61.0, 110.4, 113.8, 113.9, 126.7, 128.0, 128.2, 130.9, 141.0, 145.9, 149.4, 150.7, 152.6; m/z (EI) 339 (82) [M$^+$-2 HCl], 324 (70), 296 (25), 253 (44), 159 (41), 148 (100), 133 (59), 119 (84), 78 (67), 42 (54).

36) 1-Methyl-4-(3'-amino-4',5'-dimethoxyphenyl)-5-(3"-hydroxy-4-methoxyphenyl)-imidazole bis(hydrochloride) 8c×2 HCl Compound 7c (120 mg, 0.31 mmol) was dissolved in methanol (20 mL) and treated with ammonium formate (590 mg, 9.37 mmol) and Pd/C (5%, 180 mg). The suspension was refluxed for 2 h and after cooling to room temperature the mixture was filtered over celite, the filtrate was concentrated in vacuum and the residue was purified by column chromatography giving 8c (silica gel 60, ethyl acetate/methanol 95:5, $R_f$=0.25). Compound 8c was dissolved in DCM (5 mL) and treated with 3M HCl/dioxane (1 mL). The reaction mixture was stirred at room temperature for 15 min. The solvent was removed and the residue freed from dioxane by repeated azeotropic distillation with DCM. The remaining solid was recrystallized from ethanol/n-hexane. Yield: 70 mg (0.16 mmol, 53%); colorless solid of mp 218° C. (dec.); UV (MeOH) $\lambda_{max}$ (ε) 275 (11300); $v_{max}$ (ATR)/cm$^{-1}$ 3032, 2967, 2522, 1620, 1590, 1534, 1508, 1432, 1328, 1292, 1251, 1211, 1135, 1109, 1051, 1026, 992, 855, 813, 766; $^1$H NMR (300 MHz, DMSO-d$_6$) δ 3.61 (3H, s), 3.73 (3H, s), 3.77 (3H, s), 3.83 (3H, s), 6.75 (1H, d, $^4$J 1.7 Hz), 6.8-7.0 (3H, m), 7.09 (1H, d, $^3$J 8.5 Hz), 9.33 (1H, s); $^{13}$C NMR (75.5 MHz, DMSO-d$_6$): δ 33.9, 55.6, 55.9, 60.3, 109.5, 112.7, 117.5, 122.1, 122.8, 128.2, 129.9, 135.2, 147.1, 149.3, 152.6; m/z (EI) 356 (33), 355 (85) [M$^+$-2 HCl], 341 (42), 340 (100).

37) 1-Methyl-4-(3'-amino-4',5'-dimethoxyphenyl)-5-(3"-fluoro-4-methoxyphenyl)-imidazole 8d Compound 7d (120 mg, 0.31 mmol) was dissolved in methanol (20 mL) and treated with ammonium formate (590 mg, 9.37 mmol) and Pd/C (5%, 180 mg). The suspension was refluxed for 2 h and after cooling to room temperature the mixture was filtered over celite, the filtrate was concentrated in vacuum and the residue was purified by column chromatography (silica gel 60). Yield: 80 mg (0.25 mmol, 81%); colorless gum; $R_f$=0.33 (ethyl acetate/methanol 95:5); $v_{max}$ (ATR)/cm$^{-1}$ 3448, 3364, 2940, 2835, 1610, 1561, 1517, 1500, 1463, 1442, 1394, 1301, 1268, 1237, 1208, 1132, 1107, 1049, 1024, 1002, 892, 877, 848, 817, 761, 658; $^1$H NMR (300 MHz, CDCl$_3$) δ 3.38 (3H, s), 3.5-3.6 (2H, broad s), 3.59 (3H, s), 3.72 (3H, s), 3.87 (3H, s), 6.47 (1H, d, J=1.9 Hz), 6.48 (1H, d, J=1.9 Hz), 6.9-7.1 (3H, m), 7.45 (1H, s); $^{13}$C NMR (75.5 MHz, CDCl$_3$) δ 31.9, 55.2, 56.1, 59.7, 100.1, 106.9, 113.5, 118.2, 118.4, 123.1, 123.2, 126.9, 127.0, 127.1, 130.3, 134.6, 137.0, 138.1, 140.0, 147.7, 147.9, 150.5, 152.4, 153.7; m/z (EI) 358 (57), 357 (93) [M$^+$], 343 (75), 342 (100), 282 (47), 243 (51), 229 (50), 200 (42), 158 (34), 42 (72).

38) 1-Methyl-4-(3'-amino-4',5'-dimethoxyphenyl)-5-(3"-fluoro-4-methoxyphenyl)-imidazole bis(hydrochloride) 8d×2 HCl Compound 8d (80 mg, 0.25 mmol) was dissolved in DCM (5 mL) and treated with 3M HCl/dioxane (1 mL). The reaction mixture was stirred at room temperature for 15 min. The solvent was removed and the residue freed from dioxane by repeated azeotropic distillation with DCM. The remaining solid was recrystallized from ethanol/n-hexane. Yield: 90 mg (0.21 mmol, 84%); colorless solid of mp 214-217° C.; UV (MeOH) $\lambda_{max}$ (ε) 270 (11100); $v_{max}$ (ATR)/cm$^{-1}$ 2969, 2323, 1625, 1555, 1526, 1494, 1473, 1422, 1341, 1305, 1278, 1242, 1178, 1131, 1112, 1061, 1025, 974, 858, 825, 763; $^1$H NMR (300 MHz, DMSO-d$_6$) δ 3.63 (3H, s), 3.77 (3H, s), 3.78 (3H, s), 3.92 (3H, s), 6.66 (1H, s), 7.05 (1H, s), 7.2-7.3 (1H, m), 7.35 (1H, t, J=17.3 Hz), 7.47 (1H, d, J=12.0 Hz), 9.37 (1H, s); $^{13}$C NMR (75.5 MHz, DMSO-d$_6$) δ 34.0, 55.0, 56.2, 60.3, 111.4, 114.7, 117.6, 117.7, 118.2, 118.5, 122.6, 128.1, 128.5, 129.0, 135.4, 140.0, 148.7, 148.8, 149.8, 152.6, 153.0; m/z (EI) 358 (63), 357 (96) [M$^+$-2 HCl], 343 (79), 342 (100), 284 (37).

39) 1-Methyl-4-(3'-amino-4',5'-dimethoxyphenyl)-5-(N-methyl-3"-chloroindol-5"-yl)-imidazole 8e Compound 7e (120 mg, 0.28 mmol) was dissolved in THF (7.5 mL) and reduced by adding Zn powder (90 mg, 1.39 mmol) and conc. HCl (200 µL) in THF (1 mL). After workup the residue was purified by column chromatography (silica gel 60). Yield: 70 mg (0.18 mmol, 64%); colorless oil; $R_f$=0.44 (ethyl acetate/methanol 95:5); $v_{max}$ (ATR)/cm$^{-1}$ 3359, 3113, 2934, 2825, 1613, 1593, 1511, 1480, 1447, 1423, 1396, 1336, 1239, 1224, 1139, 1109, 1000, 974, 907, 864, 803, 726; $^1$H NMR (300 MHz, CDCl$_3$) δ 3.39 (3H, s), 3.52 (3H, s), 3.70 (3H, s), 3.74 (3H, s), 6.50 (1H, d, J=1.9 Hz), 6.58 (1H, d, J=1.9 Hz), 7.05 (1H, s), 7.16 (1H, dd, J=8.5 Hz, J=1.6 Hz), 7.32 (1H, d, J=8.5 Hz), 7.50 (1H, s), 7.58 (1H, d, J=1.6 Hz); $^{13}$C NMR (75.5 MHz, CDCl$_3$) δ 32.0, 33.0, 55.3, 59.7, 101.0, 104.6, 106.8, 110.1, 120.6, 122.1, 125.5, 125.9, 126.1, 129.1, 130.8, 134.5, 135.6, 136.6, 137.6, 139.8, 152.4; m/z (EI) 398 (19) [M$^+$], 396 (56) [M$^+$], 383 (37), 381 (100), 321 (11), 282 (12), 42 (23).

40) 1-Methyl-4-(3'-amino-4',5'-dimethoxyphenyl)-5-(N-methyl-3"-chloroindol-5"-yl)-imidazole tris(hydrochloride) 8e×2 HCl Compound 8e (70 mg, 0.18 mmol) was dissolved in DCM (5 mL) and treated with 3M HCll/dioxane (1 mL). The reaction mixture was stirred at room temperature for 15 min. The solvent was removed and the residue freed from dioxane by repeated azeotropic distillation with DCM. The remaining solid was recrystallized from ethanol/n-hexane. Yield: 62 mg (0.12 mmol, 68%); brown solid of mp>300° C. (dec.); UV (MeOH) $\lambda_{max}$ (ε) 224 (30100); $v_{max}$ (ATR)/cm$^{-1}$ 3356, 2830, 2570, 1623, 1554, 1498, 1456, 1423, 1408, 1332, 1284, 1272, 1237, 1145, 1112, 1064, 991, 973, 857, 804; $^1$H NMR (300 MHz, DMSO-d$_6$) δ 3.61 (3H, s), 3.63 (3H, s), 3.73 (3H, s), 3.89 (3H, s), 6.52 (1H, s), 6.79 (1H, s), 7.30 (1H, dd, J=8.5 Hz, J=1.6 Hz), 7.6-7.8 (3H, m), 9.35 (1H, s); $^{13}$C NMR (75.5 MHz, DMSO-d$_6$) δ 33.0, 34.0, 55.7, 60.0, 102.7, 111.7, 117.0, 120.3, 122.8, 124.6, 125.1, 128.0, 128.9, 130.4, 135.1, 136.0, 152.5; m/z (EI) 396 (42) [M$^+$-2 HCl], 383 (45), 381 (78), 331 (21), 160 (100), 57 (59), 41 (65).

41) (3-Fluoro-4-methoxyphenyl)-(p-toluenesulfonyl)methylisocyanide 4d

A mixture of 3-fluoro-4-methoxybenzaldehyde (3.9 g, 22.94 mmol), p-toluenesulfinic acid (3.0 g, 19.29 mmol), camphorsulfonic acid (110 mg) and formamide (10 mL) was stirred at 65° C. for 16 h. After cooling in an ice bath the mixture was treated with water and the resulting precipitate was separated, washed with a little methanol and dried in vacuum to leave the N-substituted formamide (1.9 g, 5.64 mmol, 30%). This compound was dissolved in dry DME (50 mL), cooled to −5° C. and treated with POCl$_3$ (1.7 mL) and Et$_3$N (4.15 mL). The reaction mixture was stirred at −5° C. for 2 h. The resulting suspension was poured on ice water and extracted with ethyl acetate. The organic phase was washed with aqueous NaHCO$_3$ and brine, dried over Na$_2$SO$_4$, filtered and the filtrate was concentrated in vacuum. The residue thus obtained was purified by column chromatography (silica gel 60). Yield: 560 mg (1.76 mmol, 31%); R$_f$=0.41 (ethyl acetate/n-hexane, 1:2); brown solid of mp 86-90° C. (dec.); $v_{max}$ (ATR)/cm$^{-1}$ 2947, 2845, 2134, 1620, 1595, 1518, 1441, 1324, 1304, 1273, 1225, 1148, 1126, 1082, 1018, 811, 761, 664; $^1$H NMR (300 MHz, CDCl$_3$) δ 2.46 (3H, s), 3.90 (3H, s), 5.50 (1H, s), 6.05 (1H, t, J$_{HF}$=16.8 Hz), 7.0-7.2 (2H, m), 7.33 (2H, d, J=7.4 Hz), 7.63 (2H, d, J=7.4 Hz); $^{13}$C NMR (75.5 MHz, CDCl$_3$) δ 21.8, 56.3, 75.6, 113.1, 113.2, 116.1, 116.3, 118.8, 118.9, 124.9, 125.0, 129.9, 130.5, 146.8, 149.7, 149.8, 150.3, 153.6, 166.3; m/z (EI) 344 (12) [M$^+$], 319 (5), 278 (34), 246 (22), 164 (100), 155 (61), 139 (74), 102 (33), 91 (99), 65 (44).

42) 1-Methyl-5-(3-bromo-4,5-dimethoxyphenyl)-4-(3-fluoro-4-methoxyphenyl)imidazole×HCl 9a A mixture of 3-bromo-4,5-dimethoxybenzaldehyde (86 mg, 0.35 mmol) and 33% MeNH$_2$/ethanol (220 μL, 1.78 mmol) in ethanol (15 mL) was treated with AcOH (125 μL, 2.19 mmol) and refluxed for 2 h. After cooling to room temperature, 4d (110 mg, 0.35 mmol) and K$_2$CO$_3$ (500 mg, 3.62 mmol) were added and the reaction mixture was refluxed for 5 h. The solvent was evaporated, the residue was diluted with ethyl acetate, washed with water, dried over Na$_2$SO$_4$, filtered and concentrated in vacuum. The residue was purified by column chromatography (silica gel 60, ethyl acetate, R$_f$=0.38) to leave the imidazole as a colorless oil. This was dissolved in CH$_2$Cl$_2$ (5 mL) and treated with 3 M HCl in dioxane (1 mL). After stirring for 5 min the solvent was evaporated and the residue crystallized from CH$_2$Cl$_2$/hexane. Yield: 60 mg (37%); off-white solid of mp 85-86° C.; $v_{max}$ (ATR)/cm$^{-1}$ 3011, 2940, 2841, 2605, 1627, 1590, 1552, 1520, 1499, 1464, 1443, 1421, 1400, 1307, 1275, 1239, 1208, 1181, 1147, 1136, 1105, 1023, 994, 894, 864, 809, 762, 730, 694; $^1$H NMR (300 MHz, DMSO-d$_6$) δ 3.65 (3H, s), 3.82 (3H, s), 3.83 (3H, s), 3.84 (3H, s), 7.1-7.4 (5H, m), 9.23 (1H, s); $^{13}$C NMR (75.5 MHz, DMSO-d$_6$) δ 33.9, 56.1, 56.5, 60.3, 114.3, 114.5, 114.8, 115.3, 117.2, 123.1, 123.9, 126.5, 127.8, 135.7, 147.1, 149.5, 152.7, 153.8; m/z (EI) 422 (92) [M$^+$, free base], 420 (92) [M$^+$], 407 (24), 405 (23).

43) 1-Methyl-4-(3-fluoro-4-methoxyphenyl)-5-(3,5-dibromo-4-methoxyphenyl)-imidazole×HCl 9b A mixture of 3,5-dibromo-4-methoxybenzaldehyde (103 mg, 0.35 mmol) and 33% MeNH$_2$/ethanol (220 μL, 1.78 mmol) in ethanol (15 mL) was treated with AcOH (125 μL, 2.19 mmol) and refluxed for 2 h. After cooling to room temperature, 4d (110 mg, 0.35 mmol) and K$_2$CO$_3$ (500 mg, 3.62 mmol) were added and the reaction mixture was refluxed for 5 h. The solvent was evaporated, the residue was diluted with ethyl acetate, washed with water, dried over Na$_2$SO$_4$, filtered and concentrated in vacuum. The residue was purified by column chromatography (silica gel 60, ethyl acetate/methanol 9:1, R$_f$=0.6) giving the imidazole as a colorless oil. This oil was dissolved in CH$_2$Cl$_2$ (5 mL) and treated with 3 M HCl in dioxane (1 mL). After stirring for 5 min the solvent was evaporated and the residue was crystallized from CH$_2$Cl$_2$/hexane. Yield: 90 mg (51%); colorless solid of mp 125-130° C.; $v_{max}$ (ATR)/cm$^{-1}$ 3380, 3123, 3011, 2940, 2841, 2610, 1628, 1585, 1551, 1522, 1494, 1463, 1442, 1411, 1307, 1278, 1258, 1208, 1163, 1137, 1106, 1021, 988, 877, 814, 754, 723; $^1$H NMR (300 MHz, DMSO-d$_6$) δ 3.65 (3H, s), 3.84 (3H, s), 3.89 (3H, s), 7.0-7.1 (1H, m), 7.23 (1H, t, J$_{HF}$=17.7 Hz), 7.32 (1H, dd, J=12.5 Hz, 2.2 Hz), 7.86 (2H, s), 9.19 (1H, s); $^{13}$C NMR (75.5 MHz, DMSO-d$_6$) δ 33.9, 56.1, 60.6, 114.3, 114.7, 115.0, 118.2, 124.1, 125.2, 126.2, 135.2, 136.1, 147.8, 149.5, 152.8, 154.9; m/z (EI) 472 (52) [M$^+$, free base], 470 (100) [M$^+$, free base], 468 (28) [M$^+$, free base], 455 (19), 330 (19), 36 (40).

44) 1-Methyl-4-(3-fluoro-4-methoxyphenyl)-5-(3,5-diiodo-4-methoxyphenyl)-imidazole×HCl 9c A mixture of 3,5-diodo-4-methoxybenzaldehyde (160 mg, 0.41 mmol) and 33% MeNH$_2$/ethanol (260 μL, 2.10 mmol) in ethanol (15 mL) was treated with AcOH (150 μL, 2.63 mmol) and refluxed for 2 h. After cooling to room temperature, 4d (150 mg, 0.47 mmol) and K$_2$CO$_3$ (500 mg, 3.62 mmol) were added and the reaction mixture was refluxed for 5 h. The solvent was evaporated, the residue was diluted with ethyl acetate, washed with water, dried over Na$_2$SO$_4$, filtered and concentrated in vacuum. The residue was purified by column chromatography (silica gel 60, ethyl acetate, R$_f$=0.48) affording the imidazole as a colorless oil. This oil was dissolved in CH$_2$Cl$_2$ (5 mL) and treated with 3 M HCl in dioxane (1 mL). After stirring for 5 min the solvent was evaporated and the residue crystallised from CH$_2$Cl$_2$hexane. Yield: 60 mg (25%); off-white solid of mp 207-210° C. (dec.); $v_{max}$ (ATR)/cm$^{-1}$ 3111, 3055, 3003, 2928, 2841, 2627, 1633, 1571, 1549, 1519, 1491, 1469, 1443, 1393, 1337, 1309, 1280, 1258, 1208, 1183, 1149, 1106, 1068, 1016, 991, 894, 875, 863, 814, 767, 741, 696; $^1$H NMR (300 MHz, DMSO-d$_6$) δ 3.62 (3H, s), 3.83 (3H, s), 3.84 (3H, s), 7.0-7.1 (1H, m), 7.2-7.3 (2H, m), 7.98 (2H, s), 9.11 (1H, s); $^{13}$C NMR (75.5 MHz, DMSO-d$_6$) δ 34.4, 56.8, 60.9, 92.8, 114.9, 115.0, 115.2, 115.5, 124.4, 124.5, 126.6, 136.6, 142.3, 148.1, 150.0, 160.4; m/z (EI) 564 (100) [M$^+$, free base], 549 (33).

Example 3

Biological Assays

1-Methyl-5-(3-amino-4-methoxyphenyl)-4-(3-chloro-4, 5-dimethoxyphenyl)-imidazole ("5b") as a representative compound of the present invention has been subjected to in vitro and in vivo assays, as described in the following.

For the biotests compound 5b was dissolved in physiological saline solution. Concentrations as high as 10 mM could be achieved thus demonstrating the good solubility. Customarily, in vivo applications to animals require only concentrations up to 3 mM. In order to check the chemical stability of such solutions of 5b they were stored for one month and subsequently used in in vitro tests alongside freshly prepared solutions of the same concentrations of 5b.

Analysis of tubulin polymerization was performed using the Tubulin Polymerization Assay Kit (Cytoskeleton, USA) according to manufacturer's instructions. The assay is fluorescence-based and tubulin polymerization was followed by measuring RFU (relative fluorescence units) on the SpectraFluor Plus (Tecan, Switzerland) using the following filters: excitation 360 nm, emission 465 nm.

The cytotoxic activity of 5b was established by standard colorimetric tests (SRB- and MTT-assays) against various tumor cell lines of different entities. For the SRB cytotoxicity assay, dose-response curves of the testicular germ cell tumor cell lines exposed to drug concentrations of 0.001-10 µM were established using the sulforhodamine-B (SRB) microcuiture colorimetric assay (Papazisis et al. Optimization of the sulforhodamine B colorimetric assay. *J. Immunol. Methods* 1997, 208, 151-158) and performed as described in: Müller et al. Failure of activation of caspase-9 induces a higher threshold for apoptosis and cisplatin resistance in testicular cancer. *Cancer Res.* 2003, 63, 513-521. Briefly, cells were seeded into 96-well plates on day 0, at cell densities previously determined to ensure exponential cell growth during the period of the experiment. On day 1, cells were treated with the drugs dissolved in medium to give the appropriate concentrations for indicated times and the percentage of surviving cells relative to untreated controls was determined on day 5.

The assays for inhibition of the polymerization of tubulin and for the cytotoxicities revealed high, unattenuated activity and efficacy of 5b, as shown in FIGS. 1 and 2.

Unlike cisplatin, compound 5b showed similar in vitro activity against the two germ cell tumor cell lines H12.1 and 1411HP with IC$_{50}$ (96 h)≈30-50 nM, i.e., it overcame the chemoresistance of the 1411HP cells (FIG. 3A). This suggests that compound 5b operates by a differential mechanism of action, initiating growth inhibition and cell death also in multi-drug resistant tumor cells. Comparable results can be obtained, e.g., with compound 6b according to the invention (FIG. 3B).

In vivo antitumor activity and tolerability of compounds 5b and 6b of the invention were studied in a nude mouse xenograft model of the resistant germ cell tumor cell line 1411HP employing Athymic Nude-Fox n1 nu/nu mice (Harlan und Winkelmann, Borchen, Germany).

Prior to testing compound 5b, healthy animals of this type were treated with an ascending range of doses of 5b in order to establish a toxicity profile. The compound was very well tolerated by the mice even at relatively high concentrations. Suitable dosages were then administered in further tests in a nude mouse xenograft model of a pair of germ cell tumor cell lines, the chemoresistant cell line 1411HP and the chemosensitive cell line H12.1. These cell lines retain their individual in vitro chemosensitivities to cisplatin when grown as xenograft tumors and so may serve as a model of the clinical situation of resistance to chemotherapy (Mueller et al. *Cancer Res.* 2003; Mueller et al. *Tumor Biol.* 2006). While treatment of H12.1 xenograft bearing mice with cisplatin led to complete regressions, 1411HP xenografts suffered only a transient growth inhibition followed by renewed tumor progress.

The tests were carried out as follows. The mice were kept under pathogen-free conditions, fed on an autoclaved standard diet and given free access to sterilized water. Each of five mice were administered a 150 µL phosphate buffered saline suspension of 10 million 1411HP cells into the left flank to generate subcutaneous xenograft tumors. After 4 weeks one group of two mice bearing 1411HP xenografts with a volume of ca. 1 cm$^3$ were injected i.p. with a single dose of 30 mg/kg body weight of 5b or 6b, respectively. Two mice in the second group with xenografts of a volume of ca. 2.5 cm$^3$ were injected i.p. with 20 mg/kg body weight of 5b on two consecutive days. Tumor volumes were calculated by caliper measurement using the formula a$^2$×b×0.5 with a being the short and b the long dimension. Body weight was assessed twice weekly and daily while under therapy.

After the two mice bearing 1411HP xenografts with a volume of about 1 cm$^3$ were treated with a single dose of 30 mg/kg body weight of 5b or 6b, in either case a strong intratumoral hemorrhage became visible yet after 24 h as a red-blue to brown coloring, as shown in FIG. 5 for treatment with 5b. Also visible was a transient swelling of the tumors, eventually followed by regression and slow regrowth, as shown in FIG. 4 A. Both mice tolerated this treatment very well. A prolonged period of tumor shrinkage was achieved in the two mice bearing 1411HP xenografts of about 2.5 cm$^3$ volume by administration of 20 mg/kg body weight of 5b on two consecutive days. The resulting dramatic tumor regressions, leading even to a stabilization in one case, are shown in FIGS. 4 B/C. The other xenograft regrew and was given two further double doses of 5b on days 16/17 and 35/36. As shown in FIG. 4 C, regressions and prolonged periods of stabilization following each of the three applications were achieved. Notably, even the third course of treatment was well tolerated and the mouse had regained its original body weight by this time. These data demonstrate the great potential of the compounds 5b and 6b for an efficient curative treatment of resistant tumors.

In the mouse model anti-tumor activity of 5b thus became apparent by a dramatic regression of the resistant tumors (FIG. 4). The strong vascular disrupting effect selectively affecting the tumoral vasculature was demonstrated and visualized by a distinct intra-tumoral hemorrhage occurring 24 h after administration of the compound 5b (FIG. 5). In addition, a single dose application of compound 5b was sufficient to stabilize the tumor volume for about two weeks.

Furthermore, a tumor regression trial using dual-dose i. p. application of 2×20 mg/kg body weight of compound 6b in 1411HP germ cell tumor xenograft showed high antitumor activity to a similar extent as compound 5b, as also shown in FIG. 10.

From these findings it can be concluded that the compounds of formula (I), such as, e.g., compound 5b or 6b, represent a class of effectives suitable for the treatment of multi-resistant tumors. Their hallmark is the synergistic combination of high cancer cell-specific cytotoxicity based upon a genuine mechanism, a tumor-selective vascular disrupting effect, favourable pharmacological properties, and excellent tolerance in vivo.

The compounds 5f, 6b and 6f were further tested for vascular disrupting effect in the 1411HP xenograft model, and the compounds 5b, 5f, 6b and 6f were additionally tested in a second tumor model of A2780 ovarian carcinoma xenografts, showing vascular disrupting activity of all compounds in both models (FIG. 11), which suggests a general activity of the compounds of the invention in well vascularized tumors.

Compounds 5b, 6b and 6f were also tested in terms of feasibility of oral administration. Mice received a single dose of 40 mg/kg body weight of 5b, 6b or 6f, respectively. No signs of toxicity were observed. Then compounds 6b or 6f were given peroral as dual-dose application on two consecutive days in accordance to the i.p. treatment scheme used for the regression trials but with a 2-fold higher dose of 2×40 mg/kg body weight. This was well tolerated and induced only a transient and marginal loss of body weight in case of 6b whereas no signs of toxicity were observed for 6f. In addition 6f was administered as single dose of 60 mg/kg body weight and again was tolerated symptom-free. This demonstrates the outstanding toxicity profile of the compounds of the present invention when given peroral even at higher doses.

To prove whether the tumor targeted cytotoxic activity is also achieved after an oral administration of compounds of the invention, the vascular disrupting effect was studied 24 h after giving 60 mg/kg body weight of compound 6b peroral. No signs of toxicity were observed. The vascular disrupting effect occurred to same extent as seen after i.p. application, as also shown in FIG. 12.

Example 4

Cell Growth Inhibition Assay in Various Human Tumor Cell Lines

The effects of the compounds 5b, 6b, 8a, and 8e according to the present invention and of the reference compound 25f (Wang et al., *J. Med. Chem.* 2002, 45, 1697-1711) on cells of the following human tumor cell lines were evaluated: 518A2 melanoma, HL-60 leukemia, HT-29 colon carcinoma, KB-V1/Vbl cervical carcinoma, and MCF-7/Topo breast carcinoma.

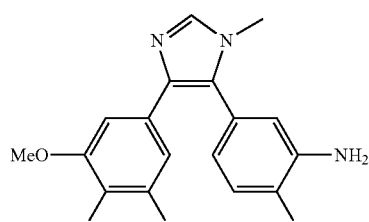

25f

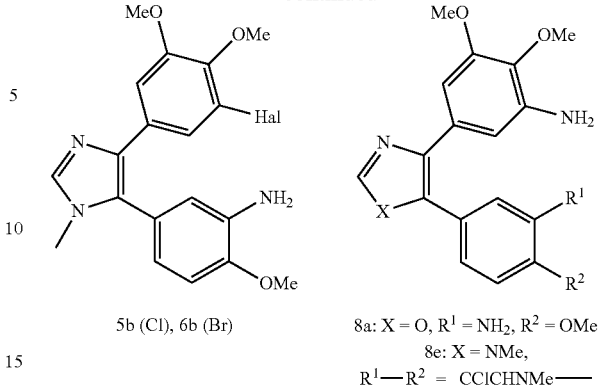

5b (Cl), 6b (Br)

8a: X = O, $R^1$ = $NH_2$, $R^2$ = OMe
8e: X = NMe,
$R^1$—$R^2$ = CClCHNMe—

The HL-60 cells were obtained from the German Collection of Biological Material (DSMZ), Braunschweig, Germany; the human 518A2 melanoma cells as well as the testicular germ cell tumor cell lines H12.1 and 1411HP were cultured in the department of oncology and hematology, Medical Faculty of the Martin-Luther University, Halle, Germany; the KBV1/Vbl and the MCF-7/Topo cells were obtained from the Institute of Pharmacy of the University Regensburg, Germany; and the colon HT-29 cells from the University Hospital Erlangen, Germany. The HL-60 and the HT-29 cells were grown in RPMI-1640 medium supplemented with 10% fetal calf serum (FCS), 100 IU/mL penicillin G, 100 μg/mL streptomycin sulfate, 0.25 μg/mL amphotericin B and 250 μg/mL gentamycine (all from Gibco, Egenstein, Germany). The 518A2 and the KB-V1/Vbl cells were cultured in Dulbecco's Modified Eagle Medium (D-MEM, Gibco) containing 10% FCS, 100 IU/mL penicillin G, 100 μg/mL streptomycin sulfate, 0.25 μg/mL amphotericin B and 250 μg/mL gentamycine. The MCF-7/Topo cells were grown in E-MEM medium (Sigma) supplemented with 2.2 g/L NaHCO3, 110 mg/L sodium pyruvate and 5% FCS. The cells were maintained in a moisture-saturated atmosphere (5% $CO_2$) at 37° C. in 75-mL culture flasks (Nunc, Wiesbaden, Germany). They were serially passaged following trypsinisation by 0.05% trypsin/0.02% EDTA (PAA laboratories, Clbe, Germany). *Mycoplasma* contamination was routinely monitored, and only mycoplasma-free cultures were used.

MTT [3-(4,5-dimethylthiazol-2-yl)-2,5-diphenyltetrazolium bromide](ABCR) was used to identify viable cells which reduce it to a violet formazan (Mosmann, *J. Immunol. Methods* 1983, 65, 55-63). HL-60 leukemia cells ($5×10^5$/mL), and cells ($5×10^4$/mL) of 518A2 melanoma, HT-29 colon, KB-V1/Vbl cervix and MCF-7/Topo breast carcinoma were seeded out in 96-well tissue culture plates and cultured for 24 h. Incubation (5% $CO_2$, 95% humidity, 37° C.) of the cells following treatment with the test compounds was continued for 24, 48 or 72 h. Blank and solvent controls were treated identically. MTT in phosphate buffered saline (5 mg/mL) was added to a final concentration of 0.05% (HL-60, 518A2) or 0.1% (HT-29, KB-V1/Vbl, MCF-7/Topo). After 2 h the formazan precipitate was dissolved in 10% sodium dodecylsulfate in DMSO containing 0.6% acetic acid in the case of the HL-60 cells. For the adherent 518A2, KB-V1/Vbl, MCF-7/Topo and HT-29 cells the microplates were swiftly turned to discard the medium before adding the solvent mixture. The microplates were gently shaken in the dark for 30 min and absorbance at 570 nm and 630 nm (background) was measured with an ELISA plate reader. All experiments were carried out in quadruplicate; the percentage of viable cells was calculated as the mean±SD with controls set to 100%.

As shown in FIG. 6A, the halo-amino substituted imidazoles 5b and 6b were distinctly more cytotoxic than the known reference compound 25f at $IC_{50}$ concentrations in the single-digit nanomolar range, even in the combretastatin A-4 resistant HT-29 cells and the Pgp-overexpressing KB-V1 cells. Only in the MCF-7/Topo cells they were noticeably less active but still superior to the known imidazole 25f.

In contrast, the diamino substituted oxazole 8a and its imidazole counterpart 8e were more cell line specific with greater efficacy than 25f and 5b/6b against both multidrug-resistant cells, i.e., KB-V1/Vbl (Pgp+) and MCF-7/Topo (BCRP+). This is a hint at potentially different or additional modes of action of these compounds.

Moreover, as shown in FIG. 7, combretastatin A-4 shows lower cytotoxicities than compounds 5b and 6b in the multidrug resistant HT-29 colon cancer cells. Hence, compounds 5b and 6b are able to overcome the drug resistance in these cancer cells in vitro.

The compounds 5b, 6b, 5f and 6f as well as the reference compound 25f (Wang et al.) were furthermore subjected to an SRB-cytotoxicity assay in a panel of tumor cell lines (H12.1 germ cell tumor, 1411HP germ cell tumor, A2780 ovarian carcinoma, HT29 colon carcinoma, DLD1 colon carcinoma, HCT8 colon carcinoma). As shown in FIG. 13, compounds 5b and 6b showed superior activity as compared to compound 25f, and a further improvement of cytotoxicity was observed for the compounds 5f and 6f.

The compounds 9a, 9b and 9c, which are exemplary compounds of formula (III) according to the present invention, as well as the reference compound 25f were tested in a similar manner. As indicated in Table 1, compounds 9a, 9b and 9c showed a more pronounced and selective cytotoxic effect on tumor cells (L929 fibroblasts, KB-3-1 cervix carcinoma, and PC-3 prostata cancer) than on non-malign cells (PtK-2 opossum kidney cells and NHDF fibroblasts) as well as an improved effect (MIC) on HUVEC cells as compared to the reference compound 25f.

TABLE 1

IC50 (nM) in L929 fibroblasts, KB-3-1 cervix carcinoma, PC-3 prostata cancer, PtK-2 opossum kidney cells and NHDF fibroblasts, and minimal inhibitory concentration (MIC) (nM) in HUVEC cells.

| compound | Cell line | | | | | |
| --- | --- | --- | --- | --- | --- | --- |
| | L-929 | KB-3-1 | PC-3 | PtK-2 | NHDF | HUVEC |
| 25f | 215 | 68 | 90 | 453 | 136 | 294 |
| 9a | 24 | 4.4 | — | 437 | 175 | 109 |
| 9b | 21714 | 14 | 9.9 | 1184 | 395 | 257 |
| 9c | 18 | 2.5 | 3.3 | 333 | 3330 | 83 |

Example 5

Reactive Oxygen Species (ROS) Generation Assay

The generation of reactive oxygen species (ROS) in tumor cells is a sign of cellular stress resulting in severe damage of cellular components such as DNA, lipids or proteins. The amount of ROS produced in HL-60 and in 518A2 cells treated with the reference compound 25f or a compound according to the invention was assessed using the colorimetric nitrobluetetrazolium (NBT) assay (Rook et al. *J. Immunol. Methods* 1985, 82, 161-167). The ROS generation (% NBT reduction) was determined from percent absorbance of formazan relative to untreated controls (1%) after 24 h exposure of 518A2 and HL-60 cells to 50 µM of the test compounds.

For the NBT assay, HL-60 cells ($0.5 \cdot 10^6$/mL) were plated in 96-well tissue culture plates, and test compounds were added after 24 h incubation at 37° C. to achieve a final concentration of 50 µM. Incubation (5% $CO_2$, 95% humidity, 37° C.) of cells following treatment with the test compounds was continued for 24 h. After removal of the cell medium by centrifugation, the cells in each well were resuspended in 100 µL 0.1% NBT, and the plates were placed in the incubator for 1 h. The reduced NBT was solubilized with 100 µl 2 M KOH and 130 µl DMSO for 30 min. The absorbance was measured for each well at 630 and 405 nm (background) using an ELISA plate reader. The adherent 518A2 cells ($0.5 \cdot 10^4$/mL) were seeded out in 96-well tissue culture plates after trypsinization and incubation for 24 h at 37° C. to allow attachment, then treated similarly, only that the medium was removed prior to incubation with NBT for 4 h. All experiments were carried out in quadruplicate.

The following results were obtained, the indicated values representing means of four independent experiments±standard deviation:

| | NBT Reduction [%] in 518A2 cells after 24 h | NBT Reduction [%] in HL-60 cells after 24 h |
| --- | --- | --- |
| 25f | 2.2 ± 0.4 | 1.5 ± 0.1 |
| 5b | 1.8 ± 0.2 | 4.4 ± 0.6 |
| 5c | 1.6 ± 0.1 | 4.8 ± 0.5 |
| 5d | 2.4 ± 0.4 | 6.0 ± 0.9 |
| 6b | 1.5 ± 0.2 | 3.8 ± 0.3 |
| 6c | 1.4 ± 0.3 | 3.9 ± 0.1 |
| 6d | 1.6 ± 0.3 | 6.7 ± 0.8 |
| 8a | 1.5 ± 0.1 | 3.5 ± 0.4 |
| 8b | 1.4 ± 0.3 | 3.3 ± 0.2 |
| 8c | 1.1 ± 0.0 | 1.8 ± 0.3 |
| 8d | 1.2 ± 0.1 | 1.4 ± 0.2 |
| 8e | 1.6 ± 0.3 | 6.4 ± 0.3 |

The weakly cytotoxic compound 25f led to a low ROS level, while, e.g., the highly cytotoxic compound 5b according to the invention afforded an ROS level of 4.4%.

Example 6

Mitochondrial Membrane Assay

The extent of apoptosis-related mitochondrial damage in 518A2 and HL-60 cells was ascertained by means of the fluorescence dye JC-1 that detects changes in the mitochondrial membrane potential (Desager et al. *J. Cell. Biol.* 1999, 144, 891-901).

The ratio of red to green fluorescence relative to untreated controls (100%) after 72 h exposure of 518A2 and HL-60 cells to 5 µM of the test compounds (i.e., compounds according to the invention or reference compound 25f) was determined with the Mitochondrial Membrane Detection Kit (Stratagene, La Jolla, Calif., USA). Values represent means of four independent experiments±standard deviation.

Changes in mitochondrial membrane potential were determined by the Mitochondrial Membrane Detection Kit (Stratagene, La Jolla, Calif., USA) according to the manufacturer's procedure. 72 h following treatment with 5 µM of the test compounds, cell samples were centrifuged at 400 g for 5 min. The pellets were resuspended in 500 µL diluted JC-1 solution, incubated at 37° C. for 15 min (HL-60) and then centrifuged again for 5 min at 400 g. After washing, the pellets were resuspended in 100 µL PBS and transferred into the wells of a black 96-well plate. The red ($\lambda_{ex}$=585 nm, $\lambda_{em}$=590 nm) and green ($\lambda_{ex}$=510 nm, $\lambda_{em}$=527 nm) fluorescence intensities were measured and their ratio was calculated.

Again, the impact of the test compounds was more diverse and specific in the HL-60 leukemia cells:

|  | Intact mitochondria [%] in 518A2 cells after 72 h | Intact mitochondria [%] in HL-60 cells after 72 h |
|---|---|---|
| 25f | 87 ± 7 | 74 ± 13 |
| 5b | 80 ± 9 | 65 ± 9 |
| 5c | 84 ± 6 | 55 ± 7 |
| 5d | 80 ± 7 | 61 ± 13 |
| 6b | 80 ± 9 | 66 ± 10 |
| 6c | 89 ± 10 | 60 ± 15 |
| 6d | 82 ± 7 | 63 ± 13 |
| 8a | 85 ± 7 | 62 ± 9 |
| 8b | 82 ± 8 | 62 ± 12 |
| 8c | 94 ± 7 | 76 ± 19 |
| 8d | 98 ± 15 | 90 ± 22 |
| 8e | 77 ± 8 | 60 ± 15 |

Here, only about 65% of the mitochondria were intact after incubation with the more cytotoxic compound 5b, while treatment with 25f left more mitochondria unaffected (74%).

Example 7

TdT-Mediated dUTP Nick-End Labelling (TUNEL) Assay

In TUNEL assays, which allow the detection of apoptosis by labelling the 3'-OH ends of DNA fragments with fluorescein-tagged nucleotides, the compounds 5b, 6b and 8a were found to induce death in HL-60 cells predominantly in an apoptotic way (about 60% after 16 h incubation with 10 µM drug). The extent of apoptosis-related mitochondrial damage in HL-60 cells was ascertained by means of the fluorescence dye JC-1 that detects changes in the mitochondrial membrane potential (Desager et al., *J. Cell. Biol.* 1999, 144, 891-901). Only about 60% of the mitochondria were intact after incubation with the more cytotoxic compounds 5b-d, 6b-d and 8a/e, while treatment with reference compound 25f left 74% of the mitochondria unaffected. Microscopic images of HL-60 cells tested in TUNEL assays after incubation with the compound 5b, 6b or 8a are shown in FIG. 8.

A modification of the TdT-mediated dUTP Nick-End Labelling (TUNEL; Roche) assay described by Jobmann was used (Jobmann, M. Apoptose bei strukturellen Herzmuskelerkrankungen. Ph.D. Thesis, University Marburg, Germany 2002, 31). HL-60 cells were incubated with the test compounds for 16 h, aliquots of 3×10⁶ cells were withdrawn and washed/centrifuged 3 times in 200 µL PBS. The cells were fixed for 10 min at room temperature by suspending in 200 µL of a freshly prepared solution of 2% formalin in PBS. After washing with 2×200 µL PBS, 10 µL of the cell suspension was applied onto a microscope slide and air-dried at room temperature. The cells were washed by covering with PBS for 5 min and treated for 2 min with a solution of 0.1% Triton X-100 in 0.1% sodium citrate on ice. After washing two times with PBS, 10 µL of the freshly prepared TUNEL reaction mixture, consisting of 1 µL TUNEL-Enzyme solution and 9 µL TUNEL-Label solution, was dropped on the cells which were then covered and incubated (5% $CO_2$, 95% humidity) in the dark at 37° C. for 45 min. The cells were washed three times with PBS and then analysed by fluorescence microscopy at an excitation wavelength of 450-500 nm. The percentage of apoptotic, TUNEL-positive, green-stained cells was counted and calculated for 300 cells and expressed as mean±S.D. of three independent experiments.

Example 8

CAM Assay

Compounds of the present invention were tested for anti-angiogenic and vasculature disrupting properties using the CAM assay. In this test the vascular system of a fertilized chicken embryo is used as a model (Wilting et al., *Anat. Embryol.* 1991, 183, 259-271).

Fertilized chicken eggs received from a nearby farm directly after laying have been incubated at a temperature of 36-38° C. and a relative humidity of 60%. During the growth the eggs have been held in an inclined position and turned from time to time in order to avoid an adherence to the shell. After four days each embryo was transferred into a cavity created by fixing a thin plastic foil on top of a cup and covered. This was done by opening the shell at the flat end where the air sac resides and letting the content slip out. There the growth continued for another 2-4 days until the first blood vessels became visible. Then 10 nmol of the substance to be tested (in 10 µL PBS with 1% DMF) have been applied directly on the embryonal vessels. As a reference PBS was used. Finally incubation continued for up to another three days (Dugan et al., *Anat. Rec.* 1991, 229, 125-128; Fisher, *Tested studies for laboratory teaching* 1993, 5, 105-115).

In FIG. 9 the effects of the compounds CA-4 (reference) and 5b on the development of embryonal blood vessels compared to a negative control (PBS) are shown. Like CA-4, compound 5b led to a dramatic vessel shrinkage within 24 h after treatment and to a complete degradation of the vascular system within three days.

Example 9

Tube Formation Assay

The effect of the compounds 5b, 6b and 8a according to the invention as well as reference compound 25f (Wang et al., *J. Med. Chem.* 2002, 45, 1697-1711) on capillary tube formation in HUVEC cells on matrigel has been determined in order to further evaluate the anti-angiogenic properties of these compounds (the structures of the compounds employed are shown in Example 4).

35 µL of media:matrigel (1:1) were added into wells of a 96-well plate and incubated at 37° C. for 30 minutes. A trypsinized HUVEC cell suspension was set to 800.000 cells/mL. In another 96-well plate 25 µL of the compound stock were serially diluted with 25 µL of media. 25 µL of compound dilutions and 25 µL of cell suspension were added to the matrigel coated 96-well plate and the cells were incubated over night. As a negative control, methanol was used as in place of the compound dilutions.

Compounds 6b and 8a showed pronounced inhibition of tube formation by HUVEC cells at very low concentrations (7.72 ng/mL), while compound 5b did not yield a correspondingly strong inhibition at this concentration, as also shown in FIG. 14. Compounds 6b and 8a were distinctly more active than the known compound 25f, which inhibits tube formation at a much higher concentration (130 ng/mL).

Example 10

High-Content Analyses

Automatic microscopy based cluster analyses (High-Content Analyses, HCA) of the compounds 6b and 8a in PtK-2 cells revealed a close relationship to the known tubulin binder vinblastine for compound 6b and to the known PI3-Kinase inhibitor LY294002 for compound 8a. Results are shown in FIG. 15.

instrumentation: ImageXpress Micro (IXM) High-Speed
  Laser Autofocus
  Digital CCD-camera
  300 Watt Xenon arc lamp
  Filter Sets: -DAPI
    FITC
    TRITC
    Texas Red
  Nikon Objectives: -4× Plan Apo, NA 0.20
    10× S Fluor, NA 0.50
    20× S Fluor, NA 0.75
    40× Plan Apo, NA 0.95
    60× Plan Fluor, NA 0.85
  Software: -MetaXpress
    AcuityXpress Parameters (dye-/antibody assays): >50, organised in modules, e.g., MWCS-module using DAPI (W1), FITC (W2) and TRITC (W3) staining and filters.

Descriptors of MWCS-Module:
  Image-based analysis: total cells, (%) positive W2/W3, scoring profile 1-/12-/1-3/123. absolute number of cells appearing stained only at wavelengths 1 and 2 but not 3 (12-)
  Cell-based analysis: total area (area of nuclei), stained area W1/W2/W3 (stained area for individual dyes), positive W2/W3 (absolute numbers of stained cells at each wavelength); average/integrated intensity W1/W2/W3

Reference Compounds: 62

Cell lines: PtK2 (non-malignant), KB-3-1 cervix, A-498 kidney carcinoma

The invention claimed is:

1. A compound of formula (I)

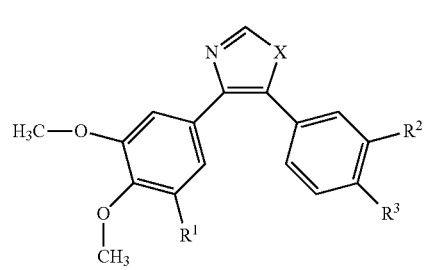

(I)

wherein:
  X is selected from O, S, N(H), or N($C_{1-4}$ alkyl);
  $R^1$ is selected from halogen, —CN, —$CF_3$, —$NH_2$, —NH($C_{1-4}$ alkyl), or —N($C_{1-4}$ alkyl)($C_{1-4}$ alkyl);
  $R^2$ is selected from hydrogen, halogen, —CN, —$CF_3$, —OH, —O($C_{1-4}$ alkyl), —$NH_2$, —NH($C_{1-4}$ alkyl), or —N($C_{1-4}$ alkyl)($C_{1-4}$ alkyl);
  $R^3$ is selected from —OH, —O($C_{1-4}$ alkyl), —SH, —S($C_{1-4}$ alkyl), —$NH_2$, —NH($C_{1-4}$ alkyl), or —N($C_{1-4}$ alkyl)($C_{1-4}$ alkyl);
  or, alternatively, $R^2$ and $R^3$ jointly form a group —C(halogen)=CH—N($CH_3$)—;

or a pharmaceutically acceptable salt, solvate, or prodrug thereof.

2. The compound of claim 1, wherein $R^1$ is selected from —Cl, —Br, or —$NH_2$.

3. The compound of claim 1, wherein $R^2$ is selected from hydrogen, halogen, —OH, or —$NH_2$.

4. The compound of claim 1, wherein $R^3$ is selected from —O—$CH_3$, —O—$CH_2$—$CH_3$, or —N($CH_3$)$_2$.

5. The compound of claim 1, wherein $R^3$ is selected from —O—$CH_3$ or —N($CH_3$)$_2$.

6. The compound of claim 1, wherein $R^2$ and $R^3$ jointly form a group —C(Cl)=CH—N($CH_3$)—.

7. The compound of claim 1, wherein X is selected from O and N($CH_3$).

8. The compound of claim 1, wherein the compound is selected from 1-methyl-5-(3-amino-4-methoxyphenyl)-4-(3-chloro-4,5-dimethoxyphenyl)-imidazole, 1-methyl-5-(3-amino-4-methoxyphenyl)-4-(3-bromo-4,5-dimethoxyphenyl)-imidazole, 1-methyl-5-(3-amino-4-ethoxyphenyl)-4-(3-chloro-4,5-dimethoxyphenyl)-imidazole or 1-methyl-5-(3-amino-4-ethoxyphenyl)-4-(3-bromo-4,5-dimethoxyphenyl)-imidazole, or a pharmaceutically acceptable salt, solvate, or prodrug thereof.

9. The compound of claim 1, wherein the compound is selected from 1-methyl-4-(3-chloro-4,5-dimethoxyphenyl)-5-(3-fluoro-4-ethoxyphenyl)-imidazole or 1-methyl-4-(3-bromo-4,5-dimethoxyphenyl)-5-(3-fluoro-4-ethoxyphenyl)-imidazole, or a pharmaceutically acceptable salt, solvate, or prodrug thereof.

10. The compound of claim 1, wherein the compound is selected from 1-methyl-4-(3-amino-4,5-dimethoxyphenyl)-5-(N-methyl-3-chloroindol-5-yl)-imidazole, 1-methyl-4-(3-chloro-4,5-dimethoxyphenyl)-5-(N-methyl-3-chloroindol-5-yl)-imidazole or 1-methyl-4-(3-bromo-4,5-dimethoxyphenyl)-5-(N-methyl-3-chloroindol-5-yl)-imidazole, or a pharmaceutically acceptable salt, solvate, or prodrug thereof.

11. A pharmaceutical composition comprising the compound of claim 1 and a pharmaceutically acceptable excipient.

12. A method of treating cancer, wherein the cancer is selected from breast cancer, genitourinary cancer, lung cancer, gastrointestinal cancer, epidermoid cancer, melanoma, ovarian cancer, pancreas cancer, neuroblastoma, head and/or neck cancer, bladder cancer, renal cancer, brain cancer, leukemia, and lymphoma, comprising administering the compound of claim 1 to a subject in need thereof.

13. The method of claim 12, wherein the cancer is a multidrug-resistant cancer.

14. The method of claim 12, wherein the cancer is resistant against combretastatin A-4 and/or cisplatin.

15. The method of claim 12, whereby the compound is administered in combination with an anti-proliferative drug, an anticancer drug, a cytostatic drug, a cytotoxic drug and/or radiotherapy.

* * * * *